United States Patent
Gray et al.

(10) Patent No.: US 9,366,814 B2
(45) Date of Patent: Jun. 14, 2016

(54) METHOD FOR PREPARING ZERO-MODE WAVEGUIDE ARRAYS WITH COATED WALLS

(71) Applicant: Pacific Biosciences of California, Inc., Menlo Park, CA (US)

(72) Inventors: Jeremy Gray, Larkspur, CA (US); Ronald L. Cicero, Palo Alto, CA (US); Annette Grot, Cupertino, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 124 days.

(21) Appl. No.: 14/061,348

(22) Filed: Oct. 23, 2013

(65) Prior Publication Data

US 2014/0175052 A1    Jun. 26, 2014

Related U.S. Application Data

(63) Continuation of application No. 12/877,764, filed on Sep. 8, 2010, now Pat. No. 8,906,670.

(60) Provisional application No. 61/241,700, filed on Sep. 11, 2009.

(51) Int. Cl.
 *C12M 1/34* (2006.01)
 *G02B 6/10* (2006.01)
 *G01N 21/64* (2006.01)
 *G01N 21/77* (2006.01)

(52) U.S. Cl.
 CPC .............. *G02B 6/10* (2013.01); *G01N 21/6452* (2013.01); *G01N 21/7743* (2013.01)

(58) Field of Classification Search
 CPC ........... G01N 21/6452; G01N 21/7743; B01L 3/5085; B01L 2300/0829; B01L 2300/0893; B01L 2300/0896; B01L 2300/168
 See application file for complete search history.

(56) References Cited

U.S. PATENT DOCUMENTS

| | | | |
|---|---|---|---|
| 4,927,781 | A  | 5/1990 | Miller |
| 5,350,686 | A  | 9/1994 | Jhingan |
| 6,753,200 | B2 | 6/2004 | Craighead et al. |
| 6,917,726 | B2 | 7/2005 | Levene et al. |
| 7,013,054 | B2 | 3/2006 | Levene et al. |
| 7,033,764 | B2 | 4/2006 | Korlach et al. |

(Continued)

FOREIGN PATENT DOCUMENTS

| | | |
|---|---|---|
| WO | 2007075873 A2 | 7/2007 |
| WO | 2007075987 A2 | 7/2007 |

(Continued)

OTHER PUBLICATIONS

Adhikari et al., "Conditions for subeutectic growth of Ge nanowires by the vapor-liquid-solid mechanism" J Appl Phys (2007) 102:94311-94316.

(Continued)

*Primary Examiner* — William H Beisner
(74) *Attorney, Agent, or Firm* — Robert H. Reamey

(57) ABSTRACT

The application relates to methods of manufacture of improved optical containment structures. The invention relates to arrays of zero-mode waveguide structures comprising nanoscale apertures having non-reflective coatings on their walls. The methods provide for selectively coating the walls of the zero mode waveguides, allowing for selective functionalization of the bases.

15 Claims, 25 Drawing Sheets

(56) References Cited

U.S. PATENT DOCUMENTS

| | | |
|---|---|---|
| 7,052,847 B2 | 5/2006 | Korlach et al. |
| 7,056,661 B2 | 6/2006 | Korlach et al. |
| 7,056,676 B2 | 6/2006 | Korlach et al. |
| 7,170,050 B2 | 1/2007 | Turner et al. |
| 7,181,122 B1 | 2/2007 | Levene et al. |
| 7,315,019 B2 | 1/2008 | Turner et al. |
| 7,486,865 B2 | 2/2009 | Foquet et al. |
| 7,763,423 B2 | 7/2010 | Roitman et al. |
| 2001/0012675 A1* | 8/2001 | Wu .................. 438/435 |
| 2003/0032259 A1 | 2/2003 | Kirchhoff et al. |
| 2003/0044781 A1 | 3/2003 | Korlach et al. |
| 2004/0020784 A1 | 2/2004 | Kinlen et al. |
| 2005/0106758 A1 | 5/2005 | Fukumoto et al. |
| 2006/0061754 A1 | 3/2006 | Turner et al. |
| 2006/0063264 A1* | 3/2006 | Turner et al. ............ 436/8 |
| 2007/0077564 A1 | 4/2007 | Roitman et al. |
| 2007/0134128 A1 | 6/2007 | Korlach |
| 2007/0161017 A1 | 7/2007 | Eid et al. |
| 2007/0238679 A1 | 10/2007 | Rank et al. |
| 2008/0030628 A1 | 2/2008 | Lundquist et al. |
| 2008/0032301 A1 | 2/2008 | Rank et al. |
| 2008/0050747 A1 | 2/2008 | Korlach et al. |
| 2008/0095488 A1 | 4/2008 | Foquet et al. |
| 2008/0220537 A1 | 9/2008 | Foquet |
| 2008/0241866 A1 | 10/2008 | Korlach et al. |
| 2008/0241892 A1 | 10/2008 | Roitman et al. |
| 2009/0118129 A1 | 5/2009 | Turner |
| 2010/0009872 A1 | 1/2010 | Eid et al. |
| 2010/0099100 A1 | 4/2010 | Zaccarin et al. |
| 2010/0261158 A1 | 10/2010 | Nordman et al. |
| 2011/0257040 A1 | 10/2011 | Turner et al. |

FOREIGN PATENT DOCUMENTS

| | | |
|---|---|---|
| WO | 2007107901 A2 | 9/2007 |
| WO | 2008121374 A2 | 10/2008 |
| WO | 2008140758 A1 | 11/2008 |

OTHER PUBLICATIONS

Andersen et al., "Assembly and structural analysis of a covalently closed nanoscale DNA cage" Noel Acids Res (2008) 36(4):1113-1119.

Cerofolini et al., "Strategies for nanoelectronics" Microelec Eng (2005) 81:405-419.

Chen et al., "Critical point energy as a function of electric field determined by electroreflectance of surfacepintrinsic-n+ type doped GaAs" Appl Phys Lett (2004) 84(18):4017-4019.

Cohen et al., "Method for trapping an manipulating nanoscale objects in solution" Appl Phys Lett (2005) 86:93109-1 to 93109-3.

Eid et al., "Real-time DNA sequencing from single polymerase molecules" Science (2008) 323(5910):133-138.

Foquet et al., "Improved fabrication of zero-mode waveguides for single-molecule detection" J Apply Phys (2008) 103:34301-1 to 34301-9.

Korlach et al., "Selective aluminum passivation for targeted immobilization of single DNA polymerase molecules in zero-mode waveguide structures" PNAS (2008) 105(4):1176-1181.

Levene et al., "Zero mode waveguides for single molecule analysis at high concentrations" Science (2003) 299 (5607):682-686.

Leyden et al., "Tailoring surfaces with silanes" Swap Silylated Surfaces, Gordon & Breach (1980) Arkles, Chemtech (1977) 7:766-778.

Montemagno et al., "Constructing nanomechanical devices powered by biomolecular motors" Nanotech (1999) 10:225-231.

TDB-ACC-No. NN8805170, "Optimum Metal Line Structures for Memory Array and Support Circuits," IBM Technical Disclosure Bulletin (May 1988) US 30(12):170-171.

Park et al., "Finite-size fully addressable DNA tile lattices formed by hierarchical assembly procedures" Angew Chem Int Ed (2006) 45:735-739.

Richter et al., "In situ and interrupted-growth studies of the self assembly of octadecyltricholosilane monolayers" Phys Rev E (2000) 61:607-615.

Rothemund et al., "Algorithmic self-assembly of DNA Sierpinski triangles" PLoS Biol (2004) 2(12)e424:2041-2053.

Rothemund, "Folding DNA to create nanoscale shapes and patterns" Nature (2006) 440:297-302.

Svododa et al., "Biological applications of optical forces" Ann Rev Biophys Biomol Structure (1994) 23:247-285.

Weizmann et al., "A polycatenated DNA scaffold for the one-step assembly of hierarchical nanostructures" PNAS (2008) 105(14):5289-5294.

Woodruff et al., "Vertically oriented germanium nanowires grown from gold colloids on silicon substrates and subsequent gold removal" Nano Lett (2007) 7(6):1637-1642.

Zhang et al., "Conformational flexibility facilitates self-assembly of complex DNA nanostructures" PNAS 2008) 105(31):10665-10669.

Zhang et al., "Periodic square-like gold nanoparticle arrays templated by self-assembled 2D DNA nanogrids on a surface" Nano Lett (2006) 6(2)248-251.

Zimmermann et al., "Self assembly of a DNA dodecahedron from 20 Trisoligonucleotides with C3h linkers" Angew Chem Int Ed (2007) 47:3626-3630.

International Search Report dated Aug. 9, 2011 for related application PCT/US2010/002458 filed Sep. 8, 2010.

International Preliminary Report on Patentability dated Mar. 22, 2012 for related application PCT/US2010/002458.

* cited by examiner

METHOD FOR PREPARING ZERO-MODE WAVEGUIDE ARRAYS WITH COATED WALLS

CROSS-REFERENCE TO RELATED APPLICATIONS

This application is a continuation of U.S. patent application Ser. No. 12/877,764, filed Sep. 8, 2010, now U.S. Pat. No. 8,906,670, which claims the benefit of U.S. Provisional Patent Application No. 61/241,700 filed Sep. 11, 2009, which are incorporated by reference herein in their entirety for all purposes.

STATEMENT REGARDING FEDERALLY SPONSORED RESEARCH

Not Applicable.

BACKGROUND OF THE INVENTION

A wide range of analytical operations can benefit from the ability to analyze the reaction of individual molecules or relatively small numbers of molecules. A number of approaches have been described for providing these sparsely populated reaction mixtures. For example, in the field of nucleic acid sequence determination, a number of researchers have proposed single molecule or low copy number approaches to obtaining sequence information in conjunction with the template dependent synthesis of nucleic acids by the action of polymerase enzymes.

The various different approaches to these sequencing technologies offer different methods of monitoring only one or a few synthesis reactions at a time. For example, in some cases, the reaction mixture is apportioned into droplets that include low levels of reactants. In other applications, certain reagents are immobilized onto bead or planar surfaces such that they may be monitored without interference from together reaction components in solution. In still another approach, optical confinement techniques have been used to ascertain signal information only from a relatively small number of reactions, e.g., a single molecule, within and optically confined area.

For arrays of optical confinements it can be desirable to have components to the confinement structures that enable separation of the optical and solution dimensions. Confinement structures can include, for example, zero-mode waveguides consisting of subwavelength apertures extending through a thin cladding layer. Such apertures can provide the ability to observe very small volumes of analyte solution, allowing for reliable optical measurements of single molecules within those volumes. While these optical confinements have significantly advanced the ability to observe single molecules, there is a continuing need for improved optical confinement structures, and for methods and systems for using such structures for applications such as nucleic acid sequencing.

BRIEF SUMMARY OF THE INVENTION

In one aspect, the invention comprises a zero-mode waveguide structure comprising: a transparent substrate having a top surface; an opaque layer disposed upon the top surface of the transparent substrate; an array of apertures extending through the opaque layer to the transparent substrate whereby the apertures comprise wells having walls and bases, the bases of the wells comprising portions of the top surface of the transparent substrate; and a non-reflective layer disposed on the walls of the wells wherein the thickness of the non-reflective layer is greater than about 5 nm.

In some embodiments the thickness of the non-reflective layer is greater than about 10 nm. In some embodiments the non-reflective layer comprises an oxide. In some embodiments the opaque layer comprises a metal, and the non-reflective layer comprises an oxide of such metal. In some embodiments the oxide is formed by oxidation of the opaque layer. In some embodiments the opaque layer comprises a reflective layer. In some embodiments the non-reflective layer comprises phosphorous. In some embodiments the opaque layer comprises aluminum, and the non-reflective layer comprises aluminum oxide. In some embodiments the non-reflective layer comprises an organic polymer. In some embodiments the non-reflective layer comprises a silica-based material. In some embodiments the non-reflective layer comprises a silane polymer.

In some embodiments the apertures comprise cylinders. In some embodiments the apertures comprise conical structures.

An aspect of the invention is a zero-mode waveguide structure comprising: a transparent substrate having a top surface; a reflective layer deposed upon the top surface of the transparent substrate; an array of apertures extending through the reflective layer to the transparent substrate whereby the apertures comprise wells having walls and bases, the bases of the wells comprising portions of the top surface of the transparent substrate; and a non-reflective layer disposed on the walls of the wells wherein the thickness of the non-reflective layer is greater than about 10% of the largest cross-sectional dimension of the wells.

In some embodiments the wells comprise cylindrical structures, whereby the largest cross-sectional dimensions comprise the diameters of the cylinders. In some embodiments the zero-mode waveguide is less than about 80% of the ZMW volume of the zero-mode waveguide. In some embodiments the solution volume of the zero-mode waveguide is less than about 75% of the ZMW volume of the zero-mode waveguide. In some embodiments the solution volume of the zero-mode waveguide is less than about 70% of the ZMW volume of the zero-mode waveguide.

In one aspect, the invention comprises a zero-mode waveguide comprising an aperture having a solution cross-sectional area and a ZMW cross-sectional area, wherein the solution cross-sectional area is less than about 80% of the cross-sectional area of the zero-mode waveguide.

In some embodiments the solution cross-sectional area is less than about 75% of the cross-sectional area of the zero-mode waveguide. In some embodiments the solution cross-sectional area is less than about 70% of the cross-sectional area of the zero-mode waveguide.

In one aspect, the invention comprises a method for forming a zero-mode waveguide structure comprising: providing a substrate having a lower transparent layer and an upper metal layer, wherein the metal layer comprises an array of apertures disposed through the reflective layer to the transparent layer, the apertures having side walls, and exposing the substrate to oxidizing conditions whereby an oxide layer is formed on the side walls of the apertures under conditions whereby an oxide having a thickness of greater than 5 nm is produced.

In some embodiments the oxide is formed by chemical oxidation. In some embodiments the oxide is formed electrochemically. In some embodiments the oxide is formed with an oxygen plasma. In some embodiments the metal comprises aluminum, silver, or titanium.

In one aspect, the invention comprises method for forming a zero-mode waveguide array structure comprising: providing an electrochemical system comprising a working electrode, a counter electrode, and optionally a reference electrode; providing a substrate having a lower transparent layer and an upper electrically conductive reflective layer, wherein the electrically conductive reflective layer comprises an array of apertures disposed through the reflective layer to the transparent layer, the apertures having side walls, wherein the electrically conductive reflective layer comprises the working electrode; and applying a voltage to the working electrode such that a layer of non-reflective material is formed onto the side walls of the aperture.

In some embodiments the layer of non-reflective material comprises an oxide. In some embodiments the working electrode is an anode, and the oxide is formed from the oxidation of the electrically conductive reflective layer. In some embodiments the thickness of the oxide is greater than about 5 nm.

In some embodiments the oxidation of the electrically conductive reflective layer is carried out in the presence of a phosphorous containing compound. In some embodiments the phosphorous containing compound comprises a polymer. In some embodiments the polymer comprises phosphonate groups.

In one aspect, the invention comprises a method for analyzing a luminescent species comprising: disposing a luminescent species in an aperture that extends through an upper reflective layer that is disposed on a lower transparent layer, wherein the aperture comprises side walls, and a non-reflective layer on the side walls of the aperture having a thickness of greater than 5 nm; and detecting emitted light from the luminescent species wherein the emitted light passes through the transparent layer.

In some embodiments the luminescent species comprises a fluorescent species, the method further comprising illuminating the fluorescent species with illumination light. In some embodiments the luminescent species is associated with a biomolecule. In some embodiments the luminescent species is covalently attached to an enzyme substrate and wherein the emitted light provides information regarding the interaction of the enzyme substrate with the enzyme.

In some embodiments the aperture comprises a complex of a polymerase enzyme, a template, and a primer, such complex capable of adding a complementary nucleotide, and wherein the emitted light provides information about the addition of the nucleotide. In some embodiments the luminescent species is covalently attached to the enzyme, the nucleotide, the template, or the primer. In some embodiments the luminescent species is covalently attached to the nucleotide.

In one aspect, the invention comprises an apparatus for obtaining nucleic acid sequence information comprising: a zero-mode waveguide array structure comprising. a transparent substrate having a top surface, and a reflective layer disposed upon the top surface of the transparent substrate; an array of apertures extending through the reflective layer to the transparent substrate wherein the apertures comprise wells having walls and bases, the bases of the wells comprising portions of the top surface of the transparent layer; and a non-reflective layer disposed on the walls of the wells wherein the thickness of the non-reflective layer is greater than about 5 nm; the zero-mode waveguide structure incorporated into a device configured to hold an analysis solution in contact with the zero-mode waveguide structure, whereby the wells comprise the analysis solution which comprises reagents for carrying out reactions for which nucleic acid sequence information can be derived; including polymerase enzyme, nucleotides, and nucleic acid template, the solution further comprising fluorescent species; an illumination system that illuminates the wells through the transparent layer; a detection system that detects emitted light over time from the fluorescent species within the wells, wherein the emitted light passes through the transparent layer; and a computing system that analyzes the emitted light over time in order to obtain sequence information.

In some embodiments the fluorescent species are covalently attached to the nucleotides, and the emitted light over time indicates interactions between the nucleotides and the polymerase enzyme. In some embodiments the nucleotides comprise nucleotide analogs.

In one aspect, the invention comprises a method for producing a zero-mode-waveguide array comprising: providing an electrochemical cell having a working electrode, a counter electrode, and optionally a reference electrode, wherein the working electrode comprises a metallic upper layer of a substrate also having a transparent lower layer, wherein the metallic upper layer comprises an array of apertures extending through metallic upper layer to the transparent lower layer; contacting the working electrode with a solution comprising a phosphorous containing compound; and passing current through the electrochemical cell whereby a phosphorous containing material is deposited onto the metallic upper layer of the substrate.

In some embodiments the zero-mode-waveguide array exhibits improved corrosion resistance compared to a zero-mode-waveguide array not treated by the methods of the invention.

In some embodiments the phosphorous containing compound comprises phosphate or phosphonate functionality. In some embodiments the phosphorous containing compound comprises a polymer. In some embodiments the phosphorous containing compound comprises a polymer having poly (acrylate), poly(sulfonate), or both poly(acrylate) and poly (sulfonate) portions. In some embodiments the phosphorous containing compound comprises polyvinyl phosphonic acid (PVPA), Albritect CP-30, Albritect CP-10, Albritect CP-90, Aquarite ESL, or Aquarite EC4020.

In one aspect, the invention comprises a method for obtaining an island of functionality at the bases of an array of ZMWs comprising: a) providing an electrochemical system comprising a working electrode, a counter electrode, and optionally a reference electrode; b) providing a substrate having a lower transparent layer and an upper cladding layer, wherein the cladding layer comprises an array of apertures disposed through the reflective layer to the transparent layer, the apertures having side walls, wherein the cladding layer comprises the working electrode; c) applying a voltage to the working electrode such that a layer of oxide is formed onto the side walls of the aperture; d) attaching functionalizing agent to exposed regions of the transparent layer within the apertures; and e) dissolving the oxide layer from the walls of the aperture whereby islands of functionalizing agent are formed within the apertures.

In some embodiments the method further comprising step f) of attaching a single molecule of interest to the functionalizing agent on the transparent layer. In some embodiments, step f) is performed after step e). In some embodiments step f) is performed after step d) and before step e).

In some embodiments the single molecule of interest comprises an enzyme or a nucleic acid.

In some embodiments the percentage of aperture having only one single molecule of interest is greater than 37%.

In some embodiments the method further comprises performing steps (a), (b), and (c) again after step (e) whereby a second oxide layer is formed to produce an array of apertures having islands of functionalizing agent and oxide layers on the walls.

In some embodiments step (e) of dissolving the oxide layer is carried out so as to dissolve some of the oxide layer and leave some of the oxide layer undissolved to produce an array of apertures having islands of functionalizing agent and oxide layers on the walls.

In one aspect, the invention comprises a method for producing an array of nanostructures comprising: a) providing a substrate having a top surface, the top surface having an aperture layer, the aperture layer having a plurality of apertures extending through the aperture layer to the substrate, each of the apertures having one or more cross-sectional dimension; b) oxidizing the substrate whereby an oxide layer is formed on the aperture layer, whereby a cross sectional dimension of the apertures is brought to 50 nm or smaller; c) treating the substrate with a functionalizing agent whereby the functionalizing agent becomes attached to the exposed portions of the substrate; d) exposing the substrate to nanostructures to attach the nanostructures to the functionalizing agent attached to the substrate; and e) dissolving the oxide layer.

In some embodiments the nanostructures comprise nanoparticles. In some embodiments, step (d) is performed after step (c) and before step (e). In some embodiments, step (d) is performed after step (e). In some embodiments, in step (b) the cross-sectional dimension is brought to 10 nm or smaller. In some embodiments the aperture layer comprises a metal.

In one aspect, the invention comprises a method for forming an array of nanopores comprising: a) providing a substrate comprising an array of apertures extending therethrough, each of the apertures having one or more cross-sectional dimension; and b) oxidizing the substrate whereby an oxide layer is formed on the substrate and whereby the formed oxide lowers one or more cross sectional dimensions of the apertures to 20 nm or less.

In some embodiments step (b) the formed oxide lowers the aperture dimensions to 5 nm or less. In some embodiments the substrate comprises a metal. In some embodiments the substrate comprises silicon.

In one aspect the invention provides method for producing an island of functionalizing agent in an array of ZMW's comprising: a) providing a substrate having on its surface a cladding layer, wherein the cladding layer comprises an array of apertures disposed through the cladding layer to the substrate, the apertures having side walls; b) selectively growing an aperture constriction layer on the cladding layer such that the aperture constriction layer extends in from the side walls of the aperture to reduce the cross-sectional dimensions of the aperture. c) attaching functionalizing agent to exposed regions of the substrate within the apertures; and d) removing the aperture constriction layer whereby an array of apertures, each having an island of functionalizing agent is produced.

In some embodiments the aperture constriction layer comprises a polymer. In some embodiments the aperture constriction layer comprises a metal oxide.

In some embodiments the aperture constriction layer comprises a metal. In some embodiments the step of selectively growing an aperture constriction layer comprises growing a polymer from the cladding with a polymerization reaction extending from the surface of the cladding. In some embodiments step of selectively growing an aperture constriction layer comprises growing an oxide onto the cladding by connecting the cladding to a voltage source under conditions such that controlled oxidation of the cladding occurs. In some embodiments the step of selectively growing an aperture constriction layer comprises electrodepositing a material onto the cladding by connecting the cladding to a voltage source and providing the current required for electrodeposition.

In some embodiments the substrate comprises a transparent material. In some embodiments the transparent material comprises quartz or fused silica. In some embodiments the substrate comprises silicon. In some embodiments the cladding comprises a metal. In some embodiments the metal comprises aluminum.

In some embodiments the apertures have a cylindrical profile and have a diameter between about 70 nm and 300 nm. In some embodiments the islands have diameter between about 5 nm and about 50 nm.

BRIEF DESCRIPTION OF THE DRAWINGS

FIG. 9 (D)-(E) illustrates the production of oxide on a ZMW structure in which the aperture extends into the transparent substrate.

DETAILED DESCRIPTION OF THE INVENTION

General

In some aspects, the present invention provides optical confinement structures such as zero-mode waveguide (ZMW) structures capable of improved performance. The present invention also provides for arrays of such ZMWs, methods for making and using, and systems incorporating such improved ZMWs. The ZMW structures of the present invention have walls comprising non-reflective material, and in particular, walls comprising a non-reflective material having a higher refractive index than that of the medium within of the ZMW during optical analysis. ZMW structures can be used to analyze solutions containing luminescent species disposed inside or in close proximity to the ZMW. In a ZMW without a non-reflective layer, the solution volume and the ZMW volume, which controls the optical performance, are substantially the same. The use of a ZMW having a layer of non-reflective material on its walls allows for decoupling the volume containing the solution containing the luminescent species from the volume of the ZMW structure that controls the propagation of light. The layer of non-reflective material on the walls can also act to hold or constrain the luminescent species within a region within the center of the ZMW where it can effectively be illuminated and/or detected. In addition, where the walls have a higher refractive index than the medium within the ZMW, the illumination light intensity can be more effectively directed into the portion of the ZMW in which the luminescent species resides. The present invention also provides methods for obtaining islands of functionality within nanoscale apertures and the use of such islands for binding single molecules or single particles within the apertures.

Figure 1:
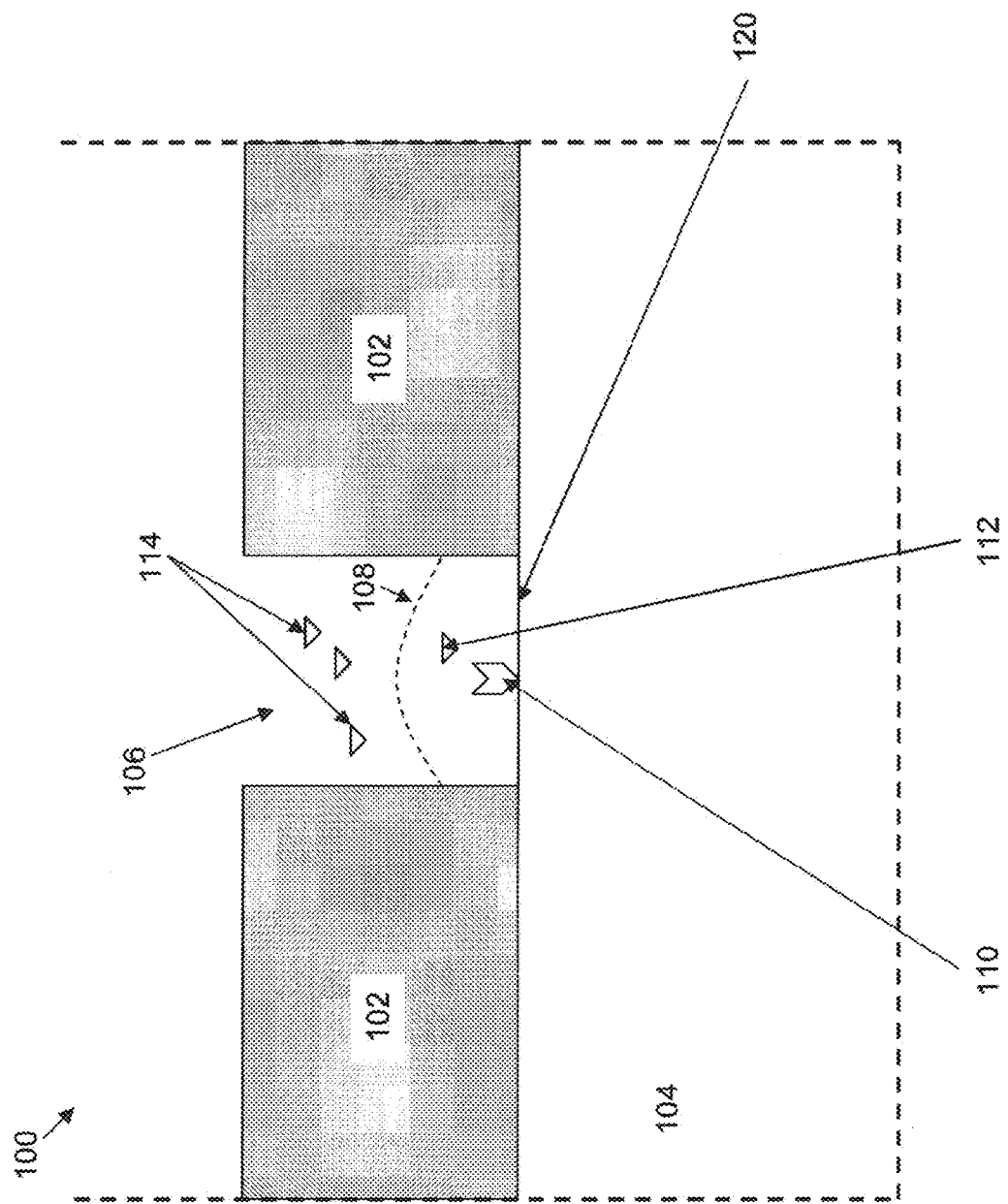
FIG. 1 shows an illustration of a zero-mode-waveguide.

The basic functional structure of a ZMW is schematically illustrated in FIG. 1. As shown, a ZMW structure 100 is provided that includes a cladding layer 102 deposited upon a transparent layer 104. An aperture or core 106 is disposed through the cladding layer to expose the transparent layer 104 below. The aperture 106 has a base 120 that comprises the top surface of the transparent layer 104. As shown in FIG. 1, the base 120 of the aperture 106 is at the same level as the planar surface of the transparent layer 104. In some cases, the base 120 of the aperture 106 is not at the same level, and can be above or below the planar surface of the transparent layer 104 outside of the aperture. For example, in some cases, the base of the aperture can be below the level of the surface of the transparent 104, extending into the transparent layer 104. The core is dimensioned to provide optical confinement by attenuating or preventing propagation of electromagnetic radiation that falls below a cut-off frequency through the core. Instead, the light only penetrates a short distance into the core, illuminating a relatively small volume, indicated as bounded by the dashed line 108. By providing reactants of interest within the observation volume, e.g., enzyme 110 and substrate 112, one can selectively observe their operation without interference from reactants, e.g., substrates 114 outside the observation volume, e.g., above line 108. It will be understood by those in the art the intensity will fall off in the core with a certain function, e.g. exponentially, and that line 108 does not necessarily represent a line above which no light penetrates, but can represent, for example, a line at which the light falls to a certain absolute or relative intensity level.

ZMW structures can be used in order to observe very small quantities of analytes, and have been shown to provide information on the presence and behavior of an analyte to the level of a single molecule. The ability to observe a single molecule in real time allows for carrying out single molecule sequencing, for example single molecule nucleic acid sequencing.

In the context of single molecule nucleic acid sequencing analyses, a single immobilized nucleic acid synthesis complex, comprising a polymerase enzyme, a template nucleic acid, whose sequence one is attempting to elucidate, and a primer sequence that is complementary to a portion of the template sequence, is observed to identify individual nucleotides as they are incorporated into the extended primer sequence. Incorporation is typically monitored by observing an optically detectable label on the nucleotide, prior to, during or following its incorporation. In some cases, such single molecule analyses employ a "one base at a time approach", whereby a single type of labeled nucleotide is introduced to and contacted with the complex at a time. Upon incorporation, unincorporated nucleotides are washed away from the complex, and the labeled incorporated nucleotides are detected as a part of the immobilized complex.

In some instances, only a single type of nucleotide is added to detect incorporation. These methods then require a cycling through of the various different types of nucleotides (e.g., A, T, G and C) to be able to determine the sequence of the template. Because only a single type nucleotide is contacted with the complex at any given time, any incorporation event is by definition, an incorporation of the contacted nucleotide. These methods, while somewhat effective, generally suffer from difficulties when the template sequence includes multiple repeated nucleotides, as multiple bases may be incorporated that are indistinguishable from a single incorporation event. In some cases, proposed solutions to this issue include adjusting the concentrations of nucleotides present to ensure that single incorporation events are kinetically favored.

In other cases, multiple types of nucleotides are added simultaneously, but are distinguishable by the presence on each type of nucleotide of a different optical label. Accordingly, such methods can use a single step to identify a given base in the sequence. In particular, all four nucleotides, each bearing a distinguishable label, is added to the immobilized complex. The complex is then interrogated to identify which type of base was incorporated, and as such, the next base in the template sequence.

In some cases, these methods only monitor the addition of one base at a time, and as such, they (and in some cases, the single nucleotide contact methods) require additional controls to avoid multiple bases being added in any given step, and thus being missed by the detection system. Typically, such methods employ terminator groups on the nucleotide that prevent further extension of the primer once one nucleotide has been incorporated. These terminator groups are typically removable, allowing the controlled re-extension after a detected incorporation event. Likewise, in order to avoid confounding labels from previously incorporated nucleotides, the labeling groups on these nucleotides are typically configured to be removable or otherwise inactivatable.

Figure 2:
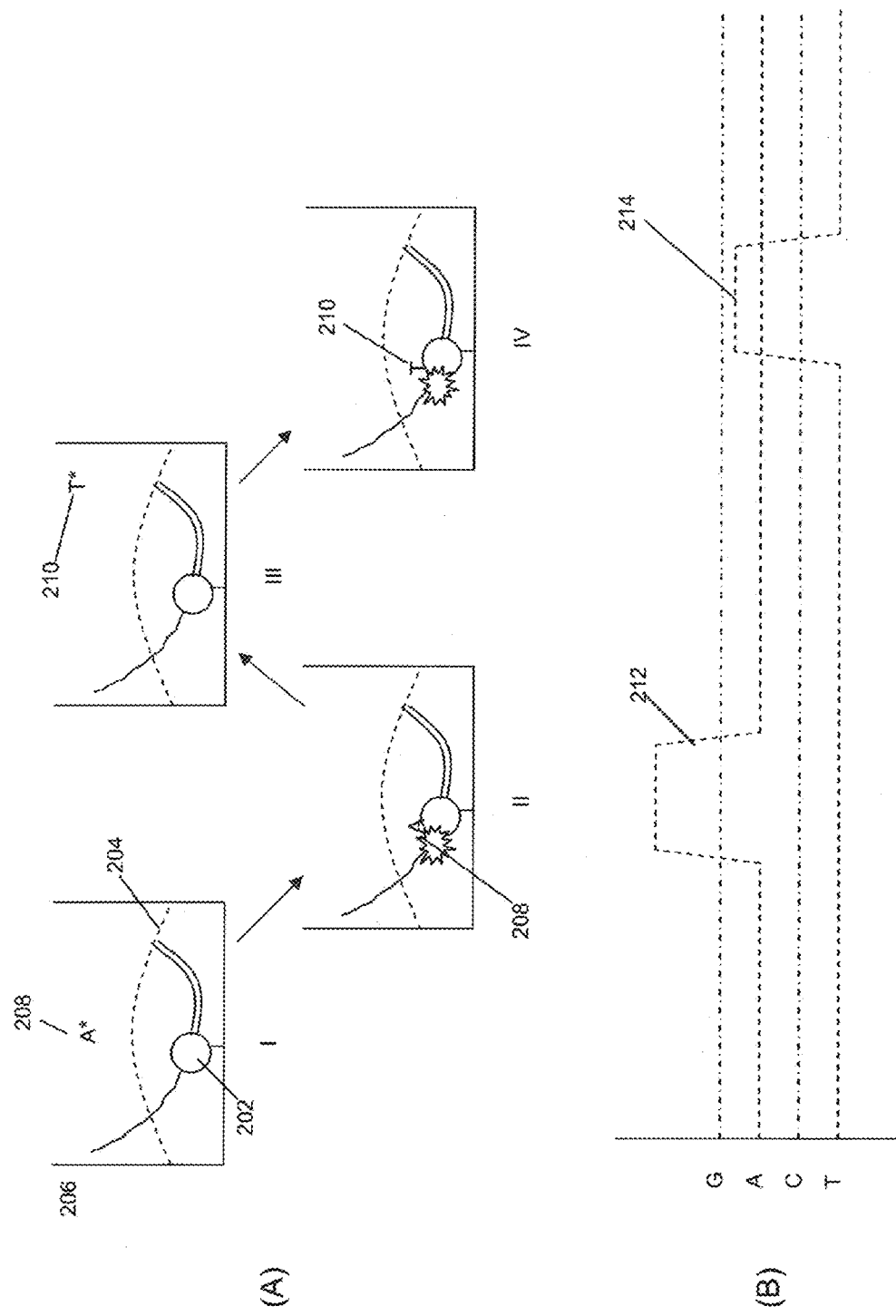
FIG. 2 provides an illustration single molecule nucleic acid sequencing in an optical confinement.

In another process, single molecule primer extension reactions are monitored in real-time, to identify the continued incorporation of nucleotides in the extension product to elucidate the underlying template sequence. In such single molecule real time (or SMRT™) sequencing, the process of incorporation of nucleotides in a polymerase mediated template dependent primer extension reaction is monitored as it occurs. In preferred aspects, the template/polymerase primer complex is provided, typically immobilized, within an optically confined region, such as a zero mode waveguide, or proximal to the surface of a transparent substrate, optical waveguide, or the like (see e.g., U.S. Pat. Nos. 6,917,726, and 7,170,050 and Published U.S. Patent Application No. 2007-0134128, the full disclosures of which are hereby incorporated herein by reference in their entirety for all purposes). The optically confined region is illuminated with an appropriate excitation radiation for the fluorescently labeled nucleotides that are to be used. Because the complex is within an optically confined region, or very small illumination volume, only the reaction volume immediately surrounding the complex is subjected to the excitation radiation. Accordingly, those fluorescently labeled nucleotides that are interacting with the complex, e.g., during an incorporation event, are present within the illumination volume for a sufficient time to identify them as having been incorporated. A schematic illustration of this sequencing process is shown in FIG. 2. As shown in FIG. 2A, an immobilized complex 202 of a polymerase enzyme, a template nucleic acid and a primer sequence are provided within an observation volume (as shown by dashed line 204) of an optical confinement, of e.g., a zero mode waveguide 206. As an appropriate nucleotide analog, e.g., nucleotide 208, is incorporated into the nascent nucleic acid strand, it is illuminated for an extended period of time corresponding to the retention time of the labeled nucleotide analog within the observation volume during incorporation which produces a signal associated with that retention, e.g., signal pulse 212 as shown by the A trace in FIG. 1B. Once incorporated, the label that attached to the polyphosphate component of the labeled nucleotide analog, is released. When the next appropriate nucleotide analog, e.g., nucleotide 210, is contacted with the complex, it too is incorporated, giving rise to a corresponding signal 214 in the T trace of FIG. 213. By monitoring the incorporation of bases into the nascent strand, as dictated by the underlying complementarity of the template sequence, one can obtain long stretches of sequence information of the template. Further, in order to obtain the volumes of sequence information that may be desired for the widespread application of genetic sequencing, e.g., in research and diagnostics, higher throughput systems are desired.

By way of example, in order to enhance the sequencing throughput of the system, multiple complexes are typically monitored, where each complex is sequencing a separate template sequence. In the case of genomic sequencing or sequencing of other large DNA components, these templates will typically comprise overlapping fragments of the genomic DNA. By sequencing each fragment, one can then assemble a contiguous sequence from the overlapping sequence data from the fragments. In preferred aspects, the various different complexes are provided arrayed upon a substrate. Such arrayed complexes may be provided within optically or structurally confined structures, e.g., zero mode waveguides, or they may be patterned on a surface. Alternatively, they may be randomly disposed over a surface but subjected to targeted arrayed illumination, or detection, such that only complexes within an array pattern on the surface are monitored. For purposes of discussion herein, both configurations are referred to herein as the monitoring of arrayed complexes, or the like.

Figure 3:
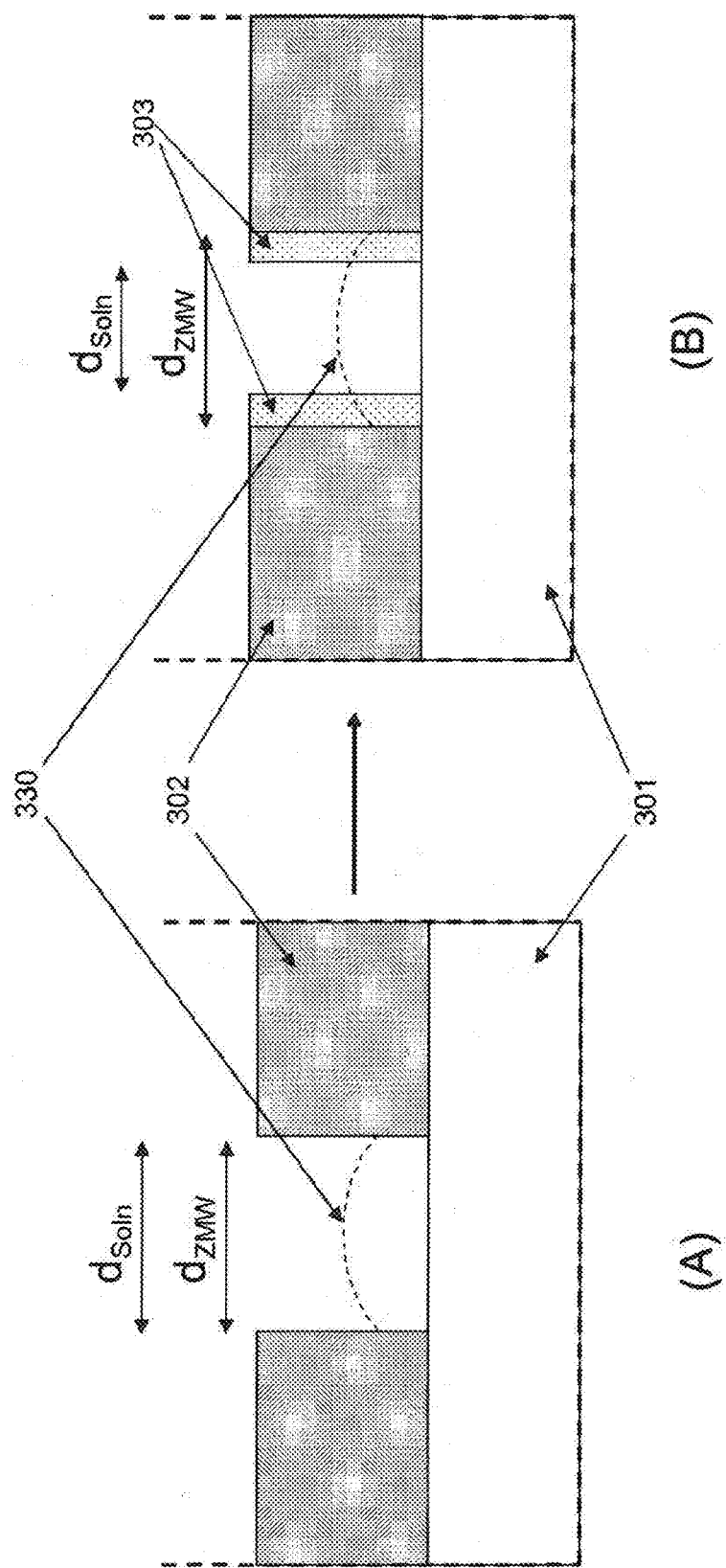
FIG. 3 shows a ZMW with (B) and without (A) a non-reflective layer on its walls.

FIG. 3 illustrates how having non-reflective layers on the walls of the ZMW decouples the solution volume from the ZMW volume. As used herein, the term ZMW volume refers to the volume within the aperture or core which extends through the opaque cladding layer disregarding the non-reflective walls. The solution volume, as used in this context, is the volume that the solution would take up in the ZMW, that is, the volume within the ZMW inside the non-reflective walls. We note that in some cases a ZMW of the invention can be used without a solution present (e.g. detecting a gaseous luminescent species). Thus, the solution volume as used herein may or may not contain a solution. FIGS. 3 (A) and 3(B) represent cross-sections through ZMWs having a cladding layer 302 disposed on a transparent substrate 301. The ZMW in Figure (A) (ZMW(A)) has substantially no non-reflective layer on its walls, thus the cross-sectional dimension of the solution volume ($d_{Soln}$) is substantially the same as the cross sectional dimension of the ZMW ($d_{ZMW}$). Therefore, the cross-sectional area of the solution volume will be substantially the same as the cross-sectional area of the ZMW volume, and the solution volume will be substantially the same as the ZMW volume.

In the ZMW of Figure (B) (ZMW(B), representing a ZMW of the invention, the walls of the ZMW have a non-reflective material disposed upon them. As shown here, the cross-sectional dimension ($d_{ZMW}$) is the same for ZMW(A) and ZMW (B) and thus the cross sectional areas and volumes are also the same. However, by incorporating a non-reflective layer 303 into the inner walls of ZMW(B), the solution cross-sectional dimension ($d_{Soln}$) of ZMW(B) is smaller than the corresponding cross-sectional dimension of ZMW(A), and the solution cross-sectional area and solution volume are smaller in ZMW (B) the corresponding cross-sectional area and solution volume of ZMW(A). The dotted line 330 represents the illuminated region within the ZMW. FIG. 3 illustrates that the illumination region within the ZMW is not substantially changed by the addition of the non-reflective walls. The illumination region will remain unchanged where the refractive index of the material on the walls is the same as the refractive index of the medium within the solution volume. As described in more detail below, where the refractive index of the walls is larger than the refractive index of the medium within the solution volume, the illumination region can change to direct a higher portion of the illumination energy into the region of the solution volume within the ZMW in ways which can be beneficial. We have found that the ability to decouple the solution volume from the ZMW volume in this manner has a number of useful and non-obvious benefits.

Figure 4:
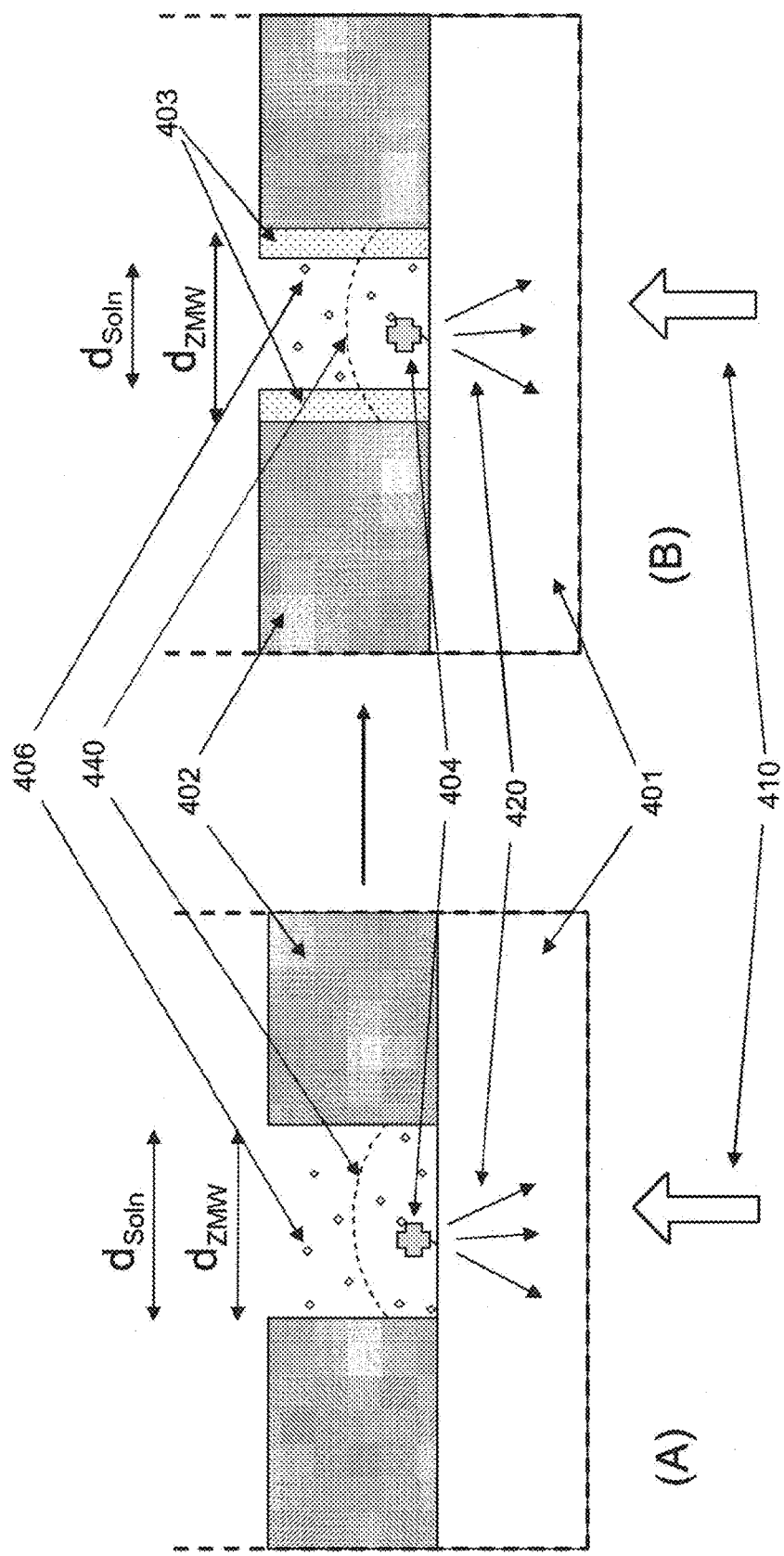
FIG. 4 illustrates optical illumination and detection of a fluorescent species in a ZMW with (B) and without (A) a non-reflective layer on its walls.

One advantage of the ZMW of the present invention is a reduction in the level of background light, for example background fluorescence, from the solution. This benefit can be seen by referring to FIG. 4, in which, similar to FIG. 3, ZMW(B) has a non-reflective layer on the walls, and thereby has a smaller solution cross-sectional area and a smaller solution volume than ZMW(A), but ZMW(A) and ZMW(B) have the same geometry with respect to the opaque layer: i.e. ZMW(A) and ZMW(B) each have the same ZMW cross-sectional area and the same ZMW volume. FIG. 4 represents a ZMW used within a system in which fluorescence is used to analyze molecules within the ZMW. The illumination (or excitation) light 410 is introduced from below, through the transparent substrate 401 into the ZMW. Fluorescent species within the ZMW that interact with the illumination light may emit fluorescent emitted light 420, which can be detected from below the transparent layer with a detector. In FIG. 4, the ZMW's have bound to the transparent substrate 401 a single molecule 404 such as a single nucleic acid polymerase molecule used for single molecule sequencing as described herein. In addition, the ZMW's have in solution background fluorescent species 406 which are capable of emitting fluorescent light. This background fluorescent light is generally undesirable as the background light generally does not provide useful information to the analysis, and such light observed by the detector can contribute to the noise in the system. As is illustrated in FIG. 4, since the solution volume in ZMW(B) is smaller than the solution volume in ZMW(A), the number of background fluorescent species will be smaller, and therefore the background fluorescent light will be lower in ZMW(B), resulting in a higher signal-to-noise ratio (SNR) for detection of the fluorescent signals of interest, such as fluorescent signals associated with molecules bound by a polymerase enzyme within the observation region.

The comparison of ZMW's with and without a non-reflective layer made in reference to FIGS. 3 and 4 compare structures with the same ZMW dimensions and a smaller solution volume. The benefits of the non-reflective layer can be further appreciated by considering two structures, each having the same solution volume but one having a non-reflective layer and one having no such layer. In this case, the ZMW structure with the non-reflective layer will have a ZMW with a larger cross section. The use of a ZMW with a larger cross-section can be beneficial in increasing the level of emission from a luminescent species within the solution volume. Controlling this effect can be particularly useful, for example, when analyzing a reaction having multiple luminescent species, such as a nucleic acid sequencing reaction having multiple fluorescently labeled nucleotides. The optical characteristics of a given ZMW can vary with the wavelength of the light that is interacting with the ZMW, either the illumination or the emission light. The ZMW structures of the invention thus allow for independently tuning the waveguide portion and the solution containing portion of the ZMW structure.

Another advantage of the ZMW of the present invention is that the solution volume is moved into the center of the ZMW and away from the walls. The placement of the luminescent species of interest toward the center of the ZMW and away from the walls can be useful for several reasons. One reason is that the illumination light can be of higher intensity and higher consistency toward the middle of the ZMW. Another is that the collection of emitted light can be more effective for an emitting species when it is away from the walls. It is known, for example, that a fluorescent species can have its fluorescence significantly attenuated, and in some cases completely quenched when it is positioned very near or directly on a reflective surface such as the surface of a metal. Thus the non-reflective material keeps the emitting species away from the walls where its emission can more effectively detected.

Figure 5:
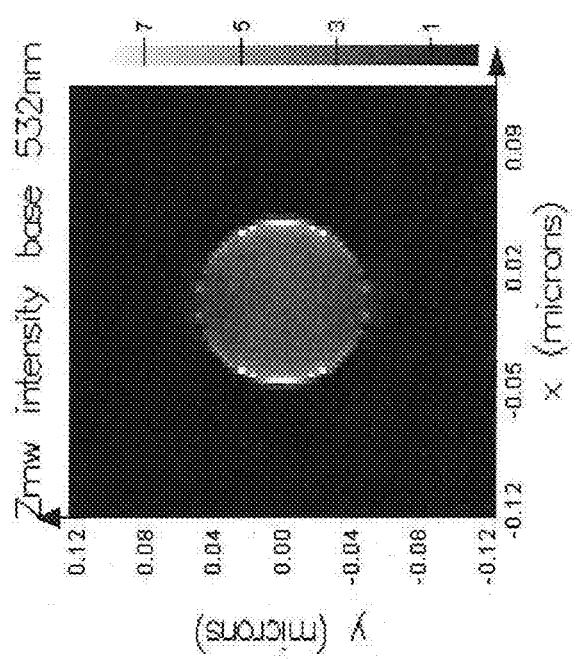
FIG. 5 shows an optical model of illumination intensity at the base of a ZMW without a reflective layer on its walls.

Having a fluorescent species of interest away from the walls can also be important in order to avoid having the fluorescent species in areas where there are areas of very high illumination intensity, or illumination "hot spots". We have found by optical modeling of the ZMW that illumination hot spots can occur at the edges of the ZMW such as edges at the base of the ZMW where the wall meets the transparent substrate. FIG. 5 shows a result of such optical modeling for a ZMW without a non-reflective layer on its walls. The ZMW in FIG. 5 has a fused silica transparent substrate with a refractive index of about 1.46, and an aluminum cladding layer with a thickness of 110 nm. The ZMW is cylindrical aperture having a diameter of 100 nm. The ZMW is filled with an aqueous medium having a refractive index of about 1.33. The ZMW is illuminated through the transparent substrate with 532 nm light polarized in the x-direction. FIG. 5 shows 2-dimensional plot of intensity versus position along the base of the ZMW. The higher the intensity, the lighter the color, consistent with the scale shown on the right side of the figure.

As can be seen in FIG. 5, the optical modeling shows high intensity hot spots at the edges of the ZMW at its base. A fluorescent species in the region of the hot spot would experience very high light intensity. In addition, and for the reasons described above, the fluorescent emission of this fluorescent species can be attenuated or quenched due to its proximity to the reflective cladding.

Figure 6:
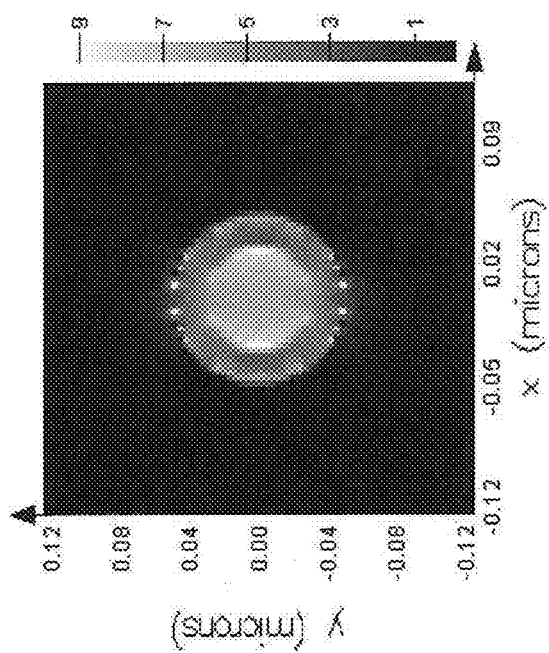
FIG. 6 shows an optical model of illumination intensity at the base of a ZMW having a reflective layer on its walls.

FIG. 6 shows the optical modeling results for the same ZMW as in FIG. 5, but having a 20 nm thick layer of a non-reflective material with a refractive index of about 2.5 on the ZMW walls. FIG. 6 shows that the solution volume region inside of the non-reflective material layer is not exposed to the hot spots as was the case for the solution volume in FIG. 5. It is well known that photodamage to luminescent species within the ZMW can inhibit the performance of the ZMW. Such photodamage can, for example, inhibit or destroy the activity of a polymerase enzyme used for nucleic acid sequencing. Thus, eliminating hot-spots, and controlling the illumination intensity within the ZMW can provide significant improvements in the quality of sequencing data obtained from reactions carried out within the ZMW.

FIG. 6 also illustrates an advantage of having non-reflective walls with a higher refractive index than that of the medium within the solution volume. It can be seen in FIG. 6 that the intensity of the light within the solution region is generally higher than the intensity in the regions of the non-reflective layers. The relative intensity of light in the non-reflective layer and the light in the solution region can be controlled by controlling the relative refractive indices of the medium in the solution volume and the non-reflective layers. Generally, the higher the ratio of wall refractive index to solution refractive index, the more light intensity which will be directed into the solution volume. FIG. 6 shows that the illumination light intensity is concentrated into the region inside the non-reflective walls of higher refractive index at the base of the ZMW. Optical modeling shows that there can be a benefit of increased illumination intensity also for structures where the aperture within the ZMW extends into the transparent substrate, for example for the structures such as that shown in FIG. 7(E).

ZMW with Non-Reflective Layers on the Walls

Zero mode waveguides (ZMWs) are generally characterized by the existence of a core surrounded by a cladding, where the core is dimensioned such that it precludes a substantial amount of electromagnetic radiation that is above a cut-off frequency from propagating through the core. As a result, when illuminated with light of a frequency below the cutoff frequency, the light will only penetrate a short distance into the core, effectively illuminating only a small fraction of the core's volume. In accordance with the present invention, the ZMW core comprises an empty or preferably fluid filled cavity surrounded by a non-reflective layer and then the cladding layer. This core then provides a zone or volume in which a chemical, biochemical, and/or biological reaction may take place that is characterized by having an extremely small volume, which can be used to effectively observe a single molecule or set of reacting single molecules. ZMWs, their fabrication, structure, and use in analytical operations are described in detail in U.S. Pat. No. 6,917,726 and Levene, et al., Science 299(5607):609-764 (2003), the full disclosures of which are hereby incorporated herein by reference in their entirety for all purposes.

In the context of chemical or biochemical analyses within ZMWs as well as other optical confinements, it is clearly desirable to ensure that the reactions of interest are taking place within the optically interrogated portions of the confinement, at a minimum, and preferably such that only the reactions of a single molecule is occurring within an interrogated portion of an individual confinement. A number of methods may generally be used to provide individual molecules within the observation volume. A variety of these are described in co-pending U.S. patent application Ser. No. 11/240,662, filed Sep. 30, 2005, incorporated herein by reference in its entirety for all purposes, which describes, inter alia, modified surfaces that are designed to immobilize individual molecules to the surface at a desired density, such that approximately one, two, three or some other select number of molecules would be expected to fall within a given observation volume. Typically, such methods utilize dilution techniques to provide relatively low densities of coupling groups on a surface, either through dilution of such groups on the surface or dilution of intermediate or final coupling groups that interact with the molecules of interest, or combinations of these.

One aspect of the invention is a zero-mode waveguide structure comprising: a transparent substrate having a top surface; an opaque layer disposed upon the top surface of the transparent substrate; an array of apertures extending through the opaque layer to the transparent substrate wherein the apertures comprise wells having walls and bases, the bases of the wells comprising portions of the top surface of the transparent substrate; and a non-reflective layer disposed on the walls of the wells wherein the thickness of the non-reflective layer is greater than about 5 nm. In some cases the non-reflective layer is disposed on the walls of the wells wherein the thickness of the non-reflective layer is greater than about 10% of the largest cross-sectional dimension of the wells.

Typically, the ZMW aperture has at least one cross-sectional dimension, e.g., diameter, which is sufficiently small that light entering the waveguide is prevented in some measure from propagating through the core, effectively resulting in a very small portion of the core and its contents being illuminated, and/or emitting optical signals that exit the solution volume of the core. In the case of optical signals (and excitation radiation), the ZMW cores will typically be between about 1 nm and about 300 nm, between about 10 and about 200 nm, or between about 50 and about 150 nm in diameter where light in the visible range is used.

The individual confinement in the array can provide an effective observation volume less than about 1000 zeptoliters, less than about 900, less than about 200, less than about 80, less than about 10 zeptoliters. Where desired, an effective observation volume of less than 1 zeptoliter can be provided. In a preferred aspect, the individual confinement yields an effective observation volume that permits resolution of individual molecules, such as enzymes, present at or near a physiologically relevant concentration. The physiologically relevant concentrations for many biochemical reactions range from micro-molar to millimolar because most of the enzymes have their Michaelis constants in these ranges. Accordingly, a preferred array of optical confinements has an effective observation volume for detecting individual molecules present at a concentration higher than about 1 micromolar (µM), or more preferably higher than 50 µM, or even higher than 100 µM.

A zero-mode-waveguide can provide an optical guide in which the majority of incident radiation is attenuated, preferably more than 80%, more preferably more than 90%, even more preferably more than 99% of the incident radiation is attenuated. As such high level of attenuation, no significant propagating modes of electromagnetic radiation exist in the guide. Consequently, the rapid decay of incident electromagnetic radiation at the entrance of such guide provides an extremely small observation volume effective to detect single-molecules, even when they are present at a concentration as high as in the micromolar range.

The ZMW internal cavity (i.e., the core) surrounded by the cladding may adopt a convenient size, shape or volume so long as propagating modes of electromagnetic radiation in the guide is effectively prevented. The core typically has a lateral dimension less than the cutoff wavelength ($\lambda_c$). For a circular guide of diameter d and having a clad of perfect conductor, $\lambda_c$ is approximately 1.7 times d. The cross sectional area of the core may be circular, elliptical, oval, conical, rectangular, triangular, polyhedral, or in any other shape. Although uniform cross sectional area is generally preferred, the cross sectional area may vary at any given depth of the guide if desired. For example, in some cases the ZMW has a conical shape. The shape of the ZMW core, and the shape of the solution volume are generally similar, but in some cases they can be different. For example, in some embodiments, the ZMW core is cylindrical, and the shape of the solution volume defined by non-reflective walls is conical.

In some embodiments, the ZMW core is non-cylindrical. In one aspect of this embodiment, a non-cylindrical core comprises an opening on the upper surface and a base at the bottom surface, wherein the opening is narrower in lateral dimension than the base. In another aspect, the opening at the base is narrower than the opening at the surface. This configuration significantly restricts the diffusion of reactants, and hence increases the average residence time in the observation volume. Such configuration can be useful, for example, for measuring the association rate constant (on-rate) of a chemical reaction. In another aspect, the core comprises an opening that is wider in lateral dimension than the base. Such configuration allows easier access to large molecules that impose a steric or entropic hindrance to entering the structure if the open end of the zero mode waveguide was as small as the base needed to be for optical performance reasons. Examples include the accessibility for long strand polyelectrolytes such as DNA molecules that are subject to entropic forces opposing entry into small openings.

Figure 7:
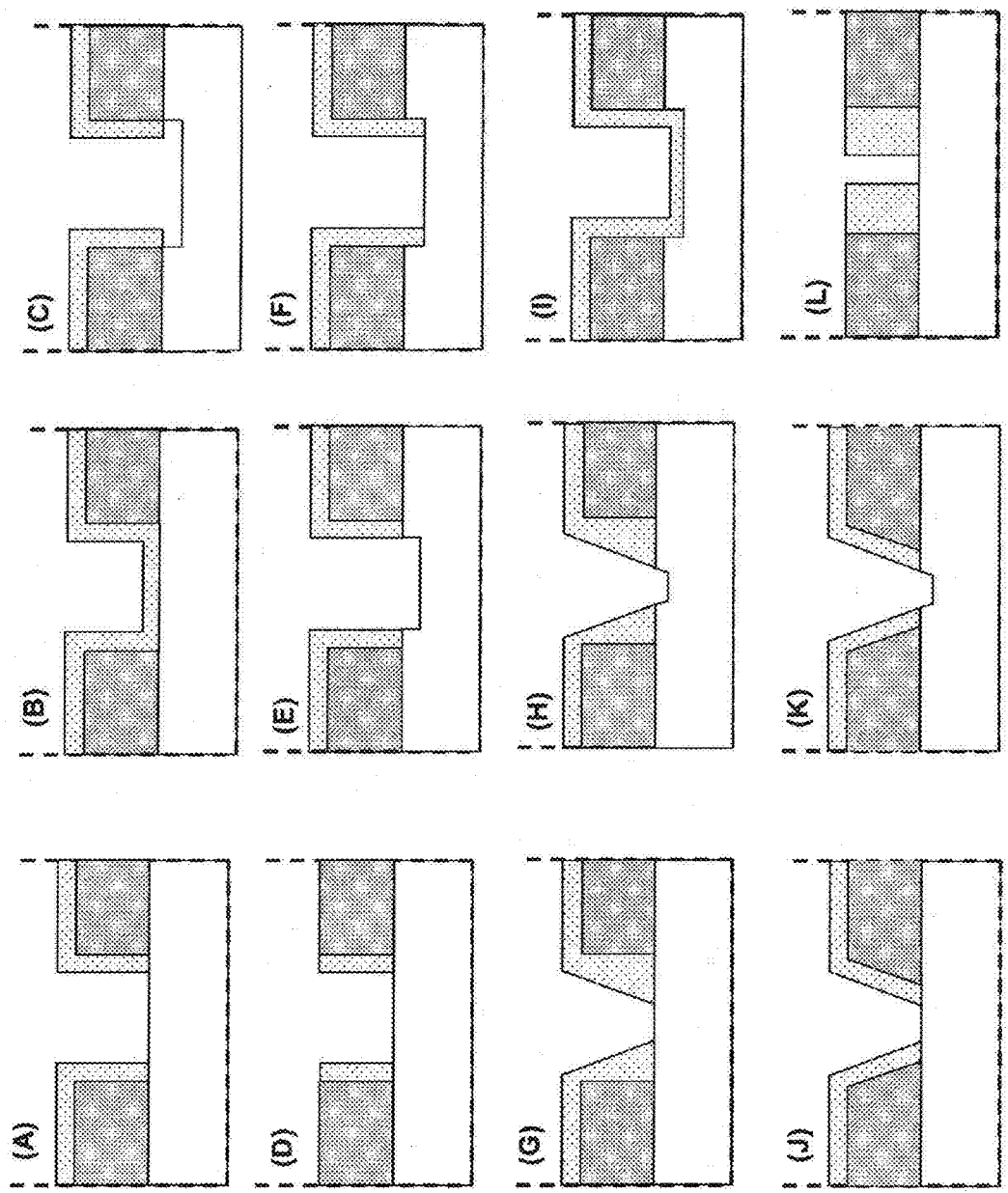
FIG. 7 shows cross-sections of some exemplary ZMWs of the invention having non-reflective layers on their walls.

FIG. 7 shows cross-sections of some specific embodiments of ZMW structures having non-reflective layers on their walls. The ZMW shown in FIG. 7(A) has a layer of non-reflective material on the walls of the ZMW aperture and also on the top of the cladding layer. In some cases, the cross sections represent an aperture with a circular profile. The cross-sections can also represent profiles with other shapes including a slit, ellipse, rectangle, star, or any other suitable shape. This type of structure can result, for example, where the non-reflective layer comprises an oxide that is specifically grown onto a metal cladding layer, e.g. by thermal or electrochemical oxidation. The structure can also be produced by selective deposition onto the cladding layer or by first conformally coating the non-reflective material and second, removing the portion of the non-reflective material on the transparent substrate. In the ZMW shown in FIG. 7(B), the non-reflective layer covers the walls of the ZMW, the top of the cladding, and the top of the transparent substrate within the ZMW. This type of structure can be created, for example, by conformally coating a ZMW structure with a non-reflective material. In some cases, as shown in FIG. 7(C), the ZMW aperture will extend into the transparent substrate, and the non-reflective layer will be specifically on the opaque cladding layer, in some cases extending over the a portion of the aperture that extends into the transparent substrate. FIG. 7 (D) shows a ZMW in which the non-reflective layer is only on the inside walls of the ZMW, and not on the top of the surface of the cladding. In FIG. 7(E) the portion of the aperture that can hold the solution extends into the transparent substrate and the non-reflective layer does not extend over the portion that extends into the transparent substrate.

FIG. 7(F) shows a ZMW in which the ZMW aperture extends into the transparent substrate and the non-reflective layer extends into the portion of the aperture that extends into the transparent substrate. In FIG. 7(G) the ZMW aperture has straight side walls (which for a ZMW with a spherical cross section would constitute a cylinder), and the non-reflective layer is applied so as to have angled side-walls (which, for a solution volume with a spherical cross section would constitute a conical structure). FIG. 7(H) is similar to FIG. 7(G), but in which the solution containing portion extends into the transparent layer. In Figure (I), the ZMW aperture extends into the transparent substrate, and the non-reflective layer coats the inside walls of the ZMW, the base of the ZMW, and the top surface of the cladding layer. In Figure (J), the ZMW has angled sidewalls (which for a ZMW with a cylindrical cross section would constitute a conical structure), and the non-reflective layer also has angled sidewalls. FIG. 7(K) shows a ZMW similar to that in FIG. 7(J), but with the solution containing portion extending into the transparent layer. The ZMW of FIG. 7(L) is similar to that of FIG. 7(D), but having a non-reflective layer which is thicker. FIG. 7(L) illustrates that the methods of the invention can be used to lower the solution volume significantly and also to position a luminescent species at or near the center of the ZMW. It will be appreciated by those skilled in the art that the ZMW of the invention can be comprise a combination of two or more of the structures shown in FIG. 7.

The height of the ZMW will generally be the thickness of the cladding layer, and the ZMW aperture may extend into the transparent layer. The height of the ZMW can be between about 5 nm and 500 nm, between 20 nm and 300 nm, or between 50 nm and 150 nm. In some cases, the height of the ZMW is between about 80 nm and 140 nm.

The thickness of the non-reflective layer will generally be greater than about 5 nm. It is known, for example, that the native oxide layer on the surface of an aluminum metal can have a thickness of between about 3 to 4 microns. The thickness of the non-reflective layer will generally be greater than the thickness of this native oxide coating. It will be understood that the best thickness can depend on the diameter of the ZMW that is used and the use to which the ZMW is put. In some cases, for example, while a greater thickness of the non-reflective layer may be useful for improved optical properties, the greater thickness may result in a solution volume which is too small to accommodate the species to be analyzed, for example, the enzyme and/or its substrate. The structures and methods of the invention allow for adjusting the thickness of the non-reflective layer and the dimensions of the ZMW in order to improve the overall performance of the system which incorporates the ZMW, for example the analysis of biomolecules and nucleic acid sequencing.

In some cases, the non-reflective coating has a thickness of between about 5 nm and about 50 nm, between about 8 nm and 40 nm, and between about 10 nm and about 30 nm. In some cases, a ZMW having a cross-sectional dimension of about 50 nm to about 105 nm has a non-reflective coating of about 10 nm to about 30 nm of thickness. The thickness of the non-reflective layer is generally maintained such that a solution volume is maintained inside of the ZMW.

The non-reflective layer will generally result in a cross-sectional dimension within the non-reflective layer being less than the corresponding cross-sectional dimension of the ZMW. For the ZMW's of the invention, the solution volume within the non-reflective area of the ZMW will have a cross-sectional dimension that is about 10% to about 95%, from about 20% to about 80%, or between about 25% to about 50% of the corresponding cross-sectional dimension of the ZMW. Where the ZMW and the solution volume within the non-reflective layer in the ZMW each comprise cylindrical structures with circular cross sections, for example, the cross-sectional dimension would be the diameter of the circular cross-section. In some cases the cross-sectional dimensions will vary with height, in which case the average or median cross-sectional dimension can be used. In other cases, the cross-sectional dimension at a given height, such as at the base of the ZMW can be used.

The non-reflective coating will take up a portion of the cross-sectional area which would be available to a solution if the non-reflective layer was not present, thus lowering the solution volume within the ZMW. In some cases, the ZMW of the invention will have a cross-sectional area inside the non-reflective layer (the solution volume) that comprises from about 10% to about 90%, from about 30% to about 80%, or between about 30% to about 50% of the corresponding cross-sectional area of the ZMW. The cross-sectional area of a ZMW may vary with height. In some cases, the average or median cross sectional area of the ZMW is used to determine the relative amount of the non-reflective layer. In some cases, the relative cross sectional areas at a given height, such as at the base of the ZMW can be used.

The non-reflective layer results in a solution volume within the non-reflective layer in the ZMW that is smaller than the ZMW volume. In some cases, the ZMW of the invention will have a volume inside the non-reflective layer (the solution volume) that comprises between about 10% to about 90%, between about 30% to about 80%, or between about 30% to about 50% of the ZMW volume.

The cladding is typically made of materials that prevent any significant penetration of the electric and the magnetic fields of an electromagnetic radiation that is opaque and/or reflective materials. Suitable materials for fabricating the cladding include but are not limited to metals, metal oxides, alloys, conducting materials and semi-conducting materials, and any combination thereof. The cladding layer can comprise a metal such as aluminum, copper, gold, silver, chromium, titanium or mixtures thereof.

The transparent substrate can comprise inorganic materials, organic materials, or composite materials with both organic and inorganic materials. The transparent material is typically a rigid material which can keep the reactive regions in fixed positions during observation. Silica based materials, such fused silica are preferred materials, for example, where semiconductor or MEMS processing methods are used to produce the micromirror arrays. The transparent substrate may also comprise inorganic oxide materials and glasses. The transparent substrate material may be a heterogeneous material, such as a material having multiple layers. In some cases, for example, the transparent substrate may comprise a dielectric stack. Transparent polymeric materials can also be used. It is typically desired that the transparent material exhibit low levels of autofluorescence. Suitable transparent polymers comprise, for example, methacrylate polymers such as PMMA, polycarbonates, cyclic olefin polymers, sytrenic polymers, fluorine-containing polymers, polyesters, polyetherketones, polyethersulfones, polyimides or mixtures thereof.

The non-reflective layer on the walls of the ZMW is generally transparent to the light at the wavelength at which the ZMWs are used, so can also be referred to as non-opaque materials. While generally transparent, the non-reflective layers need not be completely transparent, and could be, for instance translucent. The non-reflective layer can be made of any suitable material that is generally transparent to the light used with the ZMW. The non-reflective layer material can be inorganic or organic. In some cases, the non-reflective layer comprises an oxide or a nitride. Suitable oxides include oxides of aluminum, titanium, zinc, chromium, nickel, molybdenum, silver, magnesium, cesium, hafnium, zirconium, and silicon. In some cases, oxides of aluminum are used. As described in more detail below, in some cases the non-reflective layer comprises an oxide of a metal which comprises the opaque cladding layer. Sol-gel materials can be used to form the non-reflective layer, often composed largely of silicon oxides with smaller amounts of other oxides. Polymeric materials can comprise the non-reflective layer. Such polymers can be either largely carbon based or silicon based. Suitable polymers include acrylates, methacrylates, polyimides, polyamides, polyketones, polysulfones, polyesters, cellulose based polymers, polycarbonates, cyclic olefin polymers, sytrenic polymers, fluorine-containing polymers, polyetherketones, polyethersulfones, polydimethylsiloxane (PDMS), poly(methyl methacrylate) (PMMA), and the like. Mixtures and copolymers of the above polymers can also be used.

As described above, it can be advantageous that the non-reflective layer have a higher refractive index than that of the medium in the solution volume of the ZMW. We have shown by optical modeling that by having a higher refractive index than the medium in the solution volume, a higher proportion of illumination light is directed to the solution volume than if the non-reflective layer had the same or a lower refractive index than the medium in the solution volume. In many cases, an aqueous medium is in the solution volume during analysis, generally having a refractive index of about 1.3. While it is beneficial to have a refractive index greater than the medium within the solution volume, it is not necessarily advantageous to have the highest refractive index possible in order, for example, to control hot spots. In some cases, the non-reflective material has a refractive index of between about 1.4 and about 5.0, between about 1.5 and about 3.0. In some cases, the non-reflective material has a refractive index between about 1.7 and about 2.6.

The ZMW's of the invention are particularly useful when employed as a an array of ZMW's, allowing for parallel analysis of multiple luminescent species at one time; for example, multiple nucleic acid sequencing reactions.

The overall size of the array can generally range from a few nanometers to a few millimeters in thickness, and from a few millimeters to 50 centimeters in width and/or length. Arrays may have an overall size of about few hundred microns to a few millimeters in thickness and may have any width or length depending on the number of optical confinements desired.

The spacing between the individual confinements can be adjusted to support the particular application in which the subject array is to be employed. For instance, if the intended application requires a dark-field illumination of the array without or with a low level of diffractive scattering of incident wavelength from the optical confinements, then the individual confinements may be placed close to each other relative to the incident wavelength.

Where the substrates comprise arrays of optical confinements, the arrays may comprise a single row or a plurality of rows of optical confinement on the surface of a substrate, where when a plurality of lanes are present, the number of lanes will usually be at least 2, more commonly more than 10, and more commonly more than 100. The subject array of optical confinements may align horizontally or diagonally long the x-axis or the y-axis of the substrate. The individual confinements can be arrayed in any format across or over the surface of the substrate, such as in rows and columns so as to form a grid, or to form a circular, elliptical, oval, conical, rectangular, triangular, or polyhedral pattern. To minimize the nearest-neighbor distance between adjacent optical confinements, a hexagonal array is sometimes preferred. The array need not be in rows or columns, and can be placed in any arbitrary pattern.

The array of optical confinements may be incorporated into a structure that provides for ease of analysis, high throughput, or other advantages, such as in a microtiter plate and the like. Such setup is also referred to herein as an "array of arrays." For example, the subject arrays can be incorporated into another array such as microtiter plate wherein each micro well of the plate contains a subject array of optical confinements.

In accordance with the invention, arrays of confinements or zero mode waveguides, are provided in arrays of more than 100, more than 1000, more than 10,000, more that 100,000, or more than 1,000,000 separate waveguides on a single substrate. In addition, the waveguide arrays typically comprise a relatively high density of waveguides on the surface of the substrate. Such high density typically includes waveguides present at a density of greater than 10 zero mode waveguides per $mm^2$, preferably, greater than 100 waveguides per $mm^2$ of substrate surface area, and more preferably, greater than 500 or even 1000 waveguides per $mm^2$ and in many cases up to or greater than 100,000 waveguides per $mm^2$. Although in many cases, the waveguides in the array are spaced in a regular pattern, e.g., in 2, 5, 10, 25, 50 or 100 or more rows and/or columns of regularly spaced waveguides in a given array, in certain preferred cases, there are advantages to providing the organization of waveguides in an array deviating from a standard row and/or column format. In preferred aspects, the substrates include zero mode waveguides as the optical confinements to define the discrete reaction regions on the substrate.

The ZMW arrays of the invention can be incorporated into substrates having micromirror structures, for example having one micromirror per ZMW array for more effectively guiding the illumination light to the array and/or guiding the emitted light from the array to a detector. Such micromirror structures are described, for example, in U.S. Provisional Patent Application 61/223,628, filed Jul. 7, 2009.

Apparatus/System

The invention also provides for systems and for apparatus that are used in conjunction with the ZMW's and ZMW arrays of the invention to provide real-time analytical information on optical systems having luminescent species down to the single-molecule level. In particular, such systems typically include the reagent systems, in conjunction with an analytical system, e.g., for detecting data from those reagent systems. In certain preferred embodiments, analytical reactions are monitored using an optical system capable of detecting and/or monitoring interactions between reactants at the single-molecule level. For example, such an optical system can achieve these functions by first generating and transmitting an incident wavelength to the reactants, followed by collecting and analyzing the optical signals from the reactants. Such systems typically employ an optical train that directs signals from a plurality of reactions disposed on a solid surface having an array of ZMW structures of the invention onto different locations of an array-based detector to simultaneously detect multiple different optical signals from each of multiple different reactions. The optical trains can include optical gratings or wedge prisms to simultaneously direct and separate signals having differing spectral characteristics from each confinement in an array to different locations on an array based detector, e.g., a CCD, and may also comprise additional optical transmission elements and optical reflection elements.

One aspect of the invention comprises an apparatus for obtaining nucleic acid sequence information comprising: a zero-mode waveguide array structure with a transparent substrate having a top surface, and a reflective layer disposed upon the top surface of the transparent substrate; an array of apertures extending through the reflective layer to the transparent substrate wherein the apertures comprise wells having walls and bases, the bases of the wells comprising portions of the top surface of the transparent layer; and a non-reflective layer disposed on the walls of the wells wherein the thickness of the non-reflective layer is greater than about 5 nm. The zero-mode waveguide structure is incorporated into a device configured to hold an analysis solution in contact with the zero-mode waveguide structure, whereby the wells comprise the analysis solution which comprises reagents for carrying out reactions for which nucleic acid sequence information can be derived; including polymerase enzyme, nucleotides, and nucleic acid template, the solution further comprising fluorescent species. The system has: an illumination system that illuminates the wells through the transparent layer; a detection system that detects emitted light over time from the fluorescent species within the wells, wherein the emitted light passes through the transparent layer; and a computing system that analyzes the emitted light over time in order to obtain sequence information.

An optical system applicable for use with the present invention preferably comprises at least an excitation source and a photon detector. The excitation source generates and transmits incident light used to optically excite the reactants in the reaction. Depending on the intended application, the source of the incident light can be a laser, laser diode, a light-emitting diode (LED), a ultra-violet light bulb, and/or a white light source. Further, the excitation light may be evanescent light, e.g., as in total internal reflection microscopy, certain types of waveguides that carry light to a reaction site (see, e.g., U.S. Application Pub. Nos. 20080128627, 20080152281, and 200801552280), or zero mode waveguides, described below. Where desired, more than one source can be employed simultaneously. The use of multiple sources is particularly desirable in applications that employ multiple different reagent compounds having differing excitation spectra, consequently allowing detection of more than one fluorescent signal to track the interactions of more than one or one type of molecules simultaneously. A wide variety of photon detectors or detector arrays are available in the art. Representative detectors include but are not limited to an optical reader, a high-efficiency photon detection system, a photodiode (e.g. avalanche photo diodes (APD)), a camera, a charge-coupled device (CCD), an electron-multiplying charge-coupled device (EMCCD), an intensified charge coupled device (ICCD), and a confocal microscope equipped with any of the foregoing detectors. For example, in some embodiments an optical train includes a fluorescence microscope capable of resolving fluorescent signals from individual sequencing complexes. Where desired, the subject arrays of optical confinements contain various alignment aides or keys to facilitate a proper spatial placement of the optical confinement and the excitation sources, the photon detectors, or the optical train as described below.

The subject optical system may also include an optical train which can have multiple functions and may comprise one or more optical transmission or reflection elements. Such optical trains preferably encompass a variety of optical devices that channel light from one location to another in either an altered or unaltered state. First, the optical train collects and/or directs the incident wavelength to the reaction site comprising a ZMW structure of the invention. Second, the optical train transmits and/or directs the optical signals emitted from the reactants to the photon detector. Third, the optical train may select and/or modify the optical properties of the incident wavelengths or the emitted wavelengths from the reactants. Illustrative examples of such optical transmission or reflection elements are diffraction gratings, arrayed waveguide gratings (AWG), optical fibers, optical switches, mirrors (including dichroic mirrors), lenses (including microlenses, nanolenses, objective lenses, imaging lenses, and the like), collimators, optical attenuators, filters (e.g., polarization or dichroic filters), prisms, wavelength filters (low-pass, band-pass, or high-pass), planar waveguides, wave-plates, delay lines, and any other devices that guide the transmission of light through proper refractive indices and geometries. One example of a preferred optical train is described in U.S. Patent Pub. No. 20070036511, filed Aug. 11, 2005, and incorporated by reference herein in its entirety for all purposes.

The reaction site, comprising a ZMW structure of the invention, containing a reaction of interest can be operatively coupled to a photon detector. The reaction site and the respective detector can be spatially aligned (e.g., 1:1 mapping) to permit an efficient collection of optical signals from the reactants. In certain preferred embodiments, a reaction substrate is disposed upon a translation stage, which is typically coupled to appropriate robotics to provide lateral translation of the substrate in two dimensions over a fixed optical train. Alternative embodiments could couple the translation system to the optical train to move that aspect of the system relative to the substrate. For example, a translation stage provides a means of removing a reaction substrate (or a portion thereof) out of the path of illumination to create a non-illuminated period for the reaction substrate (or a portion thereof), and returning the substrate at a later time to initiate a subsequent illuminated period. An exemplary embodiment is provided in U.S. Patent Pub. No. 20070161017, filed Dec. 1, 2006.

Each individual reaction region can be operatively coupled to a respective microlens or a nanolens, preferably spatially aligned to optimize the signal collection efficiency. Alternatively, a combination of an objective lens, a spectral filter set or prism for resolving signals of different wavelengths, and an imaging lens can be used in an optical train, to direct optical signals from each confinement to an array detector, e.g., a CCD, and concurrently separate signals from each different confinement into multiple constituent signal elements, e.g., different wavelength spectra, that correspond to different reaction events occurring within each confinement. In some embodiments, the setup further comprises means to control illumination of each confinement, and such means may be a feature of the optical system or may be found elsewhere is the system, e.g., as a mask positioned over an array of confinements. Detailed descriptions of such optical systems are provided, e.g., in U.S. Patent Pub. No. 20060063264, filed Sep. 16, 2005, which is incorporated herein by reference in its entirety for all purposes.

The systems or apparatus of the invention also typically include information processors or computers operably coupled to the detection portions of the systems, in order to store the signal data obtained from the detector(s) on a computer readable medium, e.g., hard disk, CD, DVD or other optical medium, flash memory device, or the like. For purposes of this aspect of the invention, such operable connection provides for the electronic transfer of data from the detection system to the processor for subsequent analysis and conversion. Operable connections may be accomplished through any of a variety of well known computer networking or connecting methods, e.g., Firewire®, USB connections, wireless connections, WAN or LAN connections, or other connections that preferably include high data transfer rates. The computers also typically include software that analyzes the raw signal data, identifies signal pulses that are likely associated with incorporation events, and identifies bases incorporated during the sequencing reaction, in order to convert or transform the raw signal data into user interpretable sequence data (see, e.g., Published U.S. Patent Application No. 2009-0024331, the full disclosure of which is incorporated herein by reference in its entirety for all purposes).

Exemplary systems are described in detail in, e.g., U.S. patent application Ser. No. 11/901,273, filed Sep. 14, 2007 and U.S. patent application Ser. No. 12/134,186, filed Jun. 5, 2008, the full disclosures of which are incorporated herein by reference in their entirety for all purposes.

Further, the invention provides data processing systems for transforming sequence read data into consensus sequence data. The data processing systems can include software and algorithm implementations to transform redundant sequence read data into consensus sequence data.

Various methods and algorithms for data transformation employ data analysis techniques that are familiar in a number of technical fields, and are generally referred to herein as statistical analysis. For clarity of description, details of known techniques are not provided herein. These techniques are discussed in a number of available reference works, such as those provided in U.S. Patent Publication No. 20090024331 and U.S. Ser. No. 61/116,439, filed Nov. 20, 2008, the disclosures of which are incorporated herein by reference in their entireties for all purposes.

The software and algorithm implementations provided herein are preferably machine-implemented methods, e.g., carried out on a machine comprising computer-readable medium configured to carry out various aspects of the methods herein. For example, the computer-readable medium preferably comprises at least one or more of the following: a) a user interface; b) memory for storing redundant sequence read data; c) memory storing software-implemented instructions for carrying out the algorithms for transforming redundant sequence read data into consensus sequence data; d) a processor for executing the instructions; e) software for recording the results of the transformation into memory; and f) memory for recordation and storage of the resulting consensus sequence read data. In preferred embodiments, the user interface is used by the practitioner to manage various aspects of the machine, e.g., to direct the machine to carry out the various steps in the transformation of redundant sequence read data into consensus sequence data, recordation of the results of the transformation, and management of the consensus sequence data stored in memory.

As such, the methods further comprise a transformation of the computer-readable medium by recordation of the redundant sequence read data and/or the consensus sequence data generated by the methods. Further, the computer-readable medium may comprise software for providing a graphical representation of the redundant sequence read data and/or the consensus sequence read data, and the graphical representation may be provided, e.g., in soft-copy (e.g., on an electronic display) and/or hard-copy (e.g., on a print-out) form.

The invention also provides a computer program product comprising a computer-readable medium having a computer-readable program code embodied therein, the computer readable program code adapted to implement one or more of the methods described herein, and optionally also providing storage for the results of the methods of the invention. In certain preferred embodiments, the computer program product comprises the computer-readable medium described above.

In another aspect, the invention provides data processing systems for transforming sequence read data from one or more sequencing reactions into consensus sequence data representative of an actual sequence of one or more template nucleic acids analyzed in the one or more sequencing reactions. Such data processing systems typically comprise a computer processor for processing the sequence read data according to the steps and methods described herein, and computer usable medium for storage of the initial sequence read data and/or the results of one or more steps of the transformation (e.g., the consensus sequence data), such as the computer-readable medium described above.

Figure 8:
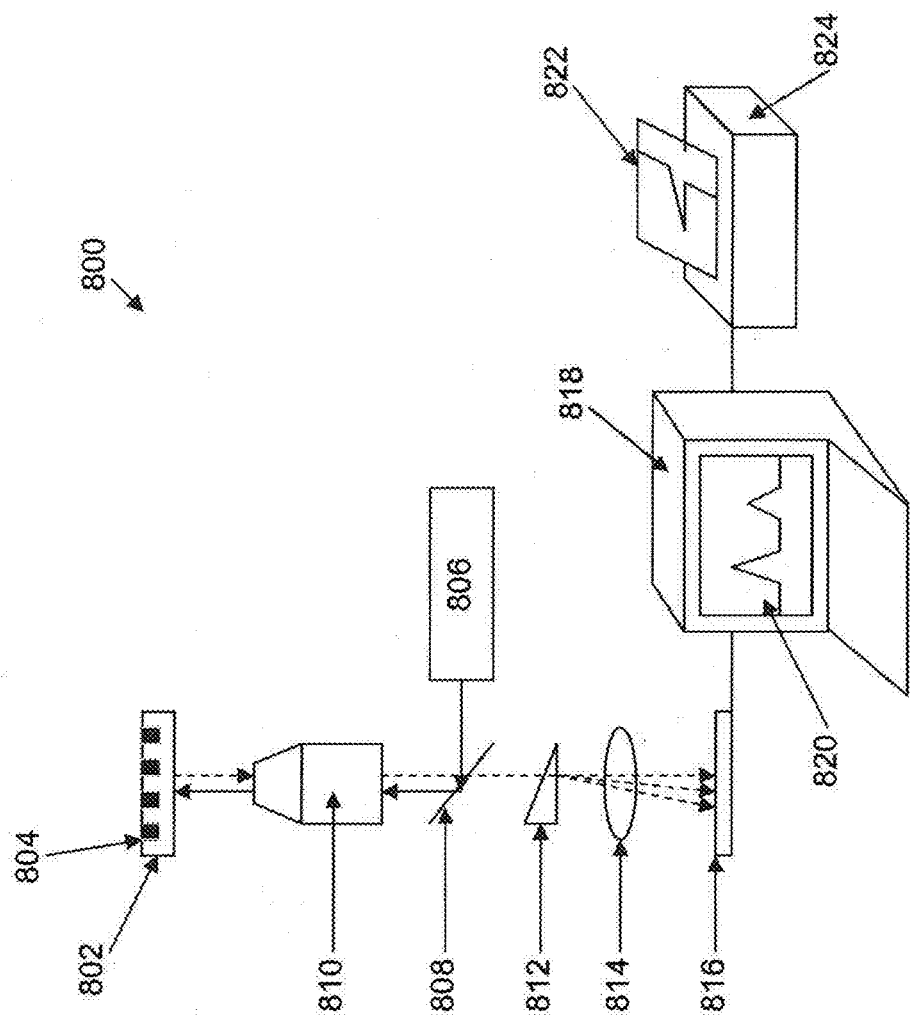
FIG. 8 shows an apparatus or system of the invention.

As shown in FIG. 8, the system 800 includes a substrate 802 that includes a plurality of discrete sources of chromophore emission signals, e.g., an array of zero mode waveguides of the invention having layers of non-reflective material disposed on their walls 804. An excitation illumination source, e.g., laser 806, is provided in the system and is positioned to direct excitation radiation at the various signal sources. This is typically done by directing excitation radiation at or through appropriate optical components, e.g., dichroic 808 and objective lens 810, that direct the excitation radiation at the substrate 802, and particularly the ZMW structures of the invention 804. Emitted signals from the ZMW structures 804 are then collected by the optical components, e.g., objective 810, and passed through additional optical elements, e.g., dichroic 808, prism 812 and lens 814, until they are directed to and impinge upon an optical detection system, e.g., detector array 816. The signals are then detected by detector array 816, and the data from that detection is transmitted to an appropriate data processing system, e.g., computer 818, where the data is subjected to interpretation, analysis, and ultimately presented in a user ready format, e.g., on display 820, or printout 822, from printer 824. As will be appreciated, a variety of modifications may be made to such systems, including, for example, the use of multiplexing components to direct multiple discrete beams at different locations on the substrate, the use of spatial filter components, such as confocal masks, to filter out-of focus components, beam shaping elements to modify the spot configuration incident upon the substrates, and the like (See, e.g., Published U.S. Patent Application Nos. 2007/0036511 and 2007/095119, and U.S. patent application Ser. No. 11/901,273, all of which are incorporated herein by reference in their entireties for all purposes).

One aspect of the invention is an apparatus for obtaining nucleic acid sequence information comprising a zero-mode waveguide array structure comprising: a transparent substrate having a top surface, and a reflective layer disposed upon the top surface of the transparent substrate; an array of apertures extending through the reflective layer to the transparent substrate wherein the apertures comprise wells having walls and bases, the bases of the wells comprising portions of the top surface of the transparent layer; and a non-reflective layer disposed on the walls of the wells wherein the thickness of the non-reflective layer is greater than about 5 nm. The zero-mode waveguide structure is incorporated into a device configured to hold an analysis solution in contact with the zero-mode waveguide structure, whereby the wells comprise the analysis solution which comprises reagents for carrying out reactions for which nucleic acid sequence information can be derived; including polymerase enzyme, nucleotides, and nucleic acid template, the solution further comprising fluorescent species. The apparatus further comprises an illumination system that illuminates the wells through the transparent layer; a detection system that detects emitted light over time from the fluorescent species within the wells, wherein the emitted light passes through the transparent layer; and a computing system that analyzes the emitted light over time in order to obtain sequence information.

Methods of Making ZMWs Having Non-Reflective Layers

The ZMW structures of the invention can be made using a number of approaches. In some cases, the process can involve first producing a structure having a lower transparent layer and an upper a cladding layer with holes or apertures extending through the cladding to the transparent layer; and subsequently depositing a layer of non-reflective material onto the walls. In some cases, the deposition of the non-reflective material can be carried out specifically, such that deposition only occurs on the cladding layer and not on the transparent substrate. In other cases, a conformal coating can be applied to the whole surface non-selectively. In some cases the non-selectively coated substrate can have the portions of the non-reflective material over the transparent substrate selectively removed. It can be advantageous to have some or all of the transparent substrate substantially free of non-reflective material, which can allow, for example, for the selective reaction of a functionalizing agent or coupling agent to the surface of the transparent substrate. Such a selectively functionalized transparent substrate can be used to selectively bind a molecule of interest, such as a polymerase enzyme selectively to the base of the ZMW structure. Such selective functionalization is described, for example in U.S. patent application Ser. No. 11/731,748, filed Mar. 29, 2007.

We have found that one useful method of forming the non-reflective layer comprises forming an oxide layer by controlled oxidation of material that constitutes the cladding layer. The oxide layer can be formed, for example by thermal oxidation of the cladding layer in the presence of oxygen and heat, or by electrochemical oxidation whereby the cladding layer comprises an electrode. For example, where the cladding layer comprises aluminum, a layer of alumina can be formed on the surface of the aluminum by subjecting it to oxidizing conditions, either thermally or electrochemistry. In some cases, an oxygen plasma is used to produce the oxide layer. Forming an oxide layer on the cladding has the benefit that the non-reflective layer is formed selectively on the cladding, and is not formed on the transparent substrate.

One aspect of the invention is a method for forming a zero-mode waveguide structure comprising: providing a substrate having a lower transparent layer and an upper metal layer, wherein the metal layer comprises an array of apertures disposed through the reflective layer to the transparent layer, the apertures having side walls, and exposing the substrate to oxidizing conditions whereby an oxide layer is formed on the side walls of the apertures under conditions whereby an oxide having a thickness of greater than 5 nm is produced.

Figure 9:
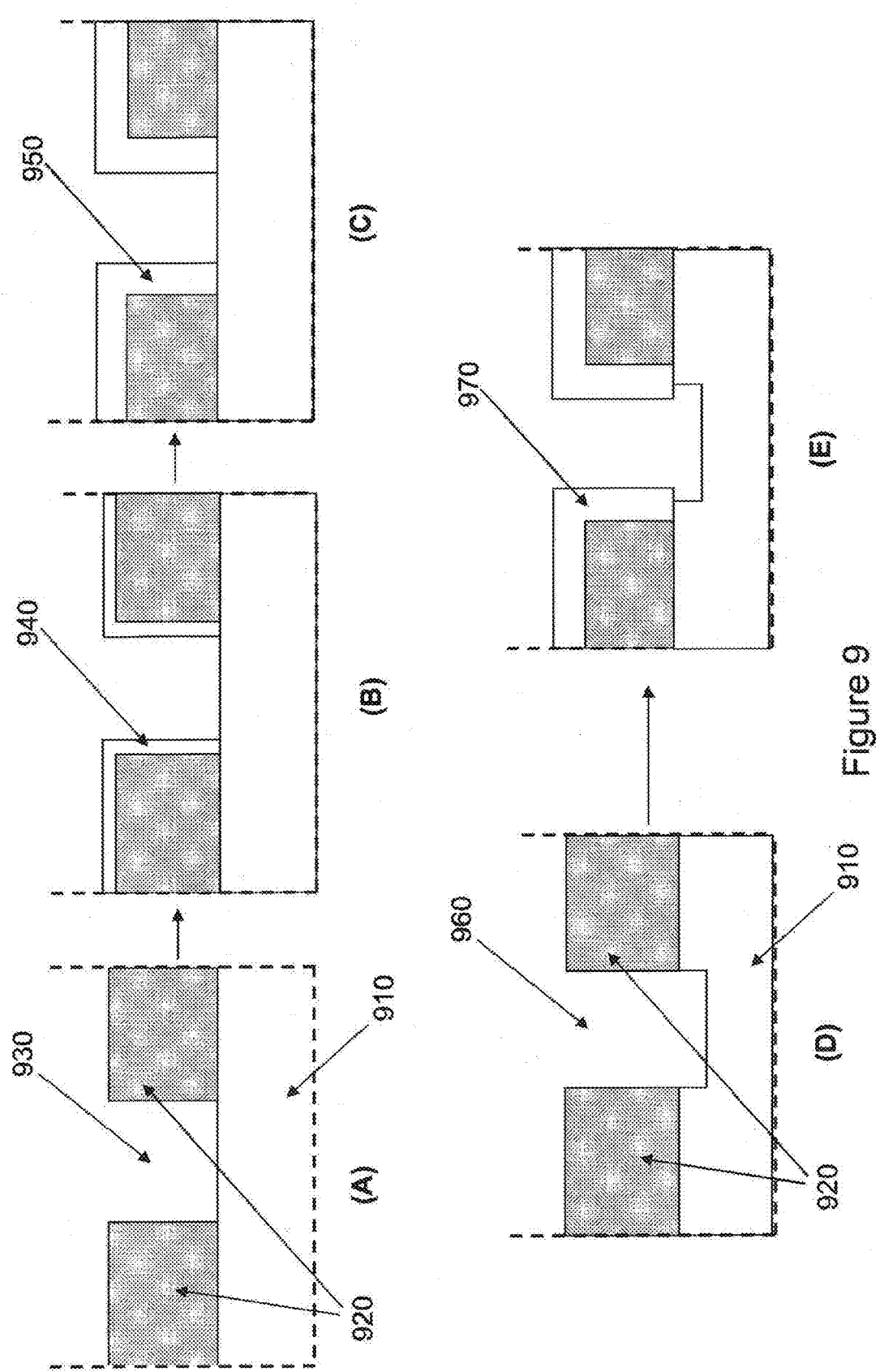
FIG. 9 (A)-(C) illustrates the production of an oxide layer on a ZMW structure.

FIG. 9 illustrates processes for producing an oxide layer on the surface of the cladding layer to form the non-reflective layer of the invention. FIG. 9(A) shows the structure prior to oxidation to form the non-reflective layer. The structure of FIG. 9(A), for example, a chip, has a transparent substrate 910 which has on its top surface an opaque cladding layer 920 which can be for example, a metal such as aluminum. The cladding layer has an array of apertures 930 extending through the cladding layer to the transparent substrate. The chip may have tens of thousand to millions of apertures. This process may also be carried out on a wafer comprising many chips, which can later be separated by dicing of the wafer. In some cases, the cladding layer will have a thin 3 to 4 nm native oxide on its surface. It is well known that metals such as aluminum will form a native oxide layer when exposed to air. This native oxide may or may not be removed prior to forming the non-reflective layer by oxidation.

The structure shown in 9(A) is exposed to oxidation conditions such as thermal (heat and oxygen), electrochemical, or oxygen plasma to form the structure illustrated in FIG. 9(B) having non-reflective layer 940 selectively on the cladding, and having substantially no non-reflective layer on the transparent substrate, except where it extends in from the cladding walls. Further oxidation results in a thicker non-reflective layer 950. As the oxidation proceeds, metal molecules on the surface of the cladding will generally become oxidized. Thus as the oxide layer grows, the ZMW aperture will generally become wider, and in addition, the metal portion of the cladding layer will become thinner due to the formation of oxide on the top surface of the cladding. At the same time, the cross sectional dimensions of the region inside the oxide layer (the solution volume) will generally become smaller because each molecule of oxide formed takes up more volume than that of the metal atom from which the oxide derives (e.g. $Al_2O_3$ has a higher molecular volume than $Al_2$). These dimensional changes can be taken into account in order to end up with a ZMW having both the desired ZMW dimensions and the desired solution volume dimensions.

FIGS. 9(D) and 9(E) show the production of a non-reflective layer onto a structure in which the aperture 960 extends into the transparent substrate 910. Oxidation results in the formation of the non-reflective layer 970 which in some cases will grow to extend over the region of the aperture 960 that extends into the transparent layer.

Thermal oxidation is generally carried out in the presence of an oxidizing agent and water. Suitable thermal oxidation agents comprise chromates, cerates, permanganates, titanium or zirconium oxides, lithium salts, and molybdates. The temperature of the thermal oxidation is generally below 300° C.

Plasma oxidation is generally carried out by exposing oxygen and or ozone at pressures from about 0.1 torr to about 100 torr, or between about 1 torr and about 10 torr. The temperature can be from room temperature to about 400° C.

An alternative method for forming the non-reflective layer of the invention is to deposit a layer onto a ZMW substrate. In some cases, the coatings are deposited conformally in a manner that conforms to the topography of the substrate. Coatings can, for example, be deposited in the gas phase or in solution. Solution coating or deposition methods can include dipping, spraying, brushing, spin coating, meniscus coating, roller coating, curtain coating, extrusion coating, plasma deposited and electrodeposition. In some cases, the coating will cover all surfaces including the transparent substrate at the bases of the ZMW apertures. In some cases, sol-gel chemistry can be used to produce, for example, silicon dioxide based non-reflective coatings. Chemical vapor deposition (CVD), for example with parylene, or plasma enhanced CVD (PECVD) oxide can be used to form the non-reflective layer. In some cases, a selective Atomic Layer Deposition (ALD) process can be used to selectively form a non-reflective coating on the cladding walls. In other cases, an ALD process can be used to non-specifically coat the structure to form the non-reflective layer, and the portion of the ALD layer over the transparent layer can be subsequently removed where desired, for example using etch-back. In some cases, Spin-on-Glasses (SOGs) can be spin coated onto the substrate to form the non-reflective layer, and the portion of the SOG over the transparent substrate can be subsequently removed. These coating methods can deposit, for example, silicon dioxide, silicon nitride, diamond, CVD oxide, CVD nitride, polymers such as polyimides or teflon, and spin-on-glasses. In some embodiments, two or more layers can be deposited as described above. For example, the non-reflective layer can comprise a bi-oxide layer stack of $Al_2O_3$ and $SiO_2$, which can provide control of the etch-back process. Other coating methods, such as electrodeposition allow for selectively coating the non-reflective layer on the cladding material. Materials and methods suitable for deposition are described, for example in Franssila, "Introduction to Microfabrication", Wiley, 2004, incorporated herein by reference for all purposes.

In some cases, electroplating or electrodeposition can be used to deposit a non-reflective layer. Generally, the part to be plated is the cathode of the circuit. Anode and cathode are immersed in an electrolyte containing one or more dissolved salts as well as other ions to assist the flow of electricity. A rectifier or battery supplies a direct current. At the cathode, the dissolved ions in the electrolyte solution are reduced at the interface between the solution and the cathode, such that they "plate out" onto the cathode. In some cases, electroless deposition can be employed.

Figure 10:
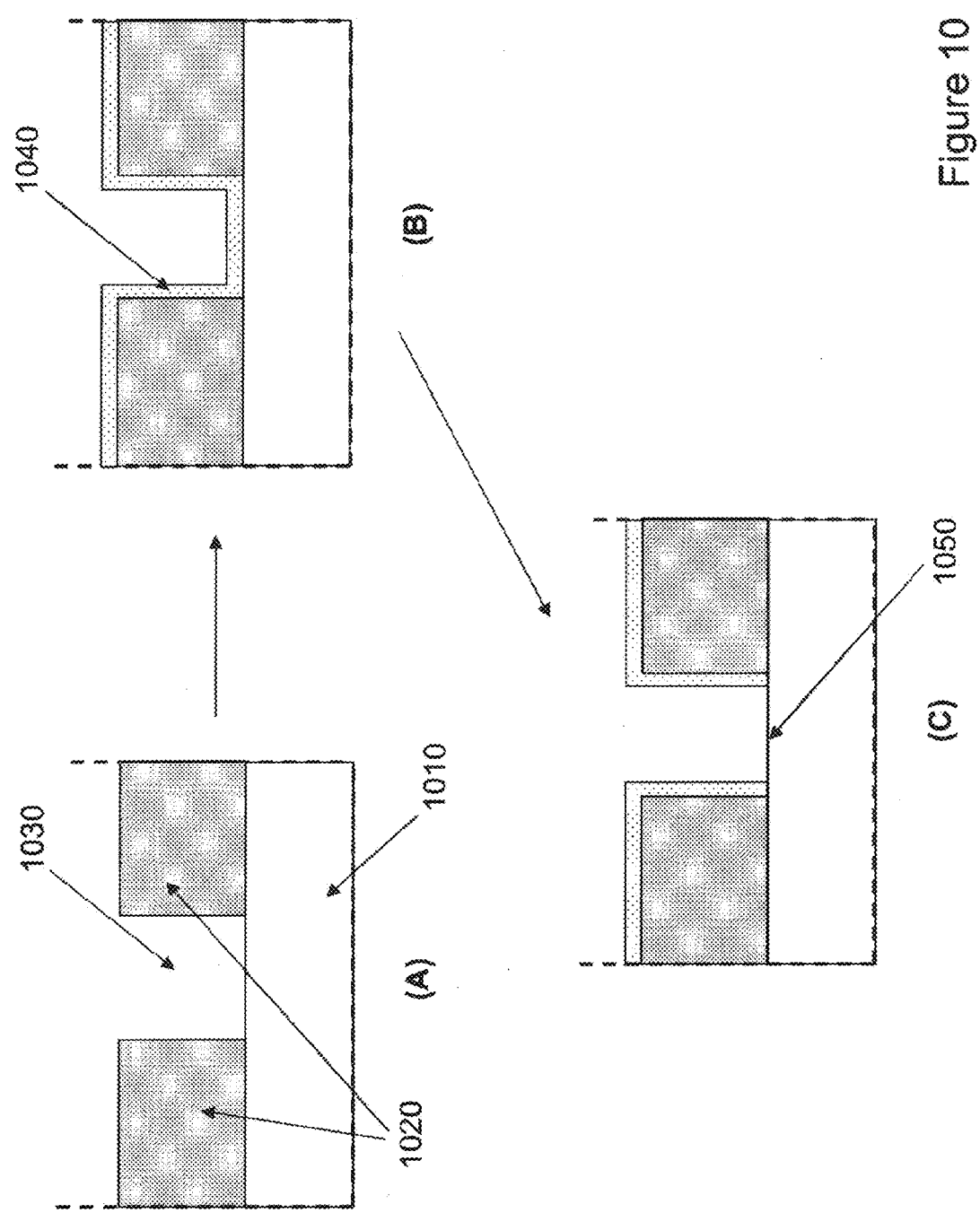
FIG. 10 illustrates a process for producing the non-reflective layer of the invention by depositing a conformal coating.

FIG. 10 illustrates a process of incorporating the non-reflective layer onto the walls of the ZMW by conformal coating. The structure in FIG. 10(A) has a transparent substrate 1010 upon which a cladding layer 1020 is disposed. The cladding layer 1020 has apertures 1030 extending through the cladding layer to the transparent substrate. The structure of FIG. 10(A) is coated with the non-reflective layer material in a conformal manner such that the ZMW walls, the bases of the ZMWs, and the top surface of the cladding layer is coated relatively uniformly. The use of such a conformal coating method has the advantage of being straightforward and manufacturable. However, the surface after this treatment is uniform, precluding certain approaches toward specifically functionalizing the base of the ZMW. In some cases, subsequent to conformal coating, the portion of the non-reflective layer over the transparent substrate at the ZMW base can be selectively removed, exposing the transparent substrate at the ZMW base 1050, and allowing specific functionalization of the surface, for example, using silanes.

Figure 11:
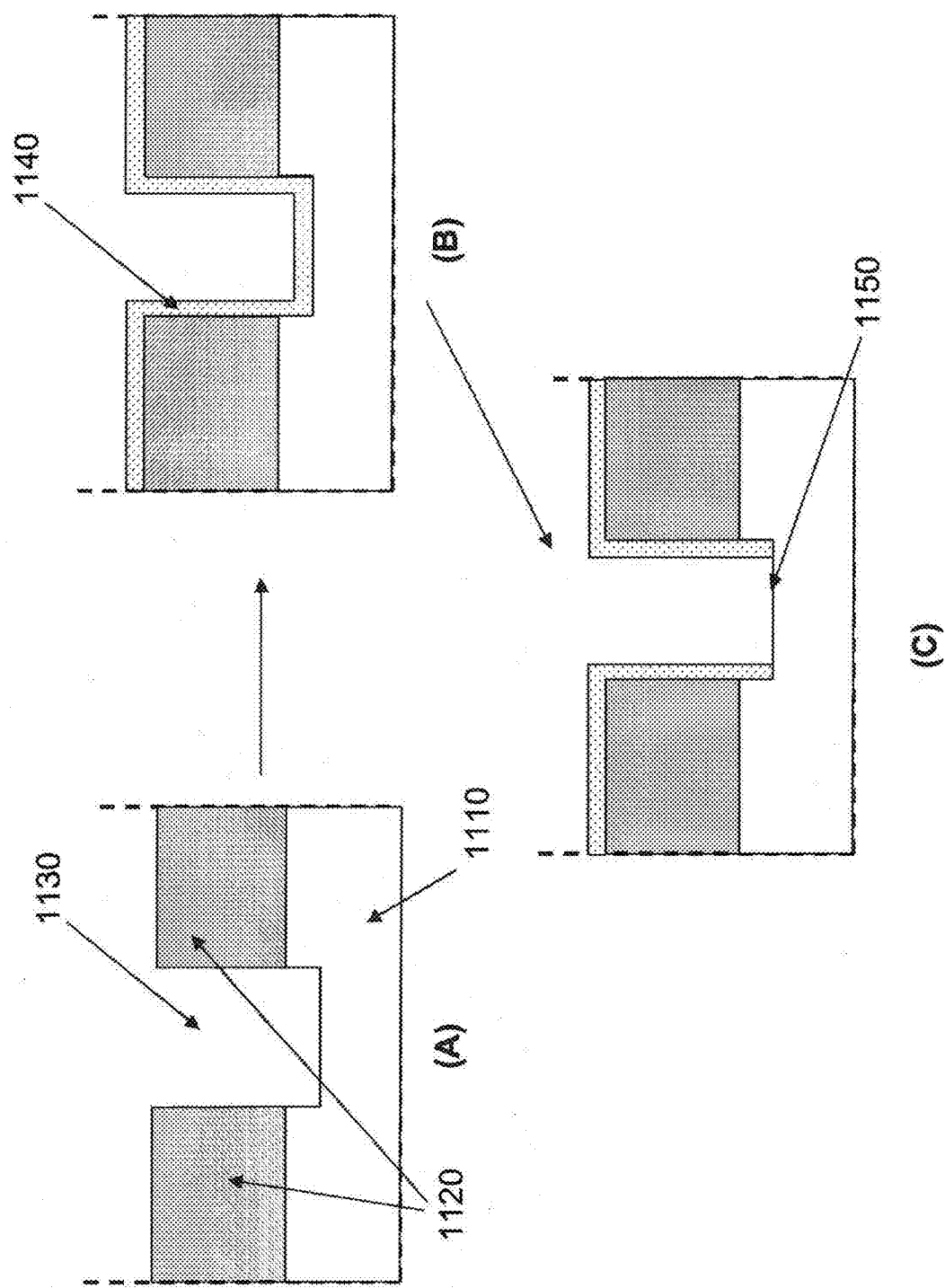
FIG. 11 illustrates a process for producing the non-reflective layer of the invention for a ZMW having an aperture that extends into the transparent substrate by depositing a conformal coating.

FIG. 11 illustrates a process for producing non-reflective layers on the ZMW walls where the ZMW aperture extends through the cladding layer and into the transparent substrate. As above, the structure in FIG. 11(A) has a transparent substrate 1110 upon which a cladding layer 1120 is disposed. The cladding layer 1120 has apertures 1130 extending through the cladding layer and extending into the transparent substrate. The structure of FIG. 11(A) is coated with the non-reflective layer material in a conformal manner such that the ZMW walls, the bases of the ZMWs, and the top surface of the cladding layer is coated relatively uniformly. Unlike the process shown in FIG. 10, here, since the aperture extends into the transparent substrate, the coating on the top of the transparent substrate does not necessarily raise the base up into the ZMW. In some cases, subsequent to conformal coating, the portion of the non-reflective layer over the transparent substrate at the ZMW base can be selectively removed, or etched back, exposing the transparent substrate at the ZMW base 1150, and allowing specific functionalization of the surface, for example, using silanes. The etch-back step can be performed, for example, by using photolithography to define the region for etch-back.

Figure 12:
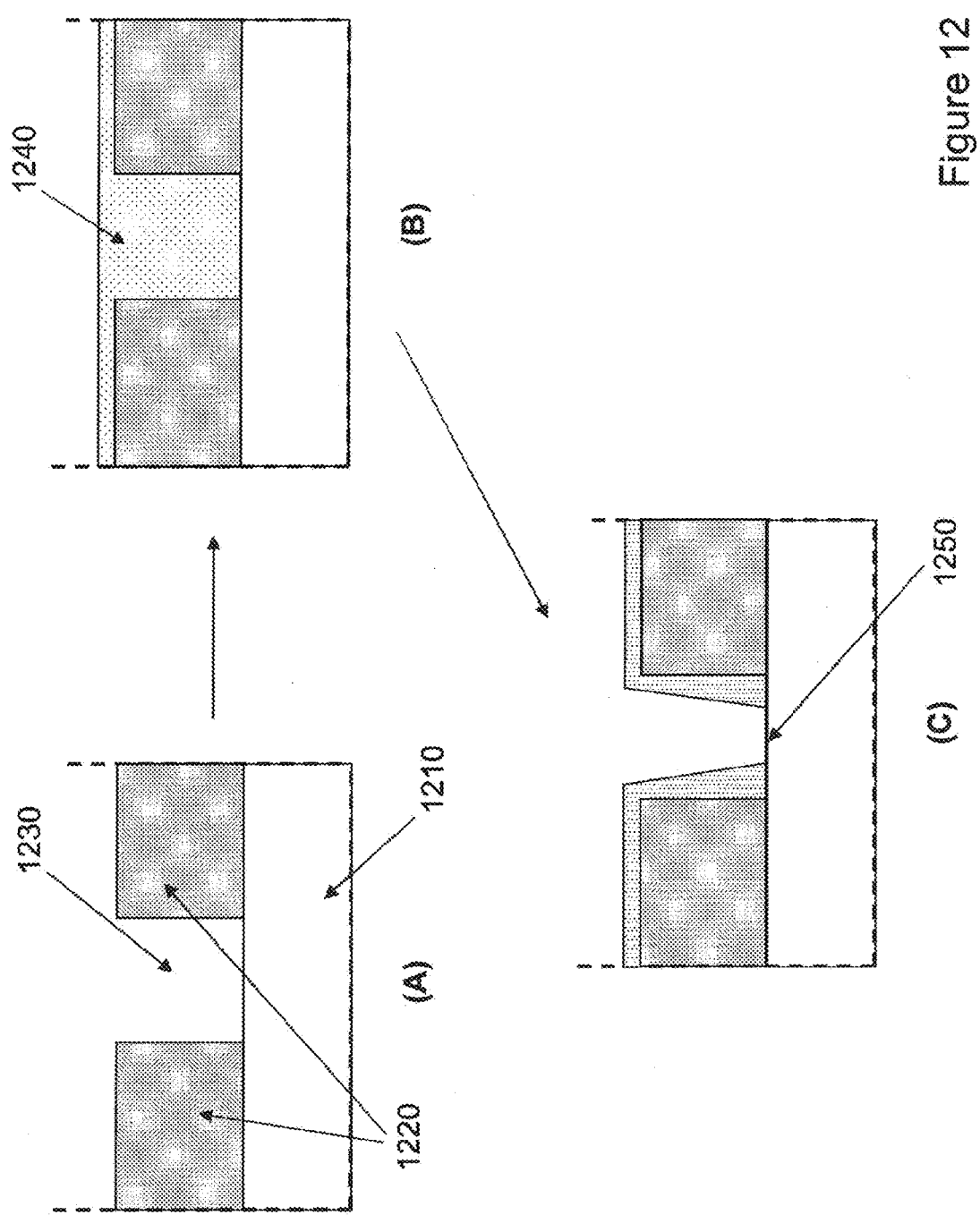
FIG. 12 illustrates a process for producing a non-reflective layer of the invention using a planar coating.

FIG. 12 illustrates a process similar to that of FIG. 11 but utilizing a planar rather than a conformal coating. A planar coating 1240 is applied to the ZMW array structure having apertures 1230 extending through cladding layer 1220 to transparent layer 1210. The portion of the non-reflective layer over the transparent substrate at the ZMW base can be selectively removed, or etched back, exposing the transparent substrate at the ZMW base 1250, and allowing specific functionalization of the surface, for example, using silanes. The etch-back step can be performed, for example, by using photolithography to define the region for etch-back. Methods for forming the non-reflective layer also include methods intermediate to that of FIG. 11 and FIG. 12, wherein a semi-conformal coating is applied, then subsequently selectively removed, or etched back to produce the solution volume. The etch-back step can be performed, for example, by using photolithography to define the region for etch back.

Another method of preparing the non-reflective layers of the invention comprises growing polymeric layers from the surface of the cladding material, for example by polymerization or by grafting. In one embodiment an initiation monomer is attached to the surface of the cladding, either selectively on the walls or on the walls and top surface. A source of monomer is then introduced, and polymerization from the walls is carried out. The thickness of the coating on the walls can be controlled, by controlling the length (molecular weight) of the polymer which is formed. Analogously, polymer can be grown from the surface by attaching to the surface a catalyst, or catalyst/monomer complex. Methods for controlling polymer molecular weight are well known in the art. Methods for synthesizing polymers and controlling molecular weight are described, for example, in Braun et al., "Polymer Synthesis: Theory and Practice", $4^{th}$ Edition, Springer, 2005. In other embodiments, reactive groups on the surface of the cladding layer react with fully formed polymers to graft the polymers to the surface of the cladding. The thickness of the non-reflective layer produced in this manner can be controlled by controlling the molecular weight of the polymers attached to the cladding and the density of attachment. Selective polymerization and or grafting onto the cladding can also be accomplished using electropolymerization.

Another method of preparing the non-reflective layers of the invention comprises depositing multilayers onto the surface, including depositing polyelectrolyte multilayers. The multilayers can be selectively deposited on the cladding layer without being deposited on the transparent substrate. For example, where the cladding layer is a metal such as aluminum, with a native aluminum oxide surface, and the transparent layer comprises a silica material such as fused silica. The difference in reactivity of these surfaces can be used to facilitate selective deposition onto the cladding. In some cases, the walls of the ZMWs can be treated in order to encourage multilayer deposition, and/or the top of the cladding can be treated to discourage multilayer deposition in order to allow for selective deposition on the walls of the ZMWs. The multilayers can be made to incorporate components that increase the refractive index in order to control the refractive index of the non-reflective layer. Such components can include metal or metal oxide components including chromium, and titanium, or substituents such as bromine. Polyelectrolyte multilayers can be conveniently formed, e.g. through successive deposition of alternating layers of polyelectrolytes of opposite charge. See, e.g., Decher (1997) Science 277:1232.

In one class of embodiments, a phosphate or phosphonate compound serves as the first layer on which a polyelectrolyte multilayer is built on the surface, e.g., by successive deposition of oppositely charged polyelectrolytes.

The polymers comprising the multilayer can include phosphorous containing polymers such polymers comprising polyphosphonates. An effective approach to such multilayers uses multivalent cations to assemble the polyphosphonates containing polymers. Particularly useful multivalent cations are those of transition metals, and in particular those of group IV transition metals, titanium (Ti), zirconium (Zr), or hafnium (Hf). A multilayer can be constructed with alternating layers. The multilayers can be produced by alternately treating the surface with a transition metal compound such as $HfCl_2$, $ZrOCl_2$, or $ZrCl_4$, and then with the phosphonate-containing polymer such as PVPA or Cp30.

In some cases, the transition metal compound and conditions can be chosen to have little or substantially no reactivity with $SiO_2$ such that the multilayer is selectively formed on the cladding layer.

The transition metal compounds can be introduced to the surface in solution, for example in water, methanol or a mixture of water and methanol. The number of layers can be 2, 3, 4, 5, 6, 7, 8, 9, 10 or more than 10 layers. In some embodiments 3 to 6 layers are used.

Electrochemical Oxidation—Anodization

We have found that one particularly useful method for producing the non-reflective layers on the walls of the ZMWs is by electrochemical oxidation (electrochemical anodization) of the cladding layer. Electrochemical anodization allows for the production of non-reflective layers on the ZMW in a controlled manner. The thickness of the non-reflective layer can be controlled, for example, by controlling the voltage, and or the current supplied during the electrochemical process. Where the conditions are controlled, a metal oxide non-reflective layer can be formed that is dense, robust, and smooth. We have found that the refractive index of the oxide layer that is formed is within a useful range for reducing illumination hot-spots, and for directing the illumination light into the solution volume of the ZMW.

One aspect of the invention is a method for forming a zero-mode waveguide array structure comprising: providing an electrochemical system comprising a working electrode, a counter electrode, and optionally a reference electrode; providing a substrate having a lower transparent layer and an upper electrically conductive reflective layer, wherein the electrically conductive reflective layer comprises an array of apertures disposed through the reflective layer to the transparent layer, the apertures having side walls, wherein the electrically conductive reflective layer comprises the working electrode; and applying a voltage to the working electrode such that a layer of non-reflective material is formed onto the side walls of the aperture.

The controlled electrochemical oxidation of the oxide layer can also provide ZMW arrays having improved stability and longer life than ZMWs not treated electrochemically. Arrays of optical confinements are sometimes used in environments which may cause the corrosion of metal or metal oxide portions of the optical confinement structures. We have found that even where measuring enzymes in optical confinement arrays under conditions similar to biological conditions, corrosion of the metal or metal oxide portions of the arrays can negatively affect performance. This may not be completely expected since the metals used, such as aluminum, are relatively robust, the biological conditions are often at or near neutral pH, and the temperatures are relatively low compared to other industrial processes where metals such as aluminum are routinely utilized. We have found, however, that corrosion of the optical confinement array can negatively affect array performance even when the metal surfaces that have been passivated without electrochemical treatment. One reason why corrosion may become an issue with optical confinement arrays where it is not an issue for similar types of metal substrates is that changes in dimensions on the order of nanometers to tens of nanometers can affect the performance of the optical confinements. Such small dimensional changes may not be detected in other uses. Another reason why the arrays of optical confinements may experience corrosion in these relatively mild environments is that the aqueous environments can, in some cases, have relatively high salt concentrations. In addition to improving the corrosion resistance of the ZMW array, the electrochemical treatment of the invention can also provide for improved biochemical compatibility. Improved biochemical compatibility can include, for example, decreased deposition biological molecules such as proteins, nucleotides, and nucleic acids onto the passivated surfaces.

The electrochemical oxidation process of the invention is most useful for cladding layers which form stable oxide layers. One preferred material for the cladding layer is aluminum. Other suitable materials which can form stable oxide layers include titanium, zinc, magnesium, and niobium. Alloys comprising these metals can also be used.

The oxidized layer is grown by passing a direct current through an electrolytic solution, with the metal cladding, e.g. aluminum serving as the anode (the positive electrode). The passage of current generally releases hydrogen at the cathode (the negative electrode) and oxygen at the surface of the metal, e.g. aluminum anode, creating a layer of aluminum oxide. Alternating current and pulsed current may also be used. The voltage may range from 1 to 300 V DC, from 5 to 100 V or from 10 to 30 V. Conventional anodization processes are often carried out to encourage ongoing pitting of the growing oxide layer to avoid having the process terminated by auto-passivation. For the layers of oxide produced for the ZMW's of the invention this type of re-pitting in order to grow thicker layers is generally not required because of the relatively low thickness of the coatings used (e.g. from 5 to 50 nm), and because of the desire for smooth and uniform coatings. Thus, in some cases, we have found it desirable to allow for auto-passivation, for example, to provide a fixed voltage between about 5 V and about 50 V or between about 10V and about 30 V and allow the process to proceed until auto-passivation significantly diminishes the current flow, thus defining the thickness.

Pitting can also be encouraged by using highly acidic conditions. We have found that while conditions from about pH 2 to about pH 10 can be used, that more robust oxide layers can generally be formed by carrying out the process between about pH 4 and about pH 9, and in some cases between pH 4 and pH 6.

The electrochemical process of the invention can be carried out in any suitable electrolyte. The preferred electrolyte is an electrolyte in which aluminum oxide is poorly soluble. Such electrolytes include electrolytes comprising, for example, borates, phosphates and tartrates. In some cases ammonium borate, phosphate, or tartrates are used. Anions having low mobility are generally preferred. In some cases, the presence of mobile anions, such as chloride, fluoride and iodine can lead to pitting, so the levels of such mobile anions is kept low, and in some cases the medium is substantially free of such ions. The electrolyte is chosen such that adequate control over thickness with voltage can be obtained. In some cases, the electrolytes allow the oxide growth to be linearly proportional to the applied potential. (J. Edwards Coating and Surface Treatment Systems for Metals. Finishing Publications Ltd. and ASM International. pp. 34-38 (1997)).

We have found that arrays of optical confinements having metal layers can be made more robust by providing an electrochemical treatment in the presence of phosphorous containing compounds. In particular, we have found that optical confinement arrays having a transparent layer and a metallic cladding layer have improved long term performance in solution after electrochemical passivation in the presence of phosphorous containing passivation compounds. The invention provides an anodization process that creates, for example, a phosphonate-rich passivating oxide film on the metal, e.g. aluminum cladding. Anodization in the presence of a phosphorous containing compound such as PVPA can result in the formation of a smooth oxidation layer as required for use with a zero mode waveguide application. In addition, these oxide coatings can be robust, with improved corrosion resistance. And, these coatings can also act as passivation layers with respect to biological contamination, assisting in the prevention of deposition of nucleic acids, nucleotides, proteins, and other biomolecules on the surface.

Electrochemical anodization of metals such as aluminum in the presence of phosphorous containing passivation compounds can be implemented using electrochemical systems known in the art. The electrochemical anodization can be carried out using a two electrode, or a three-electrode electrochemical cell having a counter electrode, an optional reference electrode, and using the cladding layer of the optical confinement array as the working electrode. The cell can be equipped with, for example, a graphite counter electrode and a saturated calomel reference electrode. The anodization can be achieved using either potentiostatic or cyclic deposition.

Suitable phosphorous containing electrochemical passivation compounds of the invention generally comprise P=O and/or P—OH functionality. In particular, compounds comprising phosphate or phosphonate groups can be used. Preferred passivation or coating compounds include phosphorous containing polymeric materials. Suitable phosphorous containing polymeric materials include homopolymers and copolymers of poly(vinylphosphonic acid).

The phosphorous compounds for use in electrochemical depositions of the invention can include the phosphorous containing selective passivation compounds described herein.

These compounds will generally comprise P=O and/or P—OH functionality. In particular, compounds comprising phosphate or phosphonate groups can be used. In some cases, these compounds will form strong bonds to a metal or metal oxide surface such as the surface of aluminum to provide robust passivation to the metal surface. Preferred passivation or coating compounds include phosphorous containing polymeric materials. Suitable phosphorous containing polymeric materials include homopolymers and copolymers of poly(vinylphosphonic acid), Albritect™ CP-30, Albritect™ CP-10, Albritect™ CP-90, Aquarite® ESL, and Aquarite® EC4020. Albritect™ and Aquarite® compounds are commercially available from Rhodia, Inc. Phosphate or phosphonic acid moieties can in some cases bind strongly to metal oxides (e.g., aluminum oxide, titanium oxide, zirconium oxide, tantalum oxide, niobium oxide, iron oxide, and tin oxide) during the electrochemical process, forming phosphorous containing oxides. Thus, compounds that comprise at least one phosphate group (—OP(O)(OH)$_2$, whether protonated, partially or completely deprotonated, and/or partially or completely neutralized) or phosphonic acid group (—P(O)(OH)$_2$, whether protonated, partially or completely deprotonated, and/or partially or completely neutralized) can be used.

The electrolyte can contain an alkyl phosphate or an alkyl phosphonate. The terms phosphonic acid and phosphonate are alternatively used to refer to the compounds described herein. It is understood that a phosphonic acid will generally have hydrogens associated with two of the phosphonic acid oxygens, and that a phosphonate will generally have other counterions associated with these oxygens. In aqueous solution, hydrogen ions and counterions can exchange rapidly. Thus generally either phosphonic acid and phosphonate compounds can be useful in the invention.

Exemplary alkyl phosphates and alkyl phosphonates include, but are not limited to, an alkyl phosphate or alkyl phosphonate in which the alkyl group is a straight chain unsubstituted alkyl group (e.g., a straight chain alkyl group having from 1 to 26 carbons, e.g., from 8 to 20 carbons, e.g., from 12 to 18 carbons). Additional exemplary alkyl phosphates and alkyl phosphonates include functionalized or substituted alkyl phosphonates and alkyl phosphates, for example, functionalized X-alkyl-phosphonates and X-alkyl-phosphates where X is a terminal group comprising or consisting of a vinyl (CH$_2$), methyl (CH$_3$), amine (NH$_2$), alcohol (CH$_2$OH), epoxide, acrylate, methacrylate, thiol, carboxylate, active ester (NHS-ester), melamine, halide, phosphonate, or phosphate group, or an ethylene glycol (EG) oligomer (EG4, EG6, EG8) or polyethylene glycol (PEG), photoinitiator (e.g., photo-inverters such as dithiocarbamates (DTC)), photocaged group, or photoreactive group (e.g., psoralen). The alkyl chain spacer in the X-alkyl-phosphonate or X-alkyl-phosphate molecule is a hydrophobic tether that optionally has 1 to 26 methylene (CH$_2$) repeat units, preferably from 8 to 20, and more preferably from 12 to 18. The alkyl chain may contain one or more (up to all) fluorinated groups and/or can instead be a hydrocarbon chain with one or more double or triple bonds along the chain. The X-alkyl-phosphate or X-alkyl-phosphonate layer can furthermore be used as a substrate to anchor other ligands or components of the surface stack, such as a polyelectrolyte multilayer or chemisorbed multilayer. The alkyl phosphates/phosphonates can form a stable, solvent resistant self-assembled monolayer that can protect the underlying material (e.g., aluminum) from corrosion etc.; the role of the alkyl tether in the above structures is to enhance the lateral stability of the chemisorbed monolayer in aqueous environments. In embodiments in which the phosphonate or phosphate compound includes an unsaturated hydrocarbon chain, the double or triple bond (s) can serve as lateral crosslinking moieties to stabilize a self-assembled monolayer comprising the compound. Specific exemplary alkyl phosphates and alkyl phosphonates include, but are not limited to, octyl phosphonic acid, decyl phosphonic acid, dodecyl phosphonic acid, hexadecyl phosphonic acid, octadecyl phosphonic acid, docosyl phosphonic acid (i.e., C22 phosphonic acid), hydroxy-dodecyl phosphonic acid (HO(CH$_2$)$_{12}$P(O)(OH)$_2$), hydroxy-undecenyl-phosphonic acid, decanediylbis(phosphonic acid), dodecylphosphate, and hydroxy-dodecylphosphate.

Suitable phosphonates include high molecular weight polymeric phosphonates such as polyvinylphosphonic acid (PVPA):

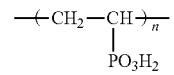

wherein n can be from about 1 to about 1000 or from about 10 to about 100.

Phosphonate end-capped polymers of polymers having acidic functional groups such as carboxylic acids, sulfonic acids and mixtures thereof can also be used. These can include phosphonate end-capped poly(acrylates), poly(sulfonates), and copolymers thereof. Exemplary phosphonate end-capped compounds include:

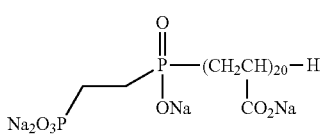

where n can be from about 1 to 1000, can be between about 10 and about 100, and can be about 20 (available from Rhodia, Inc. as Aquarite® EC4020), or

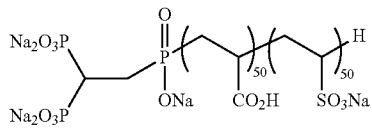

where n and m can be from about 1 to about 1000, from about 10 to about 100, or can each be about 50, in some cases, m is about 24 and n is about 16 (available from Rhodia, Inc. as Aquarite® ESL). Exemplary copolymers copolymer include the copolymers:

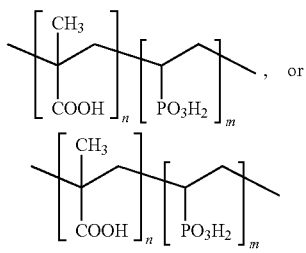

such as vinyl phosphonic acid-acrylic acid copolymers (commercially available from Rhodia as Albritect™ CP30). The values for n and m can range from about 1 to about 1000. In some cases, m is between about 10 and about 100, and n is between about 100 and 300. In some cases, m is between about 50 and about 70, and n is between about 80 and 120. In some cases, m is about 60 and n is about 200.

Suitable phosphonates also include low molecular weight phosphonates such as 2-carboxyethyl phosphonic acid (also known as 3-phosphonopropionic acid; commercially available from Rhodia as Albritect™ PM2). Other suitable low molecular weight phosphorous containing compounds are described in U.S. patent application Ser. No. 11/394,352.

One aspect of the invention is a method for producing a zero-mode-waveguide array comprising: providing an electrochemical cell having a working electrode, a counter electrode, and optionally a reference electrode, wherein the working electrode comprises a metallic upper layer of a substrate also having a transparent lower layer, wherein the metallic upper layer comprises an array of apertures extending through metallic upper layer to the transparent lower layer; contacting the working electrode with a solution comprising a phosphorous containing compound; and passing current through the electrochemical cell whereby a phosphorous containing material is deposited onto the metallic upper layer of the substrate.

The electrochemical anodization is generally carried out in aqueous solution. The phosphorous containing passivation compounds, e.g. phosphonate containing polymers, are generally provided in concentrations from about 0.01% to about 20% (weight by volume (e.g. g/cc)). The temperature can be around room temperature. In some cases, temperatures from 20° C. to about 90° C. are used. While carrying out the anodization, the current can be monitored in order to control the extent of the anodization/passivation reaction.

Electrochemical anodization methods of the invention can result in optical confinement arrays having that exhibit less corrosion than optical confinement arrays that have not been electrochemically passivated. The electrochemically passivated arrays can have more than 30%, 40%, 50%, 70% 80% or 90% lower rates of corrosion than arrays which have not been electrochemically passivated with the methods of the invention. In some cases, the electrochemically passivated arrays can have more than 2 times, 3 times, 4 times, 6 times, or 10 times lower rates of corrosion than arrays which have not been electrochemically passivated with the methods of the invention.

Methods of Use

The ZMWs of the invention can be utilized for the optical measurement of analytes at very small amounts, down to the level of single molecules. By controlling the solution volume within a ZMW structure, higher quality measurements can be made of single molecule systems.

As described herein, the systems of the invention can be used for analyzing molecules in very small volumes. The individual confinement in the array can provide an effective observation volume less than about 1000 zeptoliters, less than about 900, less than about 200, less than about 80, less than about 10 zeptoliters. The systems of the invention can provide for measurements at or near physiological conditions, for example, in the range from micro-molar to millimolar.

One aspect of the invention is a method for analyzing a luminescent species comprising: disposing a luminescent species in an aperture that extends through an upper reflective layer that is disposed on a lower transparent layer, wherein the aperture comprises side walls, and a non-reflective layer on the side walls of the aperture having a thickness of greater than 5 nm; and detecting emitted light from the luminescent species wherein the emitted light passes through the transparent layer.

The systems can be used to measure optical properties of molecules using luminescent indicators. Luminescent tags such as dyes and fluorescent nanoparticles can be incorporated into or near the analytical molecules of interest. Fluorescent methods are particularly useful, including using dye-dye interactions such as Forster Resonance Energy Transfer (FRET) in order to measure molecular events for a single molecule. Observations in real-time can be made of (1) distributions and fluctuations in enzymatic activity, (2) reaction mechanisms, and (3) transient intermediates that are otherwise difficult to capture in conventional experiments due to their low steady state concentrations.

In certain aspects, the subject invention provides substrates and methods for performing single-molecule observation. The optical arrays of the invention can provide information on individual molecules whose properties are hidden in the statistical mean that is recorded by ordinary ensemble measurement techniques. In addition, because of multiplexing, the arrays are conducive to high-throughput implementation, requiring small amounts of reagent(s), and taking advantage of the high bandwidth of modern avalanche photodiodes for extremely rapid data collection. Moreover, because single-molecule counting automatically generates a degree of immunity to illumination and light collection fluctuations, single-molecule analysis can provide greater accuracy in measuring quantities of material than bulk fluorescence or light-scattering techniques. As such, the subject substrates and devices may be used in a wide variety of circumstances including sequencing individual human genomes as part of preventive medicine, rapid hypothesis testing for genotype-phenotype associations, in vitro and in situ gene-expression profiling at all stages in the development of a multi-cellular organism, determining comprehensive mutation sets for individual clones and profiling in various diseases or disease stages. Other applications involve profiling of cell receptor diversity, identifying known and new pathogens, exploring diversity towards agricultural, environmental and therapeutic goals.

In preferred embodiments, the instant invention is directed to observing nucleic acid sequencing reactions, e.g., sequencing-by-incorporation reactions. In preferred embodiments, such an illuminated reaction analyzes a single molecule to generate nucleotide sequence data pertaining to that single molecule. For example, a single nucleic acid template may be subjected to a sequencing-by-incorporation reaction to generate one or more sequence reads corresponding to the nucleotide sequence of the nucleic acid template. For a detailed discussion of such single molecule sequencing, see, e.g., U.S. Pat. Nos. 6,056,661, 6,917,726, 7,033,764, 7,052,847, 7,056,676, 7,170,050, 7,361,466, 7,416,844; Published U.S. Patent Application Nos. 2007-0134128 and 2003/0044781; and M. J. Levene, J. Korlach, S. W. Turner, M. Foquet, H. G. Craighead, W. W. Webb, SCIENCE 299:682-686, January 2003 Zero-Mode Waveguides for Single-Molecule Analysis at High Concentrations, all of which are incorporated herein by reference in their entireties for all purposes.

Methods for Obtaining High Loading of Single Molecules in ZMWs—Islands of Functionalizing Agent As described above, arrays ZMWs are useful for optically analyzing reactions of many single molecules simultaneously. When performing such analyses, it is generally desirable to maximize the number of ZMWs in the array that are occupied with a single molecule of interest, and to minimize the number of ZMWs in the array that have zero or have more than one single molecule of interest (e.g., template or other analyte and/or enzyme). Loading two or more molecules of interest into a ZMW or other small observation volume tends to complicate any analysis of signals observed from double (or more than double)-loaded region. This is because two (or more) sets of signals may simultaneously be observed from the ZMW or other observation volume, meaning that the signals from the ZMW would have to be deconvoluted before data from the observation region could be used. More typically, data from double (+) loaded ZMWs can be recognized by various data analysis methods, and data from mis-loaded ZMWs or other relevant observation volumes is simply discarded.

To reduce the incidence of multiple molecule loading events in the relevant reaction/observation volume(s) of the array, it is typical in the art to substantially "under-load" the array with the analyte molecules of interest. See, for example "Improved fabrication of zero-mode waveguides for single-molecule detection" (2008) Foquet et al. *Journal of Applied Physics* 103, 034301. Random distribution of molecules into the array results in one or fewer molecules being loaded into most reaction/observation volumes when fewer than 37% of all observation volumes are loaded. This type of loading is referred to as "Poisson-limited" analyte loading, meaning that few enough molecules are added to the array so that a Poisson-style random statistical distribution of the analytes into the array results in one or fewer analytes per observation volume in most cases. Some approaches to achieving single molecule loading above the Poisson distribution are described in U.S. patent application Ser. No. 12/384,097 filed Mar. 30, 2009.

One aspect of the invention is a method of obtaining an island of functionality within a nanoscale aperture in a cladding layer on the surface of a substrate. The method comprises growing a constriction layer selectively on the cladding layer in order to constrict the nanoscale aperture such that a portion of the substrate within the aperture is still exposed, and functionalizing the exposed portion of the substrate to provide reactive species on these exposed portions. Some or all of the constriction layer is removed, thereby producing an island of functionalized surface within the nanoscale aperture at its base. The island of functionality can be used to couple a molecule of interest, such as a single molecule to the base of the aperture. The coupling of the single molecule can be performed before the removal of the constriction layer or after the removal of the constriction layer. The island of functionality can be used to attach a single particle or bead within each aperture. The single particle or bead can be inorganic or organic, it can comprise a polymer, and can comprise a metal or metal oxide. The particle can be, for example, a quantum dot.

Figure 13:
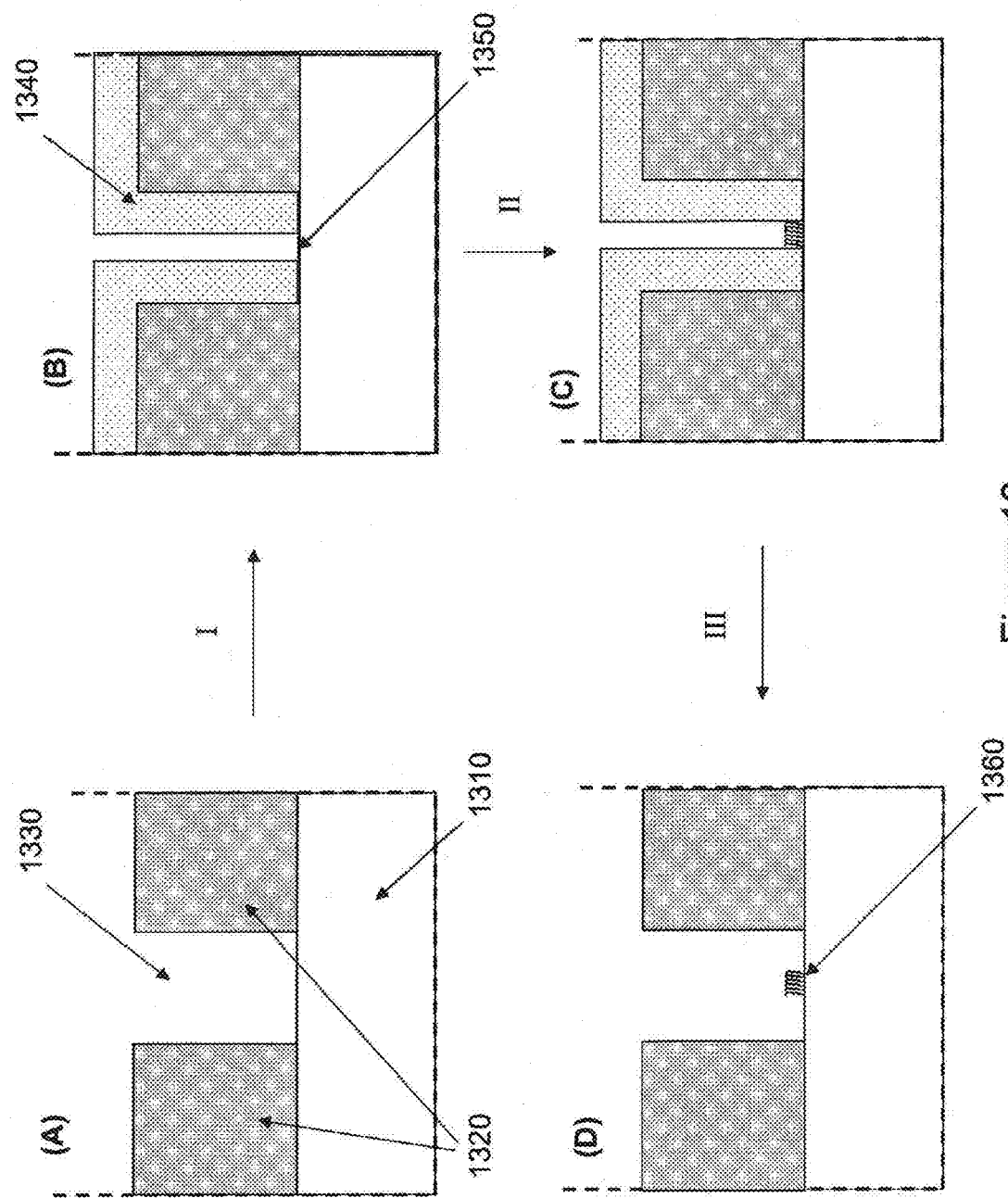
FIG. 13 illustrates an embodiment of a method of the invention for producing an island of functionality within the ZMW by growing an aperture constriction layer.

An exemplary process of the invention for forming the island of functionality is shown in FIG. 13. A substrate 1310 is provided which has a cladding layer 1320 on its top surface. The substrate can be, for example a silicon substrate. In some cases, the substrate is a transparent material such as SiO2, and the cladding layer is an opaque material such a metal e.g. aluminum. The cladding layer has a plurality of nanoscale apertures 1330 extending through the cladding layer, exposing portions of the top surface of the substrate 1310. In step I, an aperture constriction layer 1340 is selectively grown on the cladding layer. As this constriction layer grows in from the walls of the aperture, it makes the aperture smaller, exposing a fraction of the substrate surface that was exposed prior to growing the constriction layer. After the growth of the constriction layer, in step II, the portion of the surface that is left exposed 1350 is treated with agents that react with the surface in order to deposit functional groups onto the surface of the substrate. The deposition can be selective to the substrate surface as shown in FIG. 13, or the deposition can be non-selective, adding functional groups to both the substrate and the constriction layer surfaces. In step III, the aperture constriction layer is removed to leave an island of functionality 1360 within the aperture that can be used for further selective coupling to the surface of the substrate.

In some aspects, the invention is directed toward a method for producing an island of functionalizing agent in an array of ZMW's comprising: a) providing a substrate having on its surface a cladding layer, wherein the cladding layer comprises an array of apertures disposed through the cladding layer to the substrate, the apertures having side walls; b) selectively growing an aperture constriction layer on the cladding layer such that the aperture constriction layer extends in from the side walls of the aperture to reduce the cross-sectional dimensions of the aperture; c) attaching functionalizing agent to exposed regions of the substrate within the apertures; and d) removing the aperture constriction layer whereby an array of apertures, each having an island of functionalizing agent is produced.

In some cases, the aperture has a generally cylindrical profile and has a diameter that is from about 70 nm to about 300 nm, or from about 90 nm to about 200 nm. In some cases, the island that is formed is from about 5 nm to about 50 nm, or from about 10 nm to about 40 nm.

The constriction layer can be, for example a polymer such as an organic polymer, a metal, or a metal oxide or nitride. The growth of the constriction layer can be produced, for example, by polymerization, electrochemical processes such as electroplating or electrodeposition, by oxide growth, or by chemical vapor deposition (CVD).

In some embodiments the constriction layer comprises a polymer that is grown from the side walls of the cladding. This can be accomplished by selectively depositing an initiator onto the cladding layer and then growing a polymer from the initiators using well known organic polymer synthesis chemistry. This can be accomplished, for example, by depositing onto the cladding a co-polymer consisting of an initiator and a passivator. In some cases, the cladding is aluminum, and the passivator comprises a polymeric component that selectively binds to aluminum. Such cladding selective polymeric components are described, for example in U.S. Patent Application Publication No. 2008/0032301 filed Mar. 29, 2007. An example of a copolymer that comprises an initiator and a passivator is poly(vinylphosphonic acid-co-hydroxyethylmethacrylate)

In some cases a degradable linker is used that has at one end a group that specifically attached to the cladding, in the middle a linker, and at the end an initiator or polymer growth site. Where the cladding is a metal such as aluminum, the group that attaches to the cladding can be a phosphate or phosphonate group. The linker can be any suitable spacer group. The linker can include a degradable piece that allows for cleavage of within the linker to facilitate removal of the polymer constriction layer. The degradable portion can be, for example, a group that is cleaved with light, heat, acid, base, or catalyst. The polymer growth site is a site at which the polymer begins to grow after polymer synthesis is initiated. The polymer synthesis can be free-radical, e.g. azo initiated, or light activated. In some cases the linker can comprise a bidentate linker held together with an azo initiating group. Examples of such linkers include compounds (I), (II), and (III) shown below.

and 2,2'-Azobis[2-methyl-N-(2-hydroxyethyl)propionamide. In some cases, the phosphate groups are protected, e.g. as methyl groups prior to the coupling reaction. In some cases, the groups can be made by forming the amide bonds in the chain using carbodiimide coupling.

The chemistry used to synthesize the polymers from the walls can be any suitable polymerization chemistry. For example, the polymers can be grown either through a random graph polymerization (RGP) or via a living radical polymerization. The polymers can be grown, for example, using ring opening polymerization (ROP) or light-initiated polymerization. The polymer can be a copolymer such as poly(vinylphosphonic acid-co-hydroxyethylmethacrylate). The thickness of the constriction layer can be controlled by controlling the length of the polymer molecules using polymerization conditions. Time, temperature, type of solvent, and concentrations of reaction components can be used to control the polymerization rate. Where the polymerization solvent comprises water, the pH, the level and type of cosolvent, and the level and type of ions in solution can also be used to control the extent of reaction, thereby controlling the thickness of the polymer on the walls. There will generally be a range of lengths of polymer generated by the polymerization procedure. It is generally desired to choose conditions that provide a relatively narrow range of polymer lengths. This can be accomplished in part by selecting polymerization chemistry that tends to have a low level of polydispersity.

Once the polymer constriction layer is produced, the open portion of the substrate, for example a transparent substrate such as fused silica is treated with reagents to produce a functionalized surface. The functionalized surface will generally comprise coupling groups for attaching single molecules or single particles. The polymeric constriction layer is then removed from the walls, leaving an island of functional

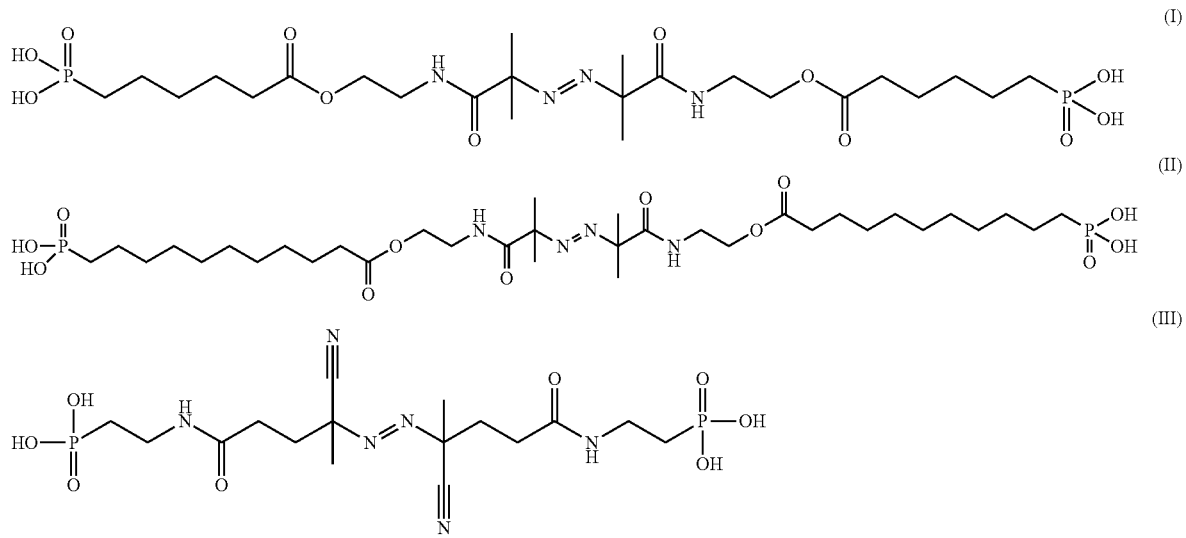

Each of the phosphate groups can bind to the surface, producing two free-radical initiation/polymerization sites upon activation. In some cases the linkers include hydrophobic portions such as chains of methylene groups from about 3 to about 20 in length can be useful. Compounds I and II can be made by forming the ester group, for example using a carbodiimide coupling reaction. For example, compound I can be formed with a dicyclohexyl carbodiimide coupling in THF with in the presence of DMAP from 6-phosphohexanoic acid groups. The functional groups can comprise one or more silanes, for example functionalized silanes, such that the silane portion of the molecule can couple to the surface allowing the functional part of the silane to act as a coupling group. In some cases, the molecule or particle of interest is attached to the island of functional groups before removal of the polymer, and in other cases, the functional groups after the polymeric constriction layer is removed. The removal of the polymers can be accomplished in a variety of ways depending on the type of polymer that is used to coat the walls. Heat, light, solvents, acids, bases, and catalysts can be used to remove the polymer. The polymers can be designed to have groups along the backbone that will break down, fragmenting the polymer into smaller pieces to facilitate removal Examples of polymers to use in the constriction layer that are degradable by acid or hot water are poly(lactic acid) and poly(caprolactone). See e.g. Yang et al. "Surface-Initiated Ring-Opening polymerization of ε-Caprolactone from the surface of PP Film", J. appl. Poly. Sci., 2007, 105, 877-884.

In some cases, after removal of the constriction layer, the portions of the substrate exposed by removal of the constriction layer are treated with a passivating compound such as a silane in order to prevent unwanted binding of other components. This passivation can be carried out, for example, in cases where the molecule or particle of interest is attached after removal of the constriction layer. The passivation can be performed to prevent unwanted binding of the molecule or particle of interest to the exposed portions of the surface.

The constriction layer can be formed by electroplating or electrodepositing onto the surface of the cladding. This can be useful, for example, when the cladding comprises a conductive material such as a metal. Electrodeposition is a process of producing a coating, either metallic or non-metallic, on a surface by the action of electric current. The deposition of a metallic coating onto an object is generally achieved by putting a negative charge on the object to be coated and immersing it into a solution which contains a salt of the metal to be deposited (i.e., the object to be plated is made the cathode of an electrolytic cell). The metallic ions of the salt carry a positive charge and are thus attracted to the object. When they reach the negatively charged cladding, the cladding provides the current required to reduce the positively charged ions to metallic form. The metal that is plated is different than the cladding to allow for subsequent removal without removing the cladding. Electrodeposited metals include copper, nickel, gold, silver, chrome, cadmium, bronze, rhodium, black nickel, and zinc. In some cases non-metals can be electrodeposited as the constriction layer. In such cases, the cladding can be the anode or the cathode of the electrochemical system. Electrodeposition processes useful in the invention are described, for example, in Paunovic et al. "Fundamentals of Electrochemical Deposition", Wiley, New York, 1998, the contents of which are incorporated by reference herein for all purposes.

One aspect of the invention comprises using the oxidation methods of the invention in order to produce an island of functionality within the ZMW and to achieve high loadings of the single molecules of interest. The methods can be used, for example, to obtain higher loadings of single molecules than can be achieved through Poisson-limited analyte loading. Higher loadings of single molecules can be obtained by having a small region (an island) of functional groups or coupling agent within the ZMW.

An aspect of the invention is a method for obtaining an island of functionality at the bases of an array of ZMWs comprising: providing an electrochemical system comprising a working electrode, a counter electrode, and optionally a reference electrode; providing a substrate having a lower transparent layer and an upper cladding layer, wherein the cladding layer comprises an array of apertures disposed through the reflective layer to the transparent layer, the apertures having side walls, wherein the cladding layer comprises the working electrode; applying a voltage to the working electrode such that a layer of oxide is formed onto the side walls of the aperture, attaching functionalizing agent to exposed regions of the transparent layer within the apertures; and dissolving the oxide layer from the walls of the aperture whereby islands of functionalizing agent are formed within the apertures.

Figure 14:
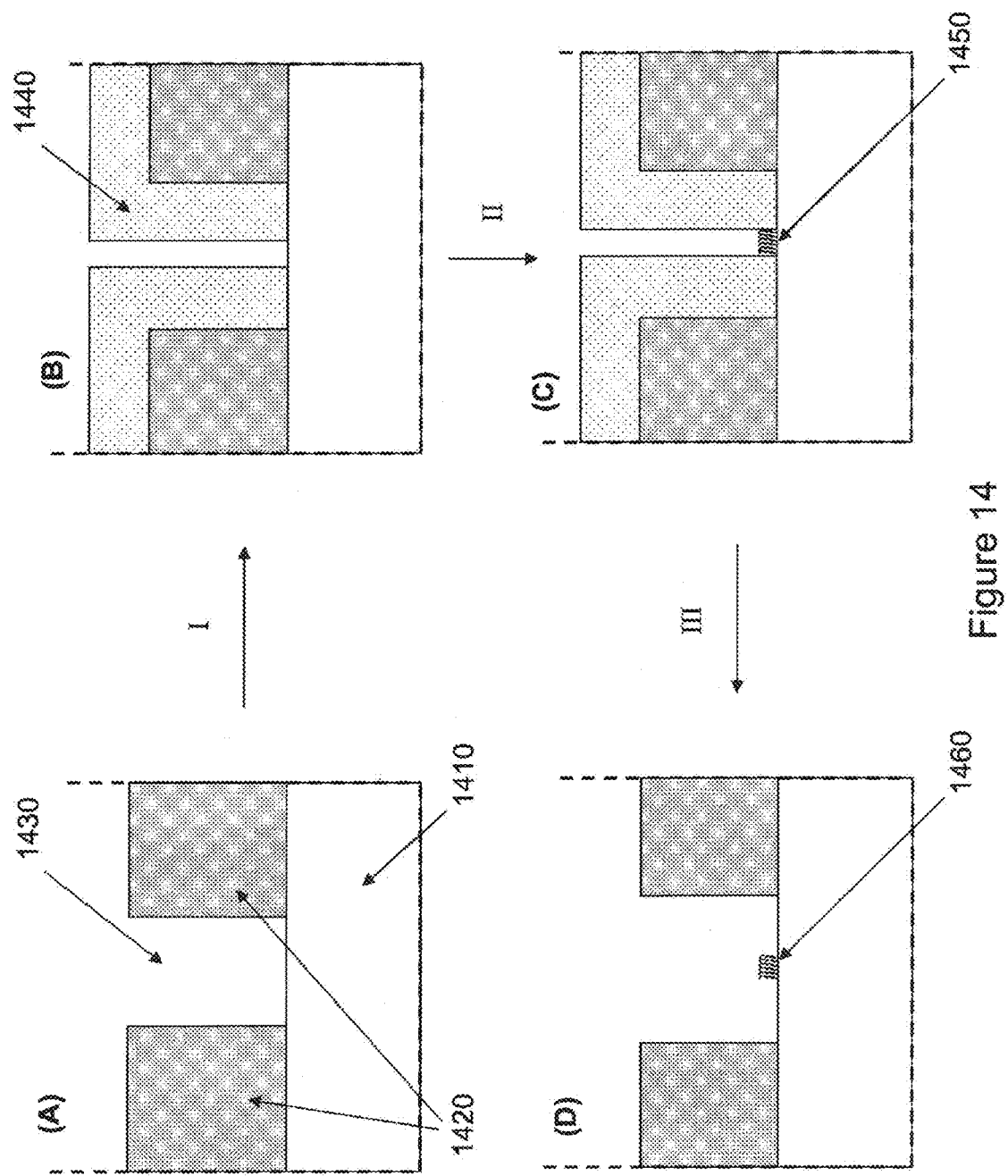
FIG. 14 illustrates an embodiment of a method of the invention for producing an island of functionality within the ZMW using oxidation of the cladding.

FIG. 14 show an illustration of an embodiment of the invention in that produces islands of functionalizing agent within a ZMW by growing an oxide layer onto the cladding. FIG. 14(A) shows a portion of a substrate having an array of apertures 1430 through cladding layer 1420 to transparent layer 1410. In step I, an oxide layer 1440 is grown onto cladding layer 1420. The oxide can be grown thermally, with plasma treatment, or electrochemically. In order to grow the oxide electrochemically, for example, the cladding layer is attached to a power supply such that the cladding can act as the working electrode in an electrochemical system. The working electrode and a counter electrode are placed into an electrolyte solution and the electrochemical oxidation is carried out such that an oxide layer 1440 is formed from the cladding layer. As described above, the oxidation process generally results both in an oxide layer extending out from the walls, and also in the oxide layer extending into the cladding layer as the cladding material is consumed to form the oxide layer. Therefore the oxide extends into the ZMW and the ZMW cross-section becomes larger. After step I, a shown in FIG. 14(B), a smaller portion of the transparent substrate is now exposed than before the process. In step II, a functionalizing agent 1450 is attached to the transparent surface. For the embodiment shown in FIG. 14(C), the functionalizing agent is attached using a selective process such that little or no functionalizing agent becomes attached to the oxide layer on the walls of the ZMW. In other embodiments, functionalizing agent that is less selective or that is completely non selective can be used. Functionalizing agent attached to the walls will tend to be remove in step III of the process. In step III, the oxide is dissolved, for example, using acidic aqueous solution. The removal of the oxide from the walls produces a ZMW structure having an island of functionalizing agent 1460 within the ZMW.

Attachment of functional agents to the transparent materials may be carried out by any of a variety of methods known in the art. For example, in the context of silica based substrates, e.g., glass, quartz, fused silica, silicon, or the like, well characterized silane chemistries may be used to couple other agents to the surface. Such other agents may include functional groups, activatable groups, and/or linker molecules to either of the foregoing, or the actual molecules of interest that are intended for use in the end application of the surface. In some cases the functional groups comprise coupling groups for coupling a molecule of interest or an intermediate to the surface. In the context of other transparent material types, e.g., polymeric materials, or the like, other processes may be employed, e.g., using hybrid polymer surfaces having functional groups coupled thereto or extending from the polymer surface using, e.g., copolymers with functional groups coupled thereto, metal associative groups, i.e., chelators, thiols, or the like.

Where the transparent material comprises a silica-based surface, silanes (e.g., methoxy-, or ethoxy-, silane reagents) can form stable bonds with silica surfaces via Si—O—Si bond formation, and are less reactive to metal or metal oxide surfaces such as aluminum or aluminum oxide surfaces under appropriately selected reaction conditions (e.g., vapor phase, solution-based treatments). Silanes, for example, silanes modified with coupling groups for attachment of enzymes or other molecules of interest (e.g., biotin-PEG-silanes such as those described in U.S. patent application Ser. No. 11/240, 662), can thus be used to bind desired molecules to silica surfaces such as those in a ZMW.

In some cases, the coupling groups are activatable or deactivatable coupling groups. A variety of different activatable or deactivatable coupling groups may be used in conjunction with this aspect of the invention. Typically, such groups include coupling groups that are capped or blocked with a selectively removable group. These include groups that are thermally altered, e.g., thermolabile protecting groups, chemically altered groups, e.g., acid or base labile protecting groups, and photo alterable groups, e.g., photo-cleavable or removable protecting groups. Suitable activatable and deactivatable coupling groups are provided, for example, in U.S. patent application Ser. No. 11/394,352.

A variety of different coupling groups may be used in this context, depending upon the nature of the molecule of interest to be subsequently deposited upon and coupled to the substrate. For example, the coupling groups may include functional chemical moieties, such as amine groups, carboxyl groups, hydroxyl groups, sulfhydryl groups, metals, chelators, and the like. Alternatively or additionally, they may include specific binding elements, such as biotin, avidin, streptavidin, neutravidin, lectins or SNAP-Tags™ and their substrates (Covalys Biosciences AG; the SNAP-Tag™ is a polypeptide based on mammalian O6-alkylguanine-DNA-alkyltransferase, and SNAP-tag substrates are derivates of benzyl purines and pyrimidines), associative or binding peptides or proteins, antibodies or antibody fragments, nucleic acids or nucleic acid analogs, or the like. Click chemistry including the Azide-Alkyne Huisgen Cycloaddition catalyzed, for example, by copper can also be used.

Additionally, or alternatively, the coupling group may be used to couple an additional group that is used to couple or bind with the molecule of interest, which may, in some cases include both chemical functional groups and specific binding elements. A preferred set of embodiments utilizes biotin to attach a molecule of interest to the silica-based or transparent substrate. The attachment of biotin or other selective binding group to the surface can be accomplished in a number of ways.

One exemplary approach involves reacting a silica-based surface region with a compound having a silane group directly coupled to the selective binding group, for example, a silane-polyethylene glycol-biotin compound to produce a surface having selective binding groups, e.g. biotin bound to the silica-based region. This method provides a one step process for obtaining a silica-based surface having selective binding groups such as biotin attached thereto. In some cases, the silane compound having the selective binding group is diluted with a silane that does not contain the selective binding group, e.g. silane-polyethylene glycol in order to control the density of selective binding groups on the silica-based surface.

Another exemplary approach involves first reacting a silica-based surface with a coupling agent, and reacting the coupling agent on the surface with an attaching agent that has both functionality for reacting with the coupling agent, and functionality for attaching the desired molecule (e.g. a selective binding agent such as. Biotin). For example, the silica-based surface is reacted with an aminosilane or thiol-silane under conditions where the aminosilane or thiol-silane becomes bound to the substrate. The aminosilane or thiol-silane surface is subsequently reacted with an attaching agent, for example having an activated ester coupled to biotin to link the biotin to the aminosilane surface, or a maleimide group coupled to biotin to link to the thiol-silane surface. The attaching agent can be diluted as described herein with molecules that react, for example, with the aminosilane or thiol-silane, but do not have selective binding groups. This process incorporating an attaching group results in the coupling the selective binding agent to the surface in two steps. While this approach uses two steps rather than the one step described above, it can have some advantages in development, processing, and quality control.

The linking chemistry between the coupling agent and the compound having the selective binding agent can comprise any suitable linking chemistry. The linking chemistry can comprise, for example, thiol-maleimide, anhydride-amine, alkyne-azide, epoxide-amine, or amine-activated ester. As with the one step method, the compound having the selective binding agent can be diluted with a compound with the same reactive functionality, but not having the selective binding agent to control the density of selective binding agent on the surface.

In some cases, the compound comprising the selective binding agent is not diluted with another agent such as a capping agent that can bind to the surface, but does not have selective binding agent. Where there is no dilution, a relatively highly density of selective binding agent can be achieved. This high level of selective binding agent allows either for attaching a relatively high density of molecules of interest to the surface, or can be used to attach relatively few molecules of interest to the surface.

In some cases, the compound comprising the selective binding agent is diluted with another agent such as a capping agent that can bind to the surface, but does not have selective binding agent. In accordance with the invention, the low density of the coupling agent on a surface is designed to provide a single reactive moiety within a relatively large area for use in certain applications, e.g., single molecule analyses, while the remainder of the area is substantially non-reactive. As such, coupling groups can be diluted to provide a low density of reactive groups that are typically present on a substrate surface at a density of reactive groups of greater than $1/1 \times 10^6$ nm$^2$ of surface area, but less than about $1/100$ nm$^2$. In more preferred aspects, the density of reactive groups on the surface will be greater than $1/100,000$ nm$^2$, $1/50,000$ nm$^2$, $1/20,000$ nm$^2$ and $1/10,000$ nm$^2$, and will be less than about $1/100$ nm$^2$, $1/1000$ nm$^2$, and $1/10,000$ nm$^2$. For certain preferred applications, the density will often fall between about $1/2500$ nm$^2$ and about $1/300$ nm$^2$, and in some cases up to about $1/150$ nm$^2$.

The conditions for the attachment of the molecule of interest can be controlled such that, for example, only one molecule of interest or one active molecule of interest is delivered to one or more optical confinements on a surface. In some cases, the conditions for the attachment of the molecule of interest are controlled such that 10%, 20%, 30%, 40%, 50%, 60%, 70%, 80%, 90% or more of the optical confinements have only one molecule of interest or one active molecule of interest. Approaches for obtaining a high fraction of optical confinements having one molecule of interest is described in copending U.S. patent application Ser. No. 12/384,097, which is incorporated herein by reference for all purposes.

Phospholipid chemistries can also be used to functionalize the surface of the transparent or silica-based portions of the substrate. Chemistries using phospholipid compositions, have shown the ability, in the presence and absence of calcium, to form different levels of supported phospholipid bilayers on metal oxide surfaces and silicon dioxide based surfaces. By selecting the lipid composition and the presence or absence of calcium, one can target deposition of molecules, either as blocking or coupling groups, onto the different surface types. For example, one can select a phospholipid that has high binding selectivity for metal oxide surfaces and use it to block the metal portion of the surface. Alternatively, one can utilize a phospholipid with an appropriate coupling group that has high binding selectivity for the underlying glass substrate, and thus selectively couple additional groups to the surface of the transparent or silica-based portion of the substrate. Examples of these selective phospholipid compositions are described in, e.g., Rossetti, et al., Langmuir. 2005; 21(14):6443-50, which is incorporated herein by reference in its entirety for all purposes.

The molecules of interest are generally attached to the coupling agents selectively placed onto the transparent or silica-based portions of the surface as described above. A variety of chemistries are available for specifically attaching a molecule of interest to the coupling agents bound to the surface.

For example, where biotin is bound to the transparent or silica-based regions of the surface, this surface can be used to attach the molecule of interest using a binding agent such as streptavidin, which has a very high affinity for biotin. In one approach, the molecule of interest has a biotin tag which can then be attached to the surface using an intermediate binding agent, e.g., streptavidin, which acts to bind to both the surface and the molecule of interest. In another approach, streptavidin is attached directly to the molecule of interest.

A variety of analytes can be delivered to reaction/observation regions using the methods and compositions herein. These include enzyme substrates, nucleic acid templates, primers, etc., as well as polypeptides such as enzymes (e.g., polymerases).

Similarly, a wide variety of proteins, e.g., enzymes, can also be delivered using the methods herein. A variety of protein isolation and detection methods are known and can be used to isolate enzymes such as polymerases, e.g., from recombinant cultures of cells expressing the recombinant polymerases of the invention. A variety of protein isolation and detection methods are well known in the art, including, e.g., those set forth in R. Scopes, *Protein Purification*, Springer-Verlag, N.Y. (1982) and *Handbook of Bioseparations*, Academic Press (2000). Sambrook, Ausubel, Kaufman, and Rapley supply additional useful details.

For a description of polymerases and other enzymes that are active when bound to surfaces, which is useful in single molecule sequencing reactions in which the enzyme is fixed to a surface (e.g., to a particle or to a wall of a reaction/observation region, e.g., in a ZMW), e.g., conducted in a ZMW, see Hanzel et al. ACTIVE SURFACE COUPLED POLYMERASES, WO 2007/075987 and Hanzel et al. PROTEIN ENGINEERING STRATEGIES TO OPTIMIZE ACTIVITY OF SURFACE ATTACHED PROTEINS, WO 2007/075873). For a description of polymerases that can incorporate appropriate labeled nucleotides, useful in the context of sequencing, see, e.g., Hanzel et al. POLYMERASES FOR NUCLEOTIDE ANALOGUE INCORPORATION, WO 2007/076057. For further descriptions of single molecule sequencing applications utilizing ZMWs, see Levene et al. (2003) "Zero Mode Waveguides for single Molecule Analysis at High Concentrations," *Science* 299:682-686; Eid et al. (2008) "Real-Time DNA Sequencing from Single Polymerase Molecules" *Science* DOI: 10.1126/science.322.5905.1263b; Korlach et al. (2008) "Selective aluminum passivation for targeted immobilization of single DNA polymerase molecules in zero-mode waveguide nanostructures" *Proceedings of the National Academy of Sciences U.S.A.* 105(4): 1176-1181; Foquet et al. (2008) "Improved fabrication of zero-mode waveguides for single-molecule detection" *Journal of Applied Physics* 103, 034301; "Zero-Mode Waveguides for Single-Molecule Analysis at High Concentrations" U.S. Pat. No. 7,033,764, U.S. Pat. No. 7,052, 847, U.S. Pat. No. 7,056,661, and U.S. Pat. No. 7,056,676, the full disclosures of which are incorporated herein by reference in their entirety for all purposes. In some cases, the enzyme can be covalently attached to the substrate through functional groups on the enzyme such as amine, carboxylate, or thiol groups, for example with NHS or maleimide linking chemistry.

In order to attach an enzyme to the surface, binding elements can be added to the polymerase (recombinantly or, e.g., chemically) including, e.g. biotin, avidin, GST sequences, modified GST sequences, e.g., that are less likely to form dimers, biotin ligase recognition (BiTag) sequences, S tags, SNAP-tags, enterokinase sites, thrombin sites, antibodies or antibody domains, antibody fragments, antigens, receptors, receptor domains, receptor fragments, ligands, dyes, acceptors, quenchers, or combinations thereof.

Multiple surface binding domains can be added to orient the polypeptide relative to a surface and/or to increase binding of the polymerase to the surface. By binding a surface at two or more sites, through two or more separate tags, the polymerase is held in a relatively fixed orientation with respect to the surface. Further details on attaching tags is available in the art. See, e.g., U.S. Pat. Nos. 5,723,584 and 5,874,239 for additional information on attaching biotinylation peptides to recombinant proteins.

By controlling the starting dimensions of the chip and the oxidation conditions, the size of the island and the distance between the island and the walls of the ZMW can be controlled. The process can be used to produce an island of functionalizing agent which is small enough that only a small number of molecules of interest can be effectively bound. In some cases, the island of functionalizing agent can be small enough that only one molecule of interest can become effectively bound to each ZMW. For example, one can begin with a ZMW array on fused silica with an aluminum layer of about 100 microns having apertures with circular cross-sections with diameters of about 60 nm. An oxidation at about 20 V in a polyphosphonates electrolyte will result in a ZMW diameter of about 82 nm, having an oxide layer with a hole with a diameter of about 5 nm. This substrate can then be treated with a functionalizing agent such as biotin-PEG-silane. The oxide layer is subsequently removed using an acid bath. The result of this process is a ZMW having a diameter of about 82 nm having an island of biotin functionality of about 5 nm. A molecule of interest, such as a polymerase enzyme-template-primer complex can then be bound to the island of functionality. Where the radius of gyration of the molecule of interest is greater than about 5 nm, the binding of one molecule of interest will block subsequent binding, allowing for the production of an array of ZMWs, each having one molecule of interest at loadings greater than the 37% which can be obtained using Poisson-limited analyte loading.

In some cases, it is desirable to have both the island of functionality and a non-reflective layer on the walls of the ZMW. This can be accomplished, for example by incomplete dissolution of the oxide layer to leave a portion of the oxide layer on the walls. Alternatively, this can be accomplished by subsequently adding a non-reflective layer by the methods described herein after the formation of the island and dissolution of the oxide layer. The non-reflective layer can be produced for example, by performing a second oxidation after the formation of the island of functional agent.

The binding of one or more molecules of interest to the island can be carried out either before or after step III. If the molecule of interest is inhibited or degraded by the conditions used to dissolve the cladding walls, it will generally be attached after step III.

Step III can be carried out using compounds which selectively remove oxide from a metal surface. In some cases the oxide is removed with an acidic aqueous solution. Post-etch residue removers can be employed for the selective removal of the oxide from the metal cladding. Residue removers from Dupont, such as those from EKC Technologies, including the EKC600 series of materials can be used. In some cases, an aqueous solution of EKC640 is applied at around 30 degrees C. to a substrate with an aluminum cladding to selectively remove aluminum oxide. In some cases compounds comprising phosphonic acids such as polyvinyl phosphonic acid or polyacrylic-polyvinylphosphonic acid are used to remove the oxide. Generally phosphonic acid compounds at a concentration from about 0.1 percent to about 4 percent are used. In some cases, these compounds are used at a concentration from about 0.1 to about 1 percent. In some cases, we have found that higher concentrations of phosphonic acid based compounds can provide superior results. Thus, in some cases, phosphonic acid compounds at a concentration from about 1.5 percent to about 3 percent are used. At the higher concentrations, it is believed that the oxide becomes more unstable due, at least in part to the lower pH. In some cases a pH of less than 4 is desired. Phosphonic acids are useful as they can be formulated to have a high reactivity with metals such as aluminum, but very little reactivity with silica or functionalized silica surfaces, such as silane treated silica surfaces.

Arrays of Nanostructures

The methods described herein can also be used to produce an array of nanostructures on a substrate. This can be accomplished, for example, by attaching a nanoparticle to a patch of functionalizing agent produced on the surface. In one exemplary embodiment, in step II of FIG. 13, treatment with thiol-alkane-silane can be used to produce a patch of thiol functionalizing agent. Treatment of the structure of FIG. 13(C) with gold nanoparticles will result in only particles that can fit into the channel will become attached. In addition to only having one gold particle attached per functional patch, the walls of the oxide can assist in localizing the particle. Alternately, the structure of FIG. 13(D) can be treated with gold nanoparticles having a size on the order of the functionalized island. This will result in the attachment of only one nanoparticle per island, and the attached particle will prevent the attachment of subsequent particles.

One aspect of the invention is a method for producing an array of nanostructures comprising: providing a substrate having a top surface, the top surface having an aperture layer, the aperture layer having a plurality of apertures extending through the aperture layer to the substrate, the apertures having one or more cross-sectional dimension; oxidizing the substrate whereby an oxide layer is formed on the aperture layer, whereby a cross sectional dimensions of the aperture is brought to 50 nm or smaller; treating the substrate with a functionalizing agent whereby the functionalizing agent becomes attached to the exposed portions of the substrate; exposing the substrate to nanostructures to attach the nanostructures to the functionalizing agent attached to the substrate; and dissolving the oxide layer.

Oxidation to Produce Nanopores of Controlled Size

In some cases, it is desirable to produce nanopores having controlled pore dimensions. Conventional methods of forming microstructures, such as photolithography and etching may not be effective at forming nanopores having dimensions on the order of 10 nm. One aspect of the invention is a method of forming an array of nanopores by using oxidation to reduce the dimensions of larger holes.

One aspect of the invention is a method for forming an array of nanopores comprising: providing a substrate comprising an array of apertures extending therethrough, the apertures having one or more cross-sectional dimensions; and oxidizing the substrate whereby an oxide layer is formed on the substrate whereby the formed oxide lowers an aperture dimension to 20 nm or less.

Figure 15:
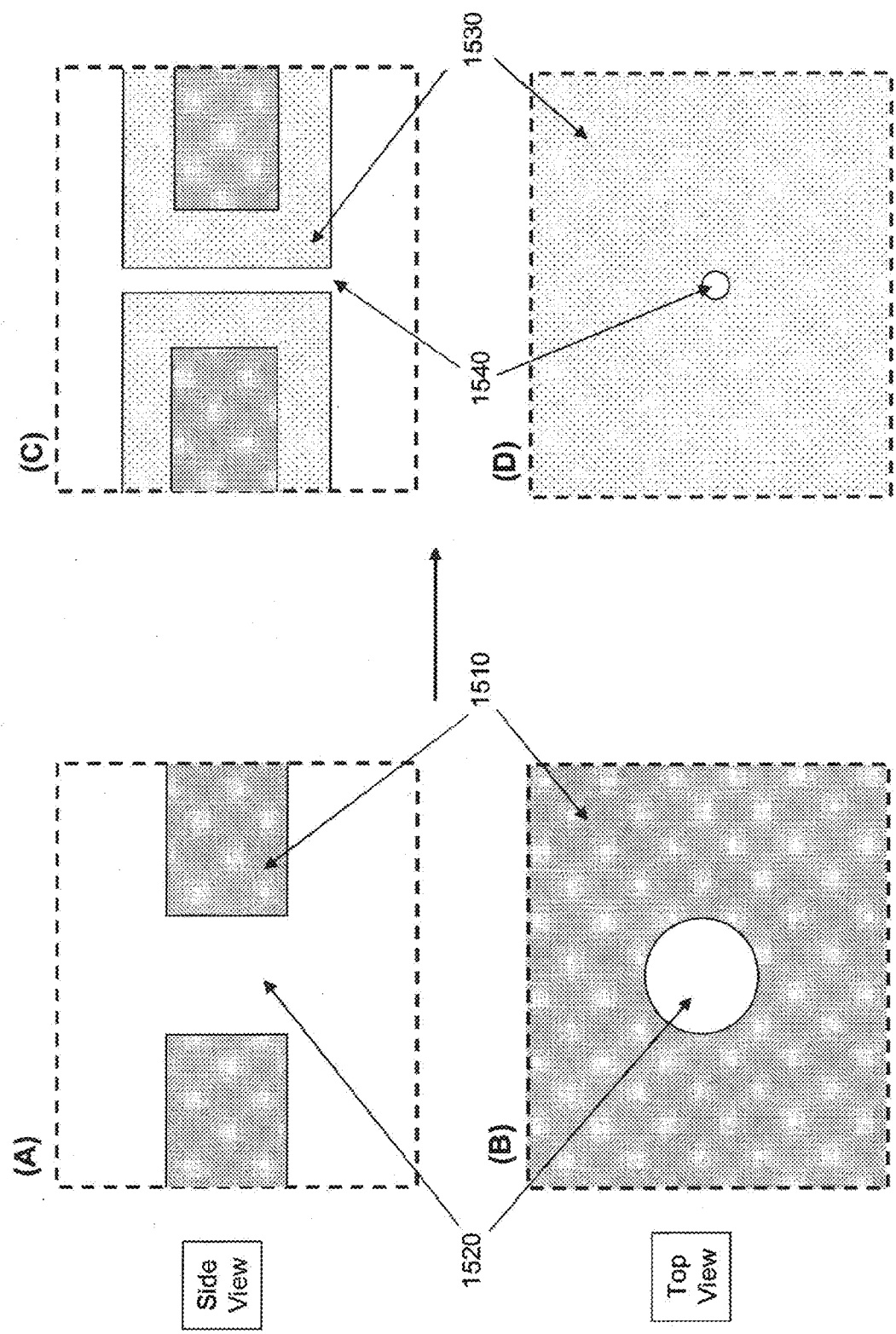
FIG. 15 illustrates an embodiment of a method of the invention for producing nanopores.

FIG. 15 illustrates an embodiment of the invention in which an array of nanopores is formed by oxidizing a substrate having an array of holes to form an oxide layer such that an array having smaller nanoscale holes is formed. FIGS. 15(A) and 15(B) show a side view and a top view respectively of a portion of a substrate 1510 having an array holes or apertures 1520 extending therethrough. The substrate is oxidized, for example by the methods described herein such as by thermal, plasma, or electrochemical oxidation to produce a layer of oxide, resulting in the structure shown in FIGS. 15(C) and 15(D). The resulting substrate has a layer of oxide 1530 that lowers the diameter of the hole or aperture 1540. The resulting aperture has cross sectional dimensions on the scale of nanometers. The starting hole or aperture 1520 can have, for example, a cross sectional dimension of about 500 nm to about 20 nm. The resulting hole after oxidation 1540 can have, for example, a cross sectional dimension of about 100 nm to about 1 nm. The methods of the invention are particularly useful for producing apertures of 20 nm or less, 10 nm or less, 5 nm or less, 2 nm or less, or 1 nm or less.

The cross-sectional dimension after oxidation can be, for example, 75%, 50%, 40%, 30%, 25%, 10%, 5%, or 1% of the cross-sectional dimension prior to oxidation. The final cross-sectional dimension can be from about 1% to about 75%, or about 5% to about 50% of the cross-sectional dimension after oxidation.

The nanopores can have any suitable cross-sectional shape. The cross-sectional shape can be, for example, circular, elliptical, square, or slits. In some cases, the apertures have a cross-sectional shape that is a circle, and the cross-sectional dimension is the diameter of the circle.

For example, one can begin with an array of holes in an aluminum layer of about 100 microns in thickness having apertures with circular cross-sections with diameters of about 60 nm. The aluminum layer may have a support layer that supports the aluminum layer structurally, while leaving the holes accessible. An oxidation at about 20 V in a polyphosphonates electrolyte will cause the buildup of oxide within the holes resulting in the production of a hole with a diameter of about 5 nm.

The substrate in which the nanopores are formed can be any suitable material on which a stable oxide can be formed. The substrate can be, for example, a metal such as aluminum. The substrate can be a semiconductor such as silicon. The methods described herein for controlled oxidation of can be used to produce nanopores.

The nanopores of the invention can be used, for example, in sequencing applications which involve passing a nucleic acid strand through the nanopore. The invention allows for the efficient production of arrays of nanopores having controlled, small dimensions. The methods allow for the fine-tuning of the dimensions of the nanopore by controlling the oxidation conditions.

EXAMPLES

Example 1

Electrochemical Anodization of ZMW Array

Figure 16:
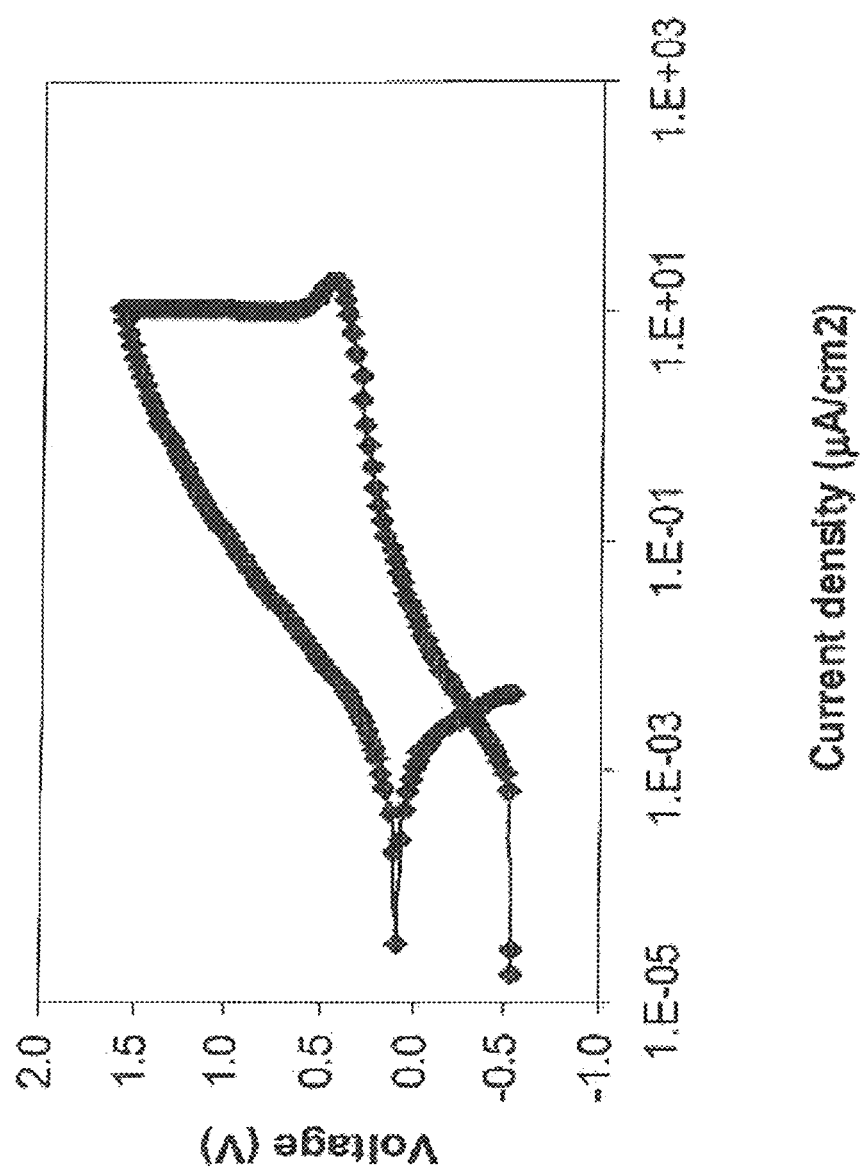
FIG. 16 is a plot of current density versus voltage for the electrochemical anodization of a zero-mode-waveguide.
Figure 17:
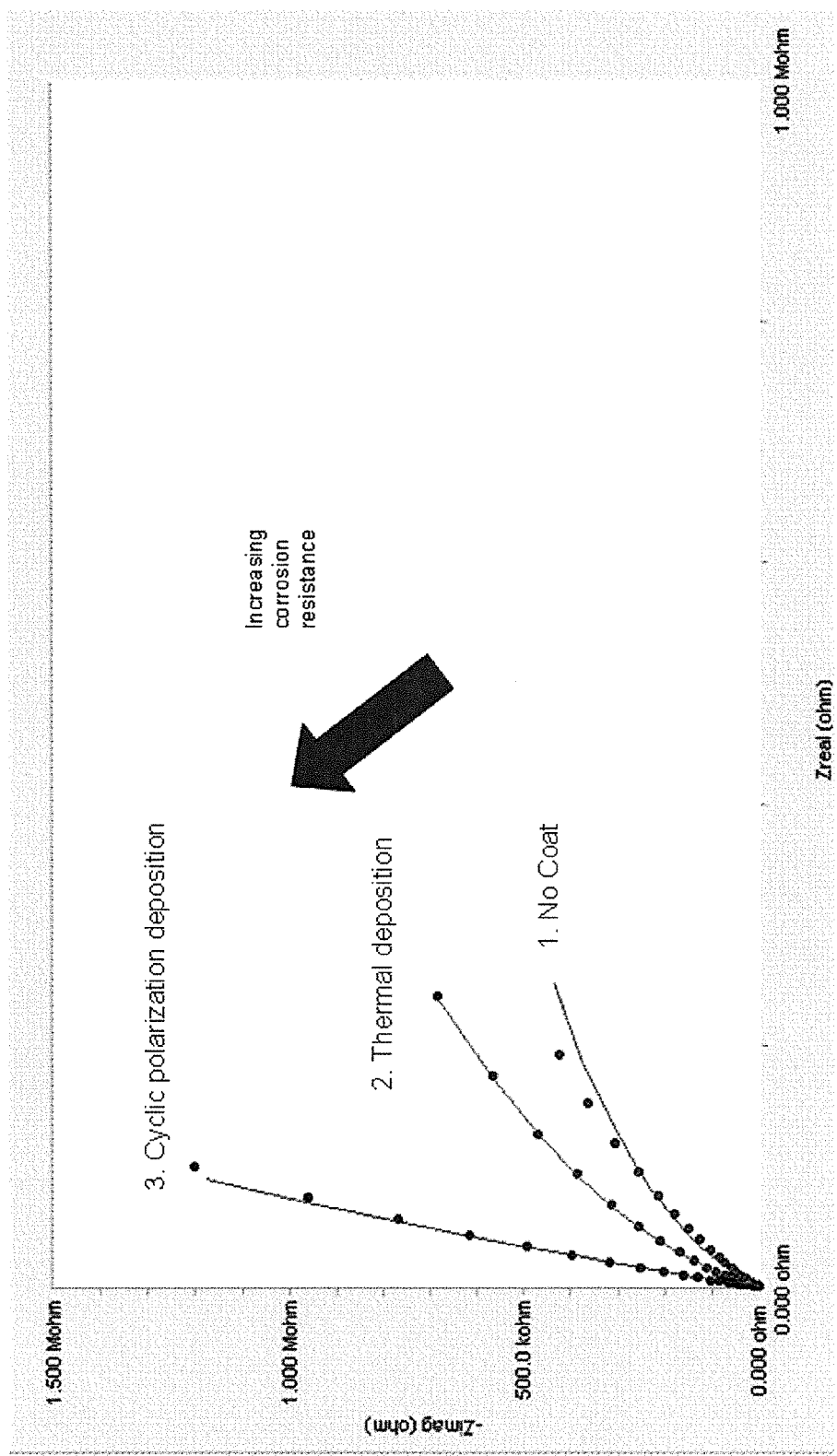
FIG. 17 is a plot of impedance spectroscopy data showing improved stability for an electrochemically anodized zero-mode-waveguide.

Electrochemical oxidation in the presence a poly(vinyl phosphonic acid) (PVPA) electrolyte was carried out using a three-electrode electrochemical cell equipped with a graphite counter electrode and a saturated calomel reference electrode. The metal cladding of the optical confinement array acted as the working electrode. FIG. 16 shows a cyclic polarization curve for the anodization of an anodization carried out with a solution of poly(vinyl phosphonic acid) (PVPA). The current density stabilized at a value of 10 µA per $cm^2$, indicating the formation of a passive oxide layer. Upon returning the voltage to the open circuit potential, the current drops, indicating that a passivation layer has formed on the Al surface. Scanning electron microscope (SEM) analysis of a cross-section of the ZMW after the electrochemical anodization shows a thick layer of oxide. In some cases, a thin bright line is seen which is believed to be a phosphonate-rich passivation coating. The improved corrosion resistance of the ZMW can be seen using impedance spectroscopy. FIG. 17 shows electrochemical corrosion measurements carried out in the buffers that are used for sequencing. Curve 1 is a ZMW that was not passivated. Curve 2 is a ZMW passivated with PVPA thermally (without electrochemical treatment). The impedance spectroscopy results show that the electrochemical anodization in the presence of phosphonates results in a significant improvement in corrosion resistance. Exposure of the electrochemically passivated surface to labeled neutravidin beads and to polymerase showed that the passivated surfaces were also inert with respect to deposition of biomolecules such as proteins.

Example 2

Anodization of a Wafer

A fused silica wafer having an aluminum cladding layer with arrays of apertures having diameters of about 100 nm formed on the wafer is cleaned by sonication in acetone, after which it is dried, and subjected to a light plasma etch. Approximately 1 L of a 0.4% solution of poly(vinylphosphonic acid) is added to a 1 L beaker. The wafer is clipped to a wire connected to the anode of a power supply, and a graphite sheet is clipped to a wire connected to the cathode of the power supply, and both the wafer and the graphite sheet are immersed into the beaker. The power supply is turned on, and the desired voltage is applied. After 3 to 5 minutes, the power supply is turned off, and the wafer is removed and rinsed with water and dried. The wafer can then be diced into chips sized about 9 mm by 9 mm for subsequent evaluation.

Example 3

TEM Images of ZMWs Having Non-Reflective Layers on their Walls

ZMW structures having non-reflective walls were produced by electrochemical anodization as described herein. The resulting arrays were prepared for transmission electron microscopy (TEM). Samples for transmission electron microscopy were cross-sectioned using a dual beam focused ion beam (FIB). Prior to sectioning, layers of platinum and chromium were deposited on the substrates.

Figure 18:
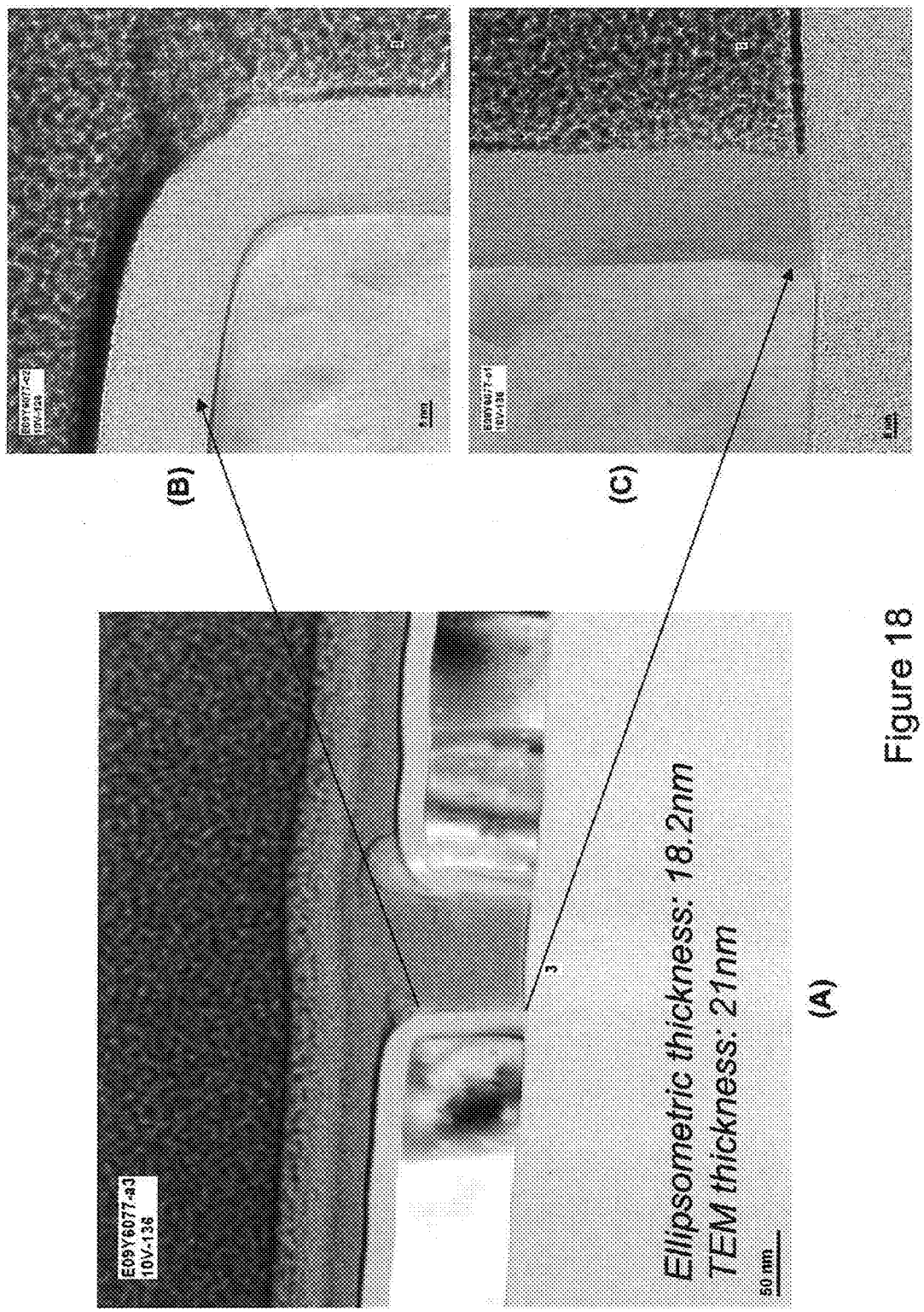
FIGS. 18 and 19 show a TEM images of a cross section of a ZMW structure of the invention prepared in the presence of PVPA by applying 10V.
Figure 19:
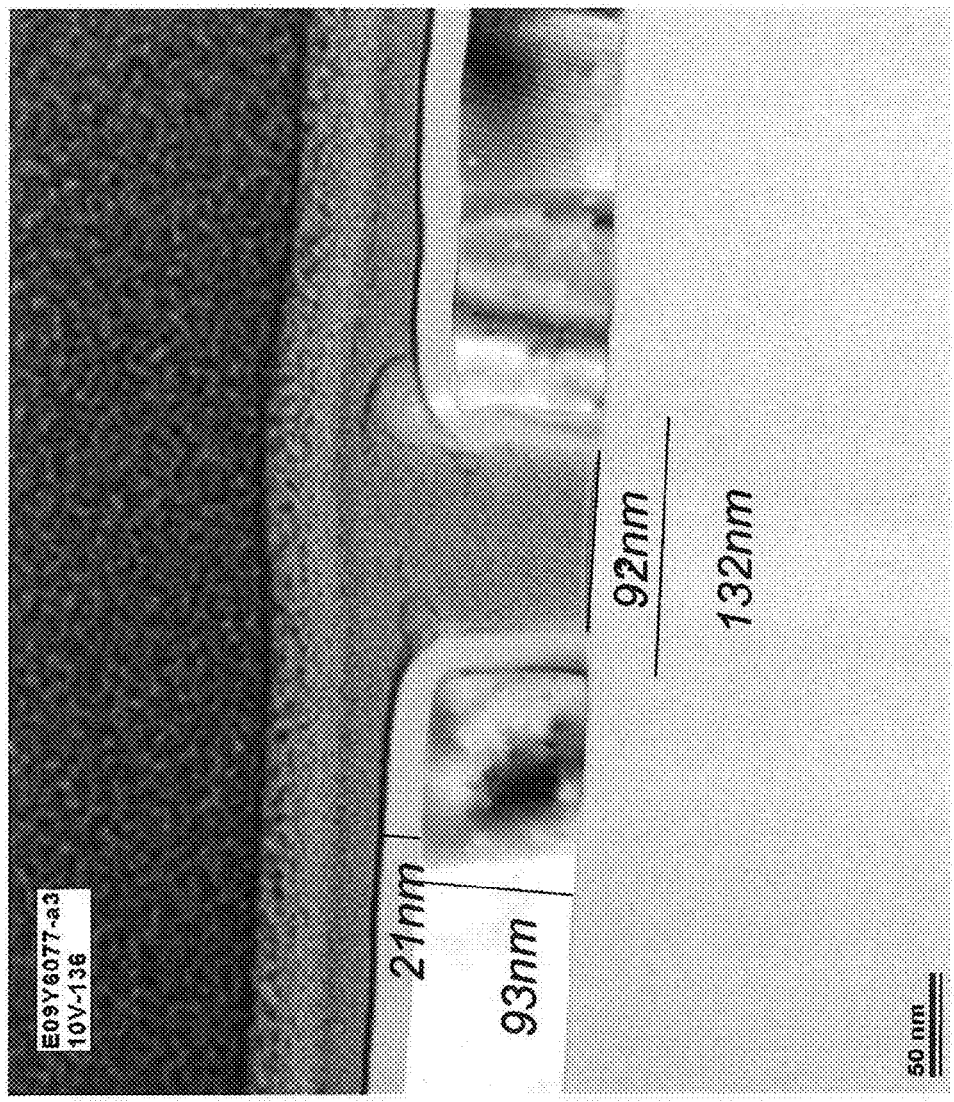

FIG. 18 shows a TEM image of a cross section of a ZMW structure of the invention prepared in the presence of PVPA by applying 10V. FIG. 18(A) shows that the ZMW has a layer of oxide on its walls and on the top surface of the cladding. FIGS. 18 (B) and (C) show close up view of the structure. The thickness of the oxide layer by TEM was determined to be about 21 nm. The thickness of the oxide layer as determined by ellipsometry was about 18 nm. FIG. 19 shows another SEM of the ZMW produced by oxidation at 10 V in which the dimensions are shown. The thickness of the cladding layer is about 93 nm, the thickness of the non-reflective oxide layer is about 21 nm, the diameter of the ZMW is about 132 nm, and the diameter of the region within the non-reflective layer is about 92 nm.

Figure 20:
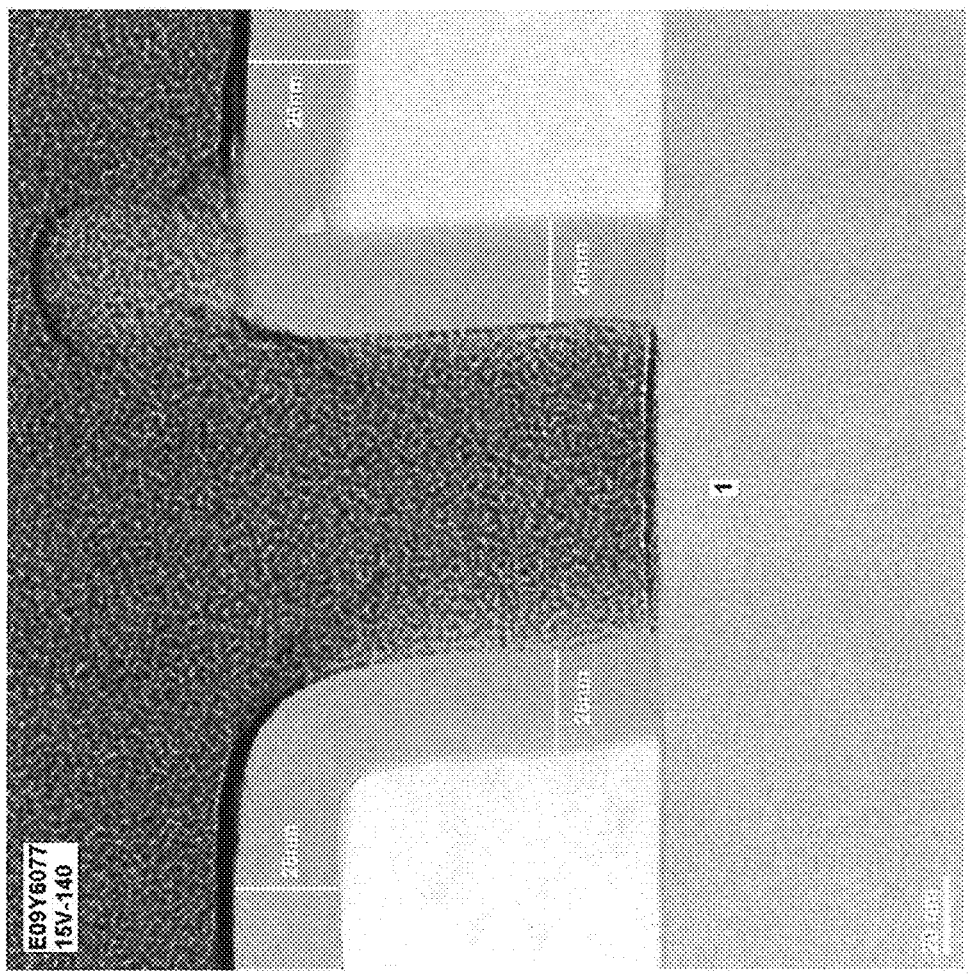
FIG. 20 shows a TEM image of cross-section of a ZMW structure produced by oxidation in the presence of PVPA at 15 V.

FIG. 20 shows a TEM image of cross-section of a ZMW structure produced by oxidation in the presence of PVPA at 15 V. The thickness of the oxide layer is about 26 nm.

Figure 21:
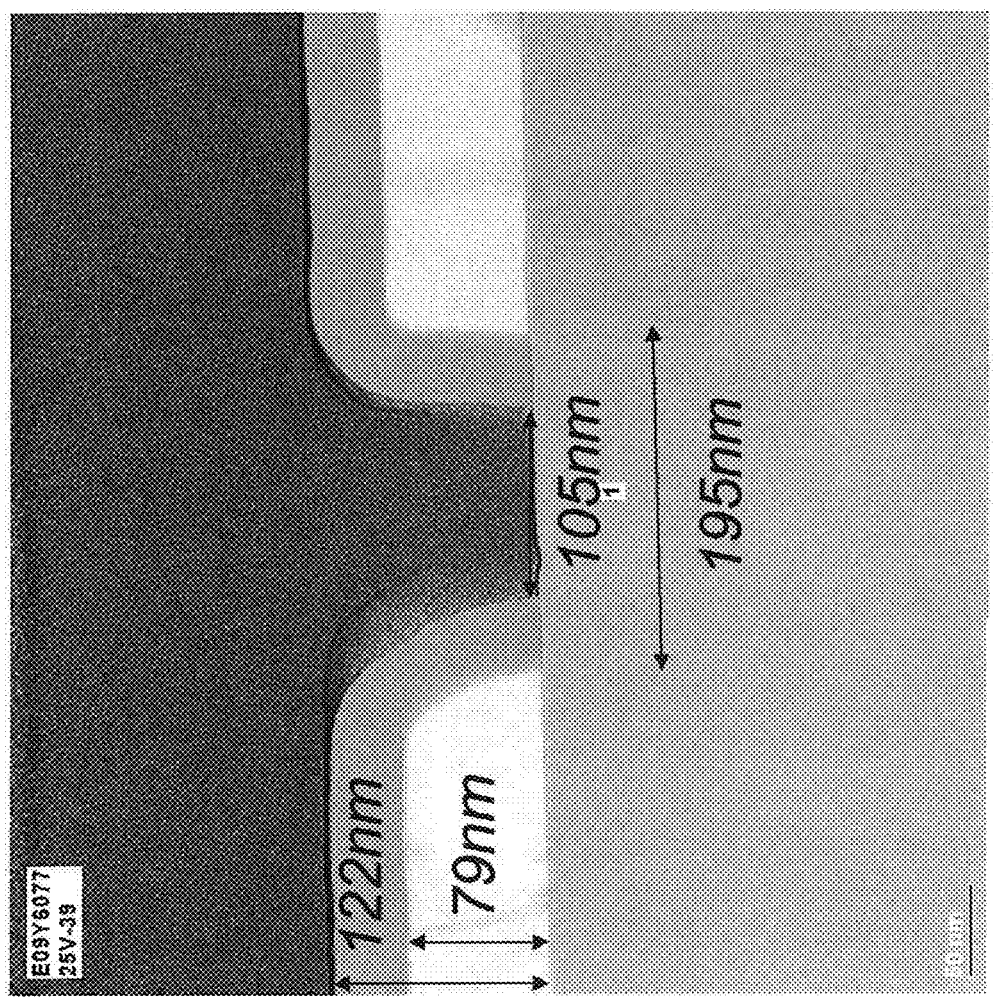
FIG. 21 shows a TEM image of cross-section of a ZMW structure produced by oxidation in the presence of PVPA at 25 V.

FIG. 21 shows a TEM image of cross-section of a ZMW structure produced by oxidation in the presence of PVPA at 25 V. The thickness of the cladding layer is about 79 nm, the diameter of the ZMW is about 195 nm, and the diameter of the region within the non-reflective layer (the solution volume) is about 105 nm. The thickness of the oxide layer is between about 43 and 45 nm.

Example 4

Illumination Intensity Vs. Wall Material Refractive Index

Figure 22:
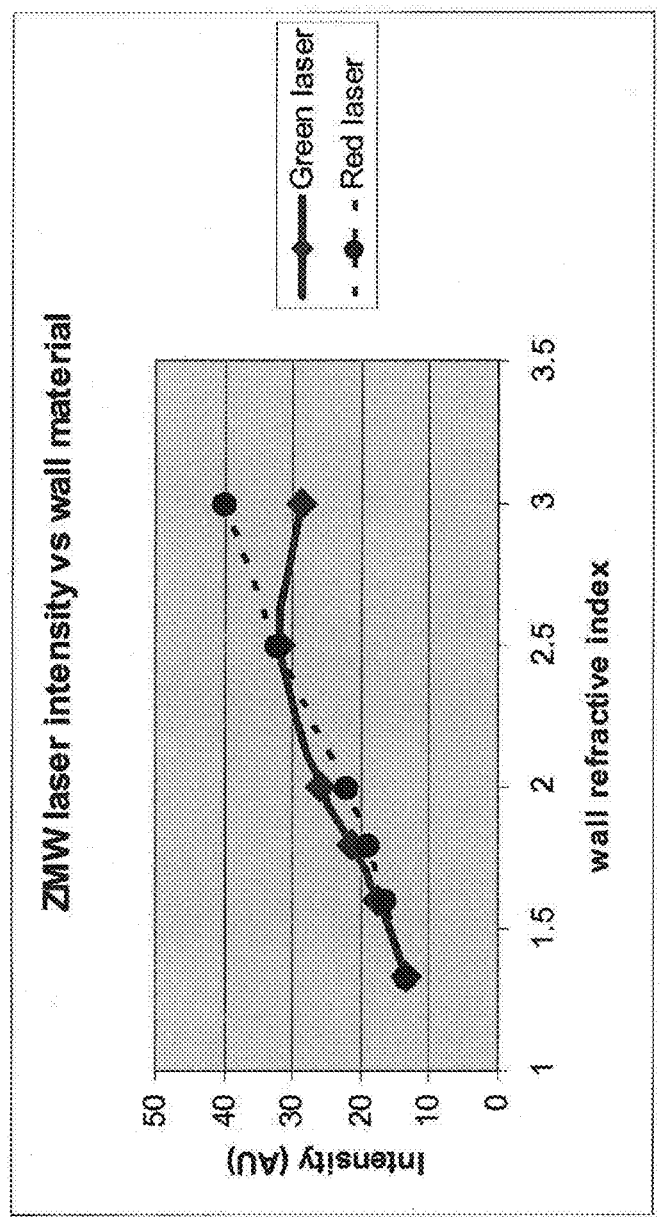
FIG. 22 shows a plot of ZMW illumination intensity versus the refractive index of the wall material for a green laser and a red laser.
Figure 23:
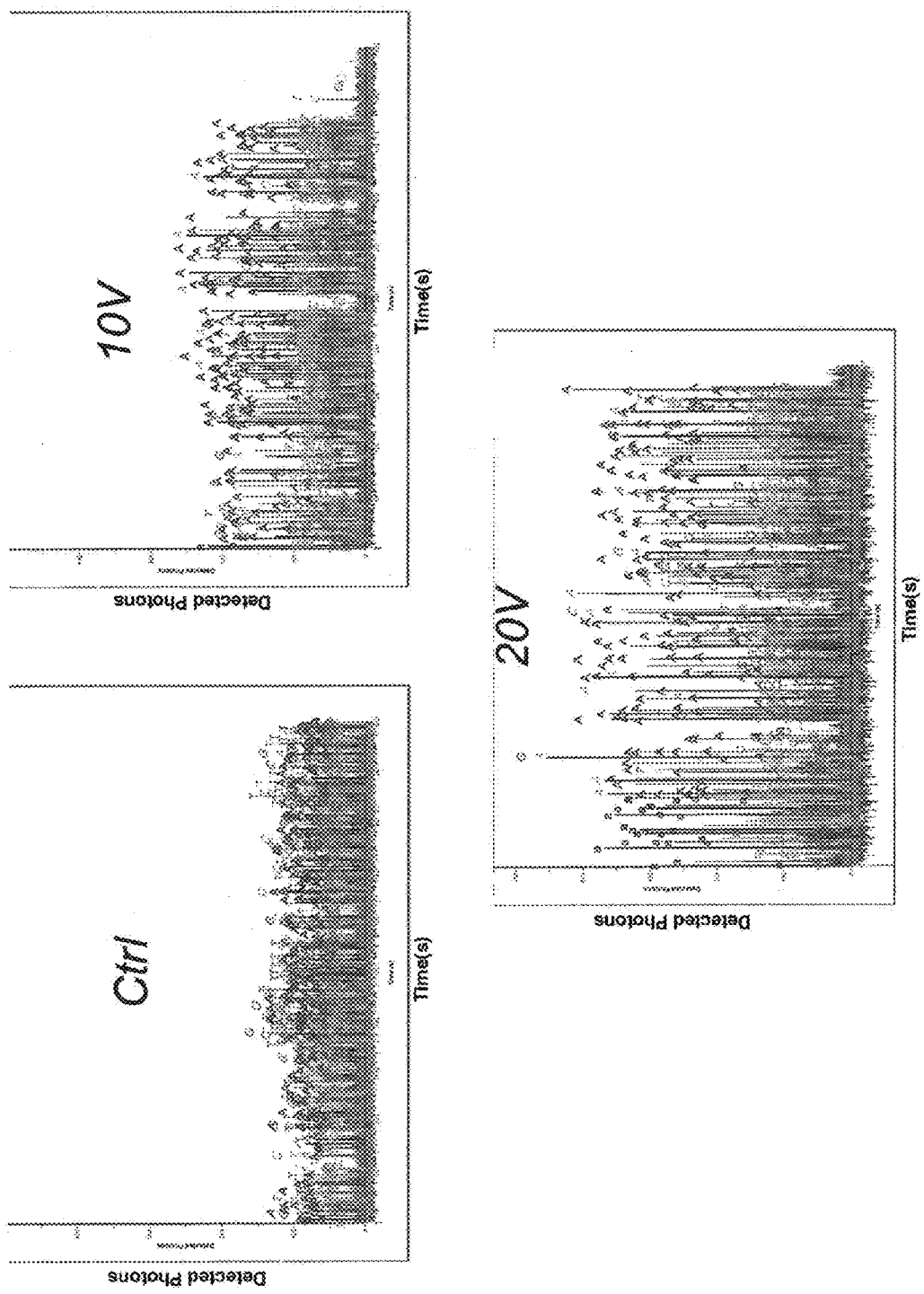
FIG. 23 shows single molecule sequencing data for sequencing runs carried out on ZMW arrays anodized at 10V and 20V, and on a control ZMW array not anodized.

A simulation was performed to calculate the illumination intensity in the region of the ZMW inside the non-reflective layers (the solution volume). FIG. 22 shows a plot of illumination intensity for a green laser (diamonds) and a red laser (circles). As can be seen from the plot, for the red laser, the illumination intensity increases with wall refractive index from about 1.3 to about 3. The illumination intensity increases for the green laser from a wall refractive index of 1.3 to about 2.5.

Example 5

Single Molecule Sequencing in ZMWs Having Non-Reflective Layers

A zero-mode waveguide array having about 3000 apertures through a 100 nm layer of Al on fused silica was used to characterize the influence of oxide thickness on DNA sequencing performance. Oxides of several thicknesses were generated using the electrochemical methods described above. In the current example, 10V and 20V were applied to ZMW arrays to generate 20 nm and 30 nm of aluminum oxide, respectively, on the aluminum substrate and inside the walls of the ZMWs. Following oxide generation, the substrates were treated with a specific biasing agent to prevent non-specific adsorption of sequencing components and to specifically immobilize the sequencing polymerase on the fused silica bottom of the ZMW (see, e.g. U.S. patent application Ser. No. 11/731,748, filed Mar. 29, 2007). Prior to sequencing, a single DNA polymerase molecule having a biotin label is complexed with a double stranded and primed DNA to form a polymerase-template-primer complex. This complex is immobilized on functionalized fused silica substrates of the zero-mode waveguides using streptavidin or neutravidin. The zero-mode waveguide array is exposed to a solution comprising labeled nucleotide bases. Each base is labeled with a unique fluorescent marker (organic dye) that serve as signatures for detection, 555-T, 568-G, 647-A and Cy5.5-C. Following immobilization of the DNA polymerase/template complex, the four bases in equal concentrations in buffer are added to the system along with manganese to catalyze the reaction. The fluorophores are excited by 532 nm and 641 nm lasers. Fluorescence emission is monitored using a cooled CCD camera and the time averaged spectra were converted to trace data acquired prior to data acquisition. FIG.

Figure 24:
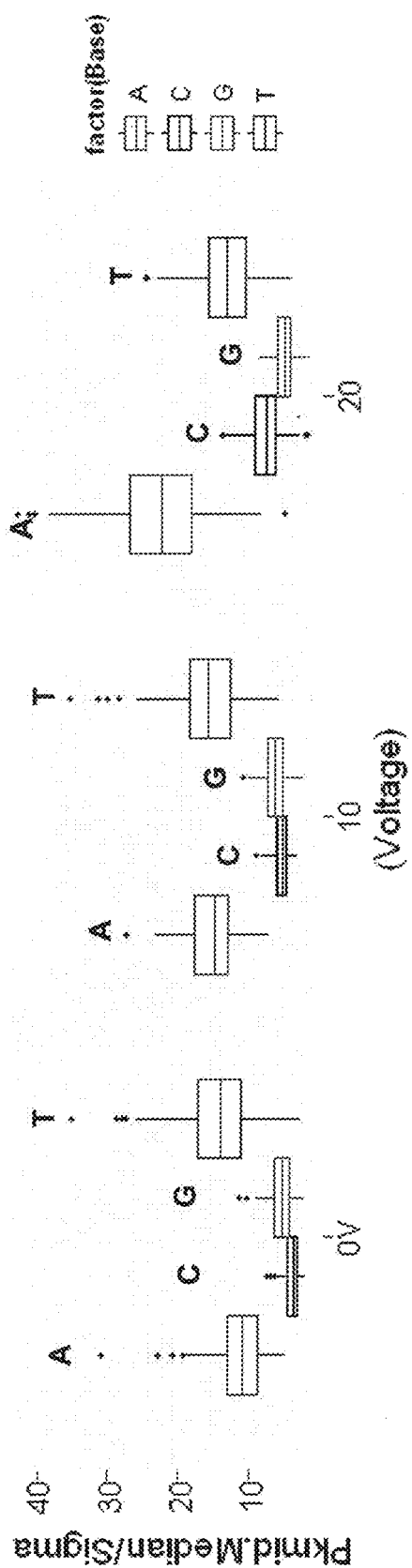
FIG. 24 shows the signal to noise measured for sequencing runs carried out on ZMW arrays anodized at 10V and 20V, and on a control ZMW array not anodized.
Figure 25:
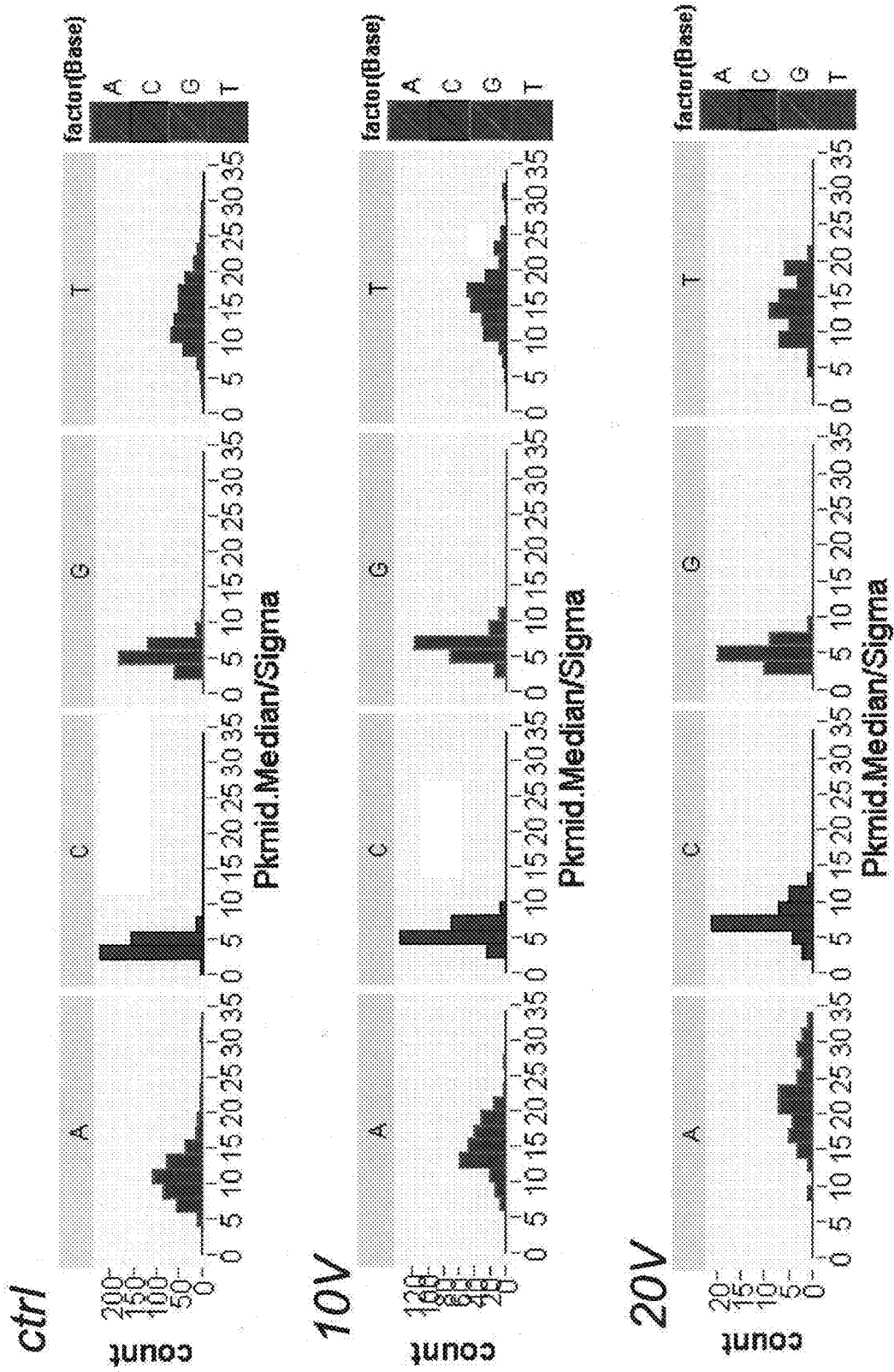
FIG. 25 shows the distribution of signal to noise for sequencing runs carried out on ZMW arrays anodized at 10V and 20V, and on a control ZMW array not anodized.

23 shows sequencing data in number of detected photons versus time, for a representative ZMWs for a control, and for arrays anodized at 10V and 20V. FIG. 24 shows signal to noise (Pkmid/Sigma) data for each of the four bases for a control, and for arrays anodized at 10V and 20V. FIG. 25 shows the distribution of signal-to-noise of sequencing pulses across a 3000 ZMW array for a control, and for arrays anodized at 10V and 20V. The data has been analyzed using base calling software in order to correlate the observed peaks with the labeled bases that comprise DNA, (A) adenine, (C) cytosine, (G) guanine and (T) thymine. As can be seen in the figures, the signal-to-noise (defined as the fluorescence intensity corresponding to analog incorporation divided by the diffusion background) of the red fluorophores (647-A) are markedly enhanced with increasing oxide thickness. In this example, the SNR was increased over that of the control by 1.5× and 2.25× for the 20 nm and 30 nm oxide thickness, respectively. The enhanced SNR enables improved sequencing accuracy by decreasing the fraction of dark analogs that may otherwise fall below the detection threshold of the sequencing system.

Although described in some detail for purposes of illustration, it will be readily appreciated that a number of variations known or appreciated by those of skill in the art may be practiced within the scope of present invention. To the extent not already expressly incorporated herein, all published references and patent documents referred to in this disclosure are incorporated herein by reference in their entirety for all purposes.

What is claimed is:

1. A method for producing waveguides having apertures that extend into a transparent substrate that are selectively functionalized on their bases comprising:
    providing an array of zero mode waveguides comprising an opaque layer on top of a silica-based transparent substrate layer wherein the zero mode waveguides comprise nanoscale apertures extending through the opaque layer and extending into the transparent layer, each zero mode waveguide having walls and a base;
    coating the array of zero mode waveguides such that the walls and the bases are coated with a non-reflective layer;
    etching back the non-reflective layer to expose the transparent substrate at the bases of the zero mode waveguides, thereby producing a non-reflective layer selectively on the walls of the zero mode waveguides and on the walls of the apertures extending into the transparent substrate layer, and
    treating the array with an agent that selectively functionalizes the aperture bases comprising exposed silica-based transparent substrate layer to produce an array of zero mode waveguides having apertures selectively functionalized on their bases.

2. The method of claim 1 wherein the coating process comprises a conformal coating.

3. The method of claim 1 wherein the etching back is performed using photolithography to define the region for etch back.

4. The method of claim 1 wherein bases of the apertures of the zero mode waveguides are selectively functionalized using a silane.

5. The method of claim 1 wherein the coating is performed using chemical vapor deposition (CVD).

6. The method of claim 1 wherein the coating is performed using atomic layer deposition (ALD).

7. The method of claim 1 wherein the coating is performed in the liquid phase.

8. The method of claim 1 wherein the non-reflective layer comprises an oxide.

9. The method of claim 8 wherein the oxide comprises $Al_2O_3$.

10. The method of claim 1 wherein the non-reflective layer comprises a polymer.

11. The method of claim 10 wherein the polymer comprises a polyimide.

12. The method of claim 1 wherein the array comprises more than 10,000 zero mode waveguides.

13. The method of claim 1 wherein the opaque layer comprises a metal.

14. The method of claim 1 wherein the zero mode waveguide has a diameter between about 1 nm and about 300 nm.

15. The method of claim 1 wherein the zero mode waveguide has a diameter between about 10 nm and about 200 nm.

* * * * *